United States Patent
Sandanayaka et al.

(10) Patent No.: US 11,034,660 B2
(45) Date of Patent: *Jun. 15, 2021

(54) HYDRAZIDE CONTAINING NUCLEAR TRANSPORT MODULATORS AND USES THEREOF

(71) Applicant: Karyopharm Therapeutics Inc., Newton, MA (US)

(72) Inventors: Vincent P. Sandanayaka, Northboro, MA (US); Sharon Shacham, Newton, MA (US); Dilara McCauley, Arlington, MA (US); Sharon Shechter, Andover, MA (US)

(73) Assignee: Karyopharm Therapeutics Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/696,702

(22) Filed: Nov. 26, 2019

(65) Prior Publication Data
US 2020/0339521 A1     Oct. 29, 2020

Related U.S. Application Data

(63) Continuation of application No. 16/203,181, filed on Nov. 28, 2018, now Pat. No. 10,544,108, which is a continuation of application No. 15/629,307, filed on Jun. 21, 2017, now Pat. No. 10,173,987, which is a continuation of application No. 14/940,310, filed on Nov. 13, 2015, now Pat. No. 9,714,226, which is a (Continued)

(51) Int. Cl.
| | |
|---|---|
| C07D 249/08 | (2006.01) |
| A61K 31/497 | (2006.01) |
| C07D 241/20 | (2006.01) |
| C07D 403/12 | (2006.01) |
| C07D 401/12 | (2006.01) |
| C07D 409/12 | (2006.01) |
| A61K 31/4196 | (2006.01) |
| A61K 31/4439 | (2006.01) |
| A61K 31/454 | (2006.01) |
| A61K 31/498 | (2006.01) |
| A61K 31/506 | (2006.01) |
| A61K 31/55 | (2006.01) |
| A61K 31/496 | (2006.01) |
| A61K 31/5377 | (2006.01) |

(52) U.S. Cl.
CPC ........ *C07D 249/08* (2013.01); *A61K 31/4196* (2013.01); *A61K 31/4439* (2013.01); *A61K 31/454* (2013.01); *A61K 31/496* (2013.01); *A61K 31/497* (2013.01); *A61K 31/498* (2013.01); *A61K 31/506* (2013.01); *A61K 31/5377* (2013.01); *A61K 31/55* (2013.01); *C07D 241/20* (2013.01); *C07D 401/12* (2013.01); *C07D 403/12* (2013.01); *C07D 409/12* (2013.01)

(58) Field of Classification Search
CPC .. C07D 249/08; C07D 241/20; C07D 401/12; C07D 403/12; C07D 409/12; A61K 31/4196; A61K 31/4439; A61K 31/454; A61K 31/496; A61K 31/497; A61K 31/498; A61K 31/506; A61K 31/5377; A61K 31/55
USPC ...................................................... 514/210.2
See application file for complete search history.

(56) References Cited

U.S. PATENT DOCUMENTS

| 5,153,201 A | 10/1992 | Aono et al. |
| 5,817,677 A | 10/1998 | Linz et al. |
| (Continued) | | |

FOREIGN PATENT DOCUMENTS

| CN | 101309912 A | 11/2008 |
| CN | 101466687 A | 6/2009 |
| (Continued) | | |

OTHER PUBLICATIONS

*Notice of Allowance for U.S. Appl. No. 16/203,181 mailed Oct. 3, 2019.

(Continued)

*Primary Examiner* — Kristin A Vajda
(74) *Attorney, Agent, or Firm* — Foley Hoag LLP

(57) ABSTRACT

The invention generally relates to nuclear transport modulators, e.g., CRM1 inhibitors, and more particularly to a compound represented by structural formula I:

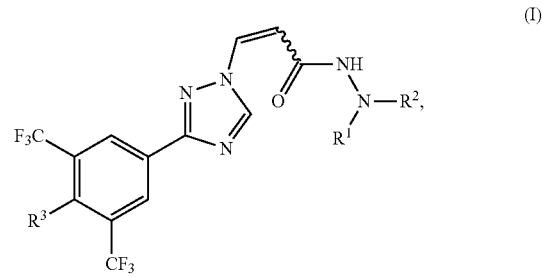

or a pharmaceutically acceptable salt thereof, wherein the values and alternative values for the variables are as defined and described herein. The invention also includes the synthesis and use of a compound of structural formula I, or a pharmaceutically acceptable salt or composition thereof, e.g., in the treatment, modulation and/or prevention of physiological conditions associated with CRM1 activity.

13 Claims, 8 Drawing Sheets

Related U.S. Application Data continuation of application No. 14/735,853, filed on Jun. 10, 2015, now Pat. No. 9,206,158, which is a continuation of application No. 14/235,306, filed as application No. PCT/US2012/048319 on Jul. 26, 2012, now Pat. No. 9,079,865.

(60) Provisional application No. 61/513,428, filed on Jul. 29, 2011, provisional application No. 61/513,432, filed on Jul. 29, 2011, provisional application No. 61/610,178, filed on Mar. 13, 2012, provisional application No. 61/653,588, filed on May 31, 2012, provisional application No. 61/654,651, filed on Jun. 1, 2012.

(56) References Cited

U.S. PATENT DOCUMENTS

| | | |
|---|---|---|
| 6,462,049 B1 | 10/2002 | Ogura et al. |
| 7,342,115 B2 | 3/2008 | Hutchison et al. |
| 7,667,041 B2 | 2/2010 | Kimura et al. |
| 7,795,457 B2 | 9/2010 | Fu et al. |
| 7,858,621 B2 | 12/2010 | Kim et al. |
| 7,902,367 B2 | 3/2011 | Nomura et al. |
| 8,273,738 B2 | 9/2012 | Osakada et al. |
| 8,299,102 B2 | 10/2012 | Strobel et al. |
| 8,304,438 B2 | 11/2012 | Strobel et al. |
| 8,513,230 B2 | 8/2013 | Shacham et al. |
| 8,598,168 B2 | 12/2013 | Moradei et al. |
| 8,999,996 B2 * | 4/2015 | Sandanayaka .......... A61P 29/00 514/255.06 |
| 9,079,865 B2 * | 7/2015 | Sandanayaka ....... A61K 31/506 |
| 9,096,543 B2 | 8/2015 | Sandanayaka et al. |
| 9,206,158 B2 * | 12/2015 | Sandanayaka ....... A61K 31/454 |
| 9,266,843 B2 | 2/2016 | Sandanayaka et al. |
| 9,303,000 B2 | 4/2016 | Sandanayaka et al. |
| 9,428,490 B2 | 8/2016 | Sandanayaka et al. |
| 9,550,757 B2 | 1/2017 | Shacham et al. |
| 9,585,874 B2 | 3/2017 | Sandanayaka et al. |
| 9,714,226 B2 * | 7/2017 | Sandanayaka ....... A61K 31/506 |
| 9,738,624 B2 | 8/2017 | Baloglu et al. |
| 9,828,373 B2 | 11/2017 | Liu et al. |
| 9,861,614 B2 | 1/2018 | Sandanayaka et al. |
| 10,058,535 B2 | 8/2018 | Sandanayaka et al. |
| 10,173,987 B2 * | 1/2019 | Sandanayaka ....... C07D 249/08 |
| 10,202,366 B2 | 2/2019 | Rashal et al. |
| 10,335,393 B2 | 7/2019 | Sandanayaka et al. |
| 10,407,405 B2 | 9/2019 | Baloglu et al. |
| 10,519,139 B2 | 12/2019 | Austad et al. |
| 10,526,295 B2 | 1/2020 | Baloglu |
| 10,544,108 B2 * | 1/2020 | Sandanayaka ....... A61K 31/506 |
| 10,709,706 B2 | 7/2020 | Baloglu |
| 2003/0018025 A1 | 1/2003 | Thurkauf et al. |
| 2004/0092598 A1 | 5/2004 | Watkins et al. |
| 2006/0004069 A1 | 1/2006 | Momose et al. |
| 2009/0221586 A1 | 9/2009 | Okada et al. |
| 2009/0298896 A1 | 12/2009 | Sakuma et al. |
| 2010/0016272 A1 | 1/2010 | Strobel et al. |
| 2010/0056569 A1 | 3/2010 | Nan et al. |
| 2011/0009374 A1 | 1/2011 | Keller |
| 2011/0275607 A1 | 11/2011 | Shacham et al. |
| 2012/0258986 A1 | 10/2012 | Sandanayaka et al. |
| 2013/0317031 A1 | 11/2013 | Sandanayaka et al. |
| 2014/0155370 A1 | 6/2014 | Shacham et al. |
| 2014/0235653 A1 | 8/2014 | Sandanayaka et al. |
| 2014/0364408 A1 | 12/2014 | Sandanayaka et al. |
| 2015/0018332 A1 | 1/2015 | Sandanayaka et al. |
| 2015/0111893 A1 | 4/2015 | Sandanayaka et al. |
| 2015/0274698 A1 | 10/2015 | Sandanayaka et al. |
| 2016/0145246 A1 | 5/2016 | Sandanayaka et al. |
| 2016/0152596 A1 | 6/2016 | Baloglu et al. |
| 2016/0258931 A1 | 9/2016 | Silva et al. |
| 2016/0304500 A1 | 10/2016 | Rashal et al. |
| 2017/0137430 A1 | 5/2017 | Sandanayaka et al. |
| 2017/0319551 A1 | 11/2017 | Sandanayaka et al. |
| 2018/0155317 A1 | 6/2018 | Baloglu et al. |
| 2019/0016690 A1 | 1/2019 | Baloglu |
| 2019/0023693 A1 | 1/2019 | Chennuru et al. |
| 2019/0160063 A1 | 5/2019 | Baloglu |
| 2020/0087313 A1 | 3/2020 | Sandanayaka et al. |
| 2020/0199099 A1 | 6/2020 | Baloglu et al. |
| 2020/0283419 A1 | 9/2020 | Austad et al. |
| 2020/0339521 A1 | 10/2020 | Sandanayaka et al. |

FOREIGN PATENT DOCUMENTS

| | | |
|---|---|---|
| CN | 103002742 A | 3/2013 |
| CN | 103874690 B | 7/2016 |
| EP | 0069513 A2 | 1/1983 |
| EP | 1 939 180 A1 | 7/2008 |
| EP | 1992618 A1 | 11/2008 |
| EP | 2003118 A1 | 12/2008 |
| EP | 2 090 570 A1 | 8/2009 |
| JP | S5841875 A | 3/1983 |
| JP | S62103065 A | 5/1987 |
| JP | H04211089 A | 8/1992 |
| JP | H07118237 A | 5/1995 |
| JP | H11263764 A | 9/1999 |
| JP | 2003/342262 A | 12/2003 |
| JP | 2004509941 A | 4/2004 |
| JP | 2004168768 A | 6/2004 |
| JP | 2005-508905 A | 4/2005 |
| JP | 2005-255683 A | 9/2005 |
| JP | 2006-504761 A | 2/2006 |
| JP | 2007-210929 A | 8/2007 |
| JP | 2009-203238 A | 9/2009 |
| JP | 2009-536615 A | 10/2009 |
| JP | 2009-544696 A | 12/2009 |
| JP | 2010-513341 A | 4/2010 |
| JP | 2010-519337 A | 6/2010 |
| WO | WO-96/16040 A1 | 5/1996 |
| WO | WO-97/15567 A1 | 5/1997 |
| WO | WO-97/37996 A1 | 10/1997 |
| WO | WO-97/48696 A1 | 12/1997 |
| WO | WO-98/25893 A1 | 6/1998 |
| WO | WO-99/50264 A1 | 10/1999 |
| WO | WO-01/62756 A1 | 8/2001 |
| WO | WO-02/26696 A1 | 4/2002 |
| WO | WO-2003/024448 A2 | 3/2003 |
| WO | WO-2004/039365 A1 | 5/2004 |
| WO | WO-2004/039764 A1 | 5/2004 |
| WO | WO-2004/043925 A2 | 5/2004 |
| WO | WO-2004/043951 A1 | 5/2004 |
| WO | WO-2004/076418 A1 | 9/2004 |
| WO | WO-2005/115990 A1 | 12/2005 |
| WO | WO-2006/016637 A1 | 2/2006 |
| WO | WO-2006/019020 A1 | 2/2006 |
| WO | WO-2006/088246 A1 | 8/2006 |
| WO | WO-2007/102580 A1 | 9/2007 |
| WO | WO-2007/147336 A1 | 12/2007 |
| WO | WO-2008/029825 A1 | 3/2008 |
| WO | WO-2008/074413 A2 | 6/2008 |
| WO | WO-2008/152097 A1 | 12/2008 |
| WO | WO-2010/017545 A2 | 2/2010 |
| WO | WO-2011/069039 A1 | 6/2011 |
| WO | WO-2011/109799 A1 | 9/2011 |
| WO | WO-2012/099807 A1 | 7/2012 |
| WO | WO-2013/019548 A1 | 2/2013 |
| WO | WO-2013/019561 A1 | 2/2013 |
| WO | WO-2013/020024 A2 | 2/2013 |
| WO | WO-2013/170068 A2 | 11/2013 |
| WO | WO-2014/144772 A1 | 9/2014 |
| WO | WO-2014/152263 A1 | 9/2014 |
| WO | WO-2014/205389 A1 | 12/2014 |
| WO | WO-2014/205393 A1 | 12/2014 |
| WO | WO-2016/025904 A1 | 2/2016 |
| WO | WO-2017/117529 A1 | 7/2017 |
| WO | WO-2017/117535 A1 | 7/2017 |
| WO | WO-2018/098472 A1 | 5/2018 |
| WO | WO-2018/129227 A1 | 7/2018 |

(56) References Cited

OTHER PUBLICATIONS

*Notice of Allowance for U.S. Appl. No. 13/891,044 "Nuclear Transport Modulators and Uses Thereof", dated Apr. 7, 2015.
*Notice of Allowance for U.S. Appl. No. 13/931,372 "Nuclear Transport Modulators and Uses Thereof", dated Sep. 7, 2016.
*Notice of Allowance for U.S. Appl. No. 14/235,342 "Nuclear Transport Modulators and Uses Thereof", dated Apr. 25, 2016.
*Notice of Allowance for U.S. Appl. No. 14/735,853 "Nuclear Transport Modulators and Uses Thereof", dated Aug. 4, 2015.
*Notice of Allowance for U.S. Appl. No. 14/747,394 "Nuclear Transport Modulators and Uses Thereof", dated Aug. 30, 2017.
*Notice of Allowance for U.S. Appl. No. 14/900,469 "Nuclear Transport Modulators and Uses Thereof", dated Apr. 18, 2017.
*Notice of Allowance for U.S. Appl. No. 14/940,310 "Hydrazide Containing Nuclear Transport Modulators and Uses Thereof", dated Mar. 14, 2017.
*Notice of Allowance for U.S. Appl. No. 14/989,377 "Nuclear Transport Modulators and Uses Thereof", dated Oct. 28, 2016.
*Notice of Allowance for U.S. Appl. No. 15/413,889 "Nuclear Transport Modulators and Uses Thereof", dated Apr. 10, 2018.
*Notice of Allowance for U.S. Appl. No. 15/651,856, "Nuclear Transport Modulators and Uses Thereof" dated Apr. 24, 2019.
*Requirement for Restriction/Election for U.S. Appl. No. 13/041,377 "Nuclear Transport Modulators and Uses Thereof", dated Jul. 5, 2012.
*Requirement for Restriction/Election for U.S. Appl. No. 13/350,864 "Olefin Containing Nuclear Transport Modulators and Uses Thereof", dated Dec. 19, 2013.
*Requirement for Restriction/Election for U.S. Appl. No. 13/931,372 "Nuclear Transport Modulators and Uses Thereof", dated May 22, 2014.
*Requirement for Restriction/Election for U.S. Appl. No. 14/235,342 "Nuclear Transport Modulators and Uses Thereof", dated Jun. 9, 2015.
*Requirement for Restriction/Election for U.S. Appl. No. 14/777,302 "Methods of Promoting Wound Healing Using CRM1 Inhibitors", dated Sep. 22, 2016.
*Requirement for Restriction/Election for U.S. Appl. No. 15/217,514 "Nuclear Transport Modulators and Uses Thereof", dated Aug. 8, 2017.
Balsamini, "(E)-3-(2-(N-Phenylcarbamoyl)vinyl)pyrrole-2-carboxylic Acid Derivatives. A Novel Class of Glycine Site Antagonists", Journal of Medicinal Chemistry, 41(6):808-820 (Jan. 1, 1998).
Brekhov, Y. et al., "Cyanomethyltetrazoles II reactions of the methylene Fragment", Zhurnal organicheskoi Khimii, 28(9): 1921-1925 (1992).
Brittain, "Drugs in Pharmaceutical Sciences, v. 192. Polymorphism in Pharmaceutical Solids," CRC Press (2009).
Bryn, "Pharmaceutical Solids: A Strategic Approach to Regulatory Considerations," Pharma Res 12(7):945-954 (1995).
Buckler, R.T. et al., "Synthesis and Antiinflammatory Activity of Some 1,2,3- and 1,2,4-Triazolepropionic Acids", Journal of Medicinal Chemistry, 21(12): 1254-1260 (1978).
Burdeska et al., "Anil-Synthese. 23. Mitteilung. Ueber die Herstellung von Styryl- and Stilbenyl-Derivaten des Pyrimidins // Anil synthesis. Part 23. Preparation of styryl and stilbenyl derivatives of pyrimidines," Helv Chim Acta, 64(1): 113-152 (1981).
Cai, X., et al., "Inhibition of Thr-55 phosphorylation restores p53 nuclear localization and sensitizes cancer cells to DNA damage", Proc Nat Acad Sci, 105(44):16958-16963 (2008).
Cancer [online], [retrieved on Jul. 6, 2007] Retrieved from the Internet, URL: http://www.nlm.nih.gov/medlineplus/cancer.html (Year: 2007).
Cantu et al., "Using the Selective Inhibitor of Nuclear Export (SINE) Compound KPT-350 to Reduce Cortical Circuit Hyperexcitability and Interneuron Cell Loss in the Controlled Cortical Impact (CCI) Model of Traumatic Brain Injury (TBI) (I11.001)," Neurology, 86(16 Supplement):IT1.001 (2016).

Chemcats RN# 1035122-02-1; Publicly available on Jul. 12, 2009.
Chemcats RN# 1134927-58-4; Publicly available on Apr. 15, 2009.
Chemcats RN# 930886-49-0; Publicly available on Apr. 29, 2007.
Chemical Abstract Registry Nos. 1181485-58-4; 1100108-00-6.
Cheng et al., "XPO1 (CRM1) Inhibition Represses STAT3 Activation to Drive a Surviving-Dependent Oncogenic Switch in Triple-Negative Breast Cancer," Mol Cancer Ther 13(3):675-686 (2014).
Cooper et al., "Synthesis of Some 1,2,4-Triazoles and 1,2,4-Triazolines by Reaction of Oxamidrazone Condensation Products with Acetic Anhydride," Journal of Chemical Society Perkin Transactions 1, 15: 1433-1437 (1975).
Cronshaw, J.M. et al., "The nuclear pore complex: disease associations and functional correlations", TRENDS Endocrin Metab. 15:34-39 (2004).
Daelemans, D. et al., "A synthetic HIV-1 Rev inhibitor interfering with the CRM1-mediated nuclear export", PNAS, 99(22):14440-14445 (2002).
Database PubChem Compound, Database Accession No. 33777540 (May 29, 2009), 3 pages.
Database PubChem Compound, Database Accession No. 33777561 (May 29, 2009), 3 pages.
Database PubChem Compound, Database Accession No. 33777585 (May 29, 2009), 3 pages.
Database PubChem Compound, Database Accession No. 66525271 (Oct. 24, 2012), 3 pages.
Database PubChem Compound, Database Accession No. 66525276 (Oct. 24. 2012), 3 pages.
Database PubChem Compound, Database Accession No. 72062355 (2007), 11 pages.
Database PubChem Compound, Database Accession No. 940775133 (Jul. 7, 2017), 1 page.
Davis, J.R. et al., "Controlling protein compartmentalization to overcome disease" Pharmaceut Res., 24:17-27 (2007).
Dorwald, "Side Reactions in Organic Synthesis: A Guide to Successful Synthesis Design," Wiley-VCH Verlag GmbH & Co. KGaA, Weinheim (2005).
Etchin et al., "KPT-330 inhibitor of CRM1 (XPO1)-mediated nuclear export has selective anti-leukaemic activity in preclinical models of T-cell acute lymphoblastic leukaemia and acute myeloid leukaemia," British Journal of Haematology, 161:117-127 (2013).
Extended European Search Report for EP Application No. 17189480.1 dated May 16, 2018.
Extended European Search Report for EP Application No. EP 18202641 dated Feb. 15, 2019.
Extended European Search Report issued by the European Patent Office in corresponding European Application No. 18164757.0 dated Aug. 8, 2018.
Extended Search Report for EP Application No. 11751491.9, "Nuclear Transport Modulators and Uses Thereof", Date of Completion of the Search: Dec. 17, 2013. (4823.1003-007), 6 pages.
Extended Search Report for EP Application No. 12736172.3, "Olefin Containing Nuclear Transport Modulators and Uses Thereof", Date of Completion of the Search: May 8, 2014. (4823.1005-006), 3 pages.
Falini, B. et al., "Both carboxy-terminus NES motif and mutated tryptophan(s) are crucial for aberrant nuclear export of nucleophosmin leukemic mutants in NPMc+ AML", Blood Journal, 107(11):4514-4523 (2013).
Freundt, E.G. et al., "Molecular Determinants for Subcellular Localization of the Severe Acute Respiratory Syndrome Coronavirus Open Reading Frame 3b Protein", Journal of Virology, 83(13):6631-6640 (Jul. 2009).
Ghildyal, R. et al., "The Respiratory Syncytial Virus Matrix Protein Possesses a Crm1-Mediated Nuclear Export Mechanism", Journal of Virology, 83(11):5353-5362 (2009).
Ghosh, C.C. et al., "Analysis of nucleocytoplasmic shuttling of NF kappa B proteins in human leukocytes", Methods Mol. Biol. 457:279-92 (2008).
Golub, T.R. et al., "Molecular Classification of Cancer: Class Discovery and Class Prediction by Gene Expression Monitoring", Science, 286: 531-537 (1999).
Gravina et al., "XPO1/CRM1-Selective inhibitors of nuclear export (SINE) reduce tumor spreading and improve overall survival in

(56) References Cited

OTHER PUBLICATIONS preclinical models of prostate cancer (PCa)," Journal of Hematology & Oncology, 7(46):1-17 (2014).
Gupta, N. et. al., "Retinal tau pathology in human glaucomas" Can J Ophthalmol. 43(1):53-60 (2008).
Haines et al., "Selective Inhibitors of Nuclear Export Avert Progression in Preclinical Models of Inflammatory Demyelination," Nature Neuroscience, 18(4): 511-520 (2015).
Hilliard et al., "The anti-inflammatory prostaglandin 15-Deoxy-Δ12, 14 PGJ2 inhibits CRM1-dependent nuclear protein export," Journal of Biological Chemistry, 1-12 (2010).
Hoffman et al., "Synthesis of Vinyl-Functionalized Oxazoles by Olefin Cross-Metathesis", J. Org. Chem. 73: 2400-2403 (2008).
Hoshino, I. et al., "Combined effects of p53 gene therapy and leptomycin B in human esophageal squamous cell carcinoma", Oncology, 75:113-119 (2008).
Huff, J., "HIV Protease: A Novel Chemotherapeutic Target for AIDS", Journal of Medicinal Chemistry, 34(8): 2305-2314 (1991).
International Preliminary Report on Patentability for International Application No. PCT/US2011/027328, "Nuclear Transport Modulators and Uses Thereof" dated Sep. 11, 2012.
International Preliminary Report on Patentability for International Application No. PCT/US2012/021406, "Olefin Containing Nuclear Transport Modulators and Uses Thereof" dated Jul. 17, 2013.
International Preliminary Report on Patentability for International Application No. PCT/US2014/029322 dated Sep. 15, 2015.
International Preliminary Report on Patentability for International Application No. PCT/US2014/043479, dated Dec. 22, 2015.
International Preliminary Report on Patentability for International Application No. PCT/US2014/043484, dated Dec. 22, 2015.
International Preliminary Report on Patentability for International Application No. PCT/US2015/045395 dated Feb. 21, 2017.
International Preliminary Report on Patentability for International Application No. PCT/US2016/069492 dated Jul. 3, 2018.
International Preliminary Report on Patentability for International Application No. PCT/US2016/069508 dated Jul. 3, 2018.
International Preliminary Report on Patentability for International Application No. PCT/US2017/063439 dated May 28, 2019.
International Preliminary Report on Patentability for International Application No. PCT/US2012/048319, "Hydrazide Containing Nuclear Transport Modulators and Uses Thereof"; Date of Issuance of the Report: Feb. 4, 2014.
International Preliminary Report on Patentability for International Application No. PCT/US2012/048368, "Nuclear Transport Modulators and Uses Thereof"; Date of Issuance of the Report: Feb. 4, 2014.
International Preliminary Report on Patentability for International Application No. PCT/US2013/040404, "Nuclear Transport Modulators and Uses Thereof"; Date of Issuance of the Report: Nov. 11, 2014.
International Search Report and The Written Opinion of the International Searching Authority for International Application No. PCT/US2012/021406, "Olefin-Containing Nuclear Transport Modulators and Uses Thereof" dated Apr. 30, 2012.
International Search Report and The Written Opinion of the International Searching Authority for International Application No. PCT/US2012/049470, "Maleimide Compounds and Methods of Treatment," dated Feb. 13, 2013.
International Search Report and The Written Opinion of the International Searching Authority for International Application No. PCT/US2013/040404, "Nuclear Transport Modulators and Uses Thereof"; dated Nov. 18, 2013.
International Search Report and the Written Opinion of the International Searching Authority, or the Declaration for International Application No. PCT/US2014/027136 "Exo Olefin-Containing Nuclear Transport Modulators and Uses Thereof"; dated Jul. 11, 2014.
International Search Report and the Written Opinion of the International Searching Authority, or the Declaration for International Application No. PCT/US2014/029322 "Methods of Promoting Wound Healing Using CRM1 Inhibitors"; dated May 28, 2014.
International Search Report and the Written Opinion of the International Searching Authority, or the Declaration for International Application No. PCT/US2014/043479 "Nuclear Transport Modulators and Uses Thereof"; dated Sep. 17, 2014.
International Search Report and the Written Opinion of the International Searching Authority, or the Declaration for International Application No. PCT/US2014/043484 "Nuclear Transport Modulators and Uses Thereof"; dated Sep. 2, 2014.
International Search Report and Written Opinion for International Application No. PCT/US2015/045395 dated Jan. 12, 2016.
International Search Report and Written Opinion for International Application No. PCT/US2016/069492 dated Feb. 16, 2017.
International Search Report and Written Opinion for International Application No. PCT/US2016/069508 dated May 23, 2017.
International Search Report and Written Opinion for International Application No. PCT/US2017/063439 dated Feb. 2, 2018.
International Search Report for International Application No. PCT/US2011/027328, "Nuclear Transport Modulators and Uses Thereof" dated Apr. 29, 2011.
International Search Report for International Application No. PCT/US2012/048319, "Hydrazide Containing Nuclear Transport Modulators and Uses Thereof" dated Nov. 9, 2012.
International Search Report for International Application No. PCT/US2012/048368, "Nuclear Transport Modulators and Uses Thereof" dated Sep. 21, 2012.
Jiang et al., "Palladium-Catalyzed Alkenylation of 1,2,3-Trizoles with Terminal Conjugated Alkenes by Direct C-H Bond Functionalization," Eur J Org Chem, 7:1227-30 (2010).
Karyagin, A. Yu., Reagents for addressed modification of biopolymers, Russian Chemical Bulletin, 2000, 49(3):540-5.
Karyopharm Therapeutics, "Karyopharm Presents Data Demonstrating the Potential of Nuclear Export Protein Exportin 1 (XPO1) Inhibition in the Treatment of Traumatic Brain Injury," Apr. 20, 2016, Retrieved from the Internet: http://investors.karyopharm.com/static-files/577eb861-4183-463a-9a5b-d0f1def1629d [retrieved on Jan. 25, 2018].
Kau, T.R. et al., "A chemical genetic screen identifies inhibitors of regulated nuclear export of a Forkhead transcription factor in PTEN-deficient tumor cells", Cancer Cell, pp. 463-476 (2003).
Kaur et al., "Tyrphostin Induced Growth Inhibition: Correlation with Effect on p210bcr-abl Autokinase Activity in K562 Chronic Myelogenous Leukemia," Anti-Cancer Drugs, 5(2): 213-222 (1994).
Lain, S. et al., "Accumulating active p53 in the nucleus by inhibition of nuclear export: a novel strategy to promote the p53 tumor suppressor function", Exp Cell Res. 253: 315-324 (1999).
Lain, S. et al., "An inhibitor of nuclear export activates the p53 response and induces the localization of HDM2 and p53 to U1A-positive nuclear bodies associated with the PODs", Exp Cell Res. 248:457-472 (1999).
Lala, P.K. et al., "Role of nitric oxide in tumor progression: Lessons from experimental tumors", Cancer and Metastasis Reviews, 17: 91-106 (1998).
Lapalombella, R. et al., "Selective Inhibitors of nuclear exports show that CRM1/XPO1 is a target in chronic lymphocytic leukemia", Blood, 120(23): 4621-4634 (Nov. 29, 2012).
Li, A. et al., "Upregulation of CRM1 Relates to Neuronal Apoptosis after Traumatic Brain Injury in Adult Rats", J Mol Neurosci, 51(1):208-218 (2013).
Maekawa et al., "Efficient Formation of a Triazole Ring Via Novel Ring-Opening Reaction of (z)-2-Methyl-4-arylmethylene-5(4H)-Oxazolones with Hydrazides," Heterocycles, 75(12): 2959-2971 (2008).
Maga et al., "Pharmacophore modeling and molecular docking led to the discovery of inhibitors of human immunodeficiency virus-1 replication targeting the human cellular aspartic acid-glutamic acid-alanine-aspartic acid box polypeptide 3," J Med Chem, 51(21):6635-8 (2008).
Marelli et al., "Tumor targeting via integrin ligands," Frontiers in Oncology, 3(222):1-12 (2013).
Miskolci et al., "TNFα release from peripheral blood leukocytes depends on a CRM1-mediated nuclear export," Biochemical and Biophysical Research Communications, 351:354-360 (2006).

(56) References Cited

OTHER PUBLICATIONS

Modzelewska-Banachiewicz, B. et al., "Synthesis and biological activity of (Z) and (E) isomers of 3-(3,4-diaryl-1,2,4-triazole-5-yl)prop-2-enoic acid" Monatsh Chem. 140:439-444 (2009).
Modzelewska-Banachiewicz, B. et al., "Synthesis and biological activity of new derivatives of 3-(3,4-diaryl-1,2,4-triazole-5-yl)propenoic acid" European Journal of Medicinal Chemistry, 39:873-877 (2004).
Monecke, T. et al., "Crystal Structure of the Nuclear Export Receptor CRM1 in Complex with Snurportin1 and RanGTP", Science, 324:1087-1091 (2009).
Morales et al., "Mechanical Particle-Size Reduction Techniques, Formulating Poorly Water Soluble Dugs," AAPS Advances in Pharmaceutical Sciences Series, 133-170 (2012).
Morissette et al., "High-throughput crystallization: polymorphs, salts, co-crystals and solvates of pharmaceutical solids," Adv Drug Deliv Rev, 56(3):275-300 (2004).
Muller, P.A.J. et al., "Nuclear-Cytosolic Transport of COMMD1 Regulates NF-κB and HIF-1 Activity", Traffic, 10:514-527 (2009).
Mutka et al., "Identification of Nuclear Export Inhibitors with Potent Anticancer Activity in Vivo," Cancer Research, 69(2): 510-517 (2009).
Mutka, S. et al., "Nuclear export inhibitors (NEIs) as novel cancer therapeutics", 98th AACr Ann. Mtg., 2 pgs (Apr. 14-18, 2007) (Poster).
Nagase, The Practice of Medicinal Chemistry, Chapter 13. Conversion of Molecules Based on Equivalent Substitution, vol. 1, Technomics Inc., 1998, 253.
Nair, V., "Thermally induced skeletal rearrangement in a triazepine," J Heterocyclic Chem, 12(1):183-4 (1975).
Nakahara, J. et al., "Abnormal expression of TIP30 and arrested nucleocytoplasmic transport within oligodendrocyte precursor cells in multiple sclerosis", Journal of Clinical Investigation, 119(1):169-181 (2009).
Nautiyal et al., "Distinct functions for RIP140 in development, inflammation, and metabolism," Trends in Endocrinology and Metabolism, 24(9):451-459 (2013).
Noske, A., et al., "Expression of the Nuclear Export Protein Chromosomal Region Maintenance/Exportin 1/Xpo1 Is a Prognostic Factor in Human Ovarian Cancer", Cancer, 112(8):1733-1743 (2008).
Orsted et al., "Basic principles of wound healing," Wound Care Canada, 9(2): 4-12 (2011).
Patani, G.A., et al., "Bioisosterism: A Rational Approach in Drug Design", Chem Rev, 96:3147-3176 (1996).
Procopiou et al., "Inhibitors of Cholesterol Biosynthesis. 2. 3,5-Dihydroxy-7-(N-pyrrolyl)-6-heptenoates, a Novel Series of HMG-CoA Reductase Inhibitors," J Med Chem, 36(23): 3658-3662 (1993).
Quan, M.L. et al., "Design and Synthesis of Isoxazoline Derivatives as Factor Xa Inhibitors", J. Med. Chem. 42: 2760-2773 (1999).
Rawlinson, S.M. et al., "CRM1-mediated Nuclear Export of Dengue Virus RNA Polymerase NS5 Modulates Interleukin-8 Induction and Virus Production", Journal of Biological Chemistry, 284(23):15589-15597 (2009).
Registry(STN)[online], Jan. 23, 2008, CAS registered No. 1000508-38-2, 1 page.
Sakamoto et al., "Studies on Pyrimidine Derivatives. XXV. Reaction of Pyrimidinyl Aldehydes and Ketones with Wittig Reagents," Chem Pharm Bull, 30(2): 610-614 (1982).
Sanchez, V. et al., "Nuclear Export of the Human Cytomegalovirus Tegument Protein pp65 Requires Cyclin-Dependent Kinase Activity and the Crm1 Exporter", Journal of Virology, 81(21):11730-11736 (2007).
Shaoyong, Ke. et al., "Research Advance of Acylhydrazine Derivatives with Biological Activities", Chinese Journal of Organic Chemistry 30(12):1820-1830 (2010).
Shasheva, "Reactions of Hydroxyphenyl-Substituted 1,2,4-Triazoles with Electrophilic Reagents", Russian Journal of General Chemistry, 79(10): 2234-2243 (2009).
Sorokin, A.V. et al., "Nucleocytoplasmic Transport of Proteins", Biochemistry Moscow, 72(13):1439-1457 (2007).
Storey et al., "Solid State Characterization of Pharmaceuticals," Blackwell Publishing, (2011).
Sun Q., et al., "Nuclear export inhibition through covalent conjugation and hydrolysis of Leptomycin B by CRM1", Proc Nat Acad Sci, 110(4): 1303-1308 (2013).
Tai et al., "CRM1 inhibition induces tumor cell cytotoxicity and impairs osteoclastogenesis in multiple myeloma: molecular mechanisms and therapeutic implications," Leukemia, 28:155-165 (2014).
Tamir et al., "KPT-350, a Selective Inhibitor of Nuclear Export (SINE) Compound, Shows Efficacy in the Mouse Pilocapine Model of Temporal Lobe Epilepsy," Journal of Neurological Sciences, 381: 87-88 (2017).
Terry, L.J. et al., "Crossing the Nuclear Envelope: Hierarchical Regulation of Nucleocytoplasmic Transport", Science, 318:1412-1416 (2007).
van der Watt, P.J. et al., "The Karyopherin proteins, Crm1 and Karyopherin β1, are overexpressed in cervical cancer and are critical for cancer cell survival and proliferation", Int. J. Cancer, 124:1829-1840 (2009).
Van Neck et al., "Inhibition of the CRM1-mediated nucleocytoplasmic transport by N-azolylacrylates: Structure-activity relationship and mechanism of action", Bioorganic & Medicinal Chemistry 16:9487-9497 (2008).
Walsh, Jr., M.D., et al., Exportin 1 Inhibition Attenuates Nuclear Factor-Kβ-Dependent Gene Expression, Shock, 29(2):160-166 (2008).
Wang et al., "Mathematical modeling in cancer drug discovery," Drug Discovery Today, 19(2):145-150 (2014).
Williams, P., et al., "Characterization of a CRM1-Dependent Nuclear Export Signal in the C Terminus of Herpes Simplex Virus Type 1 Tegument Protein UL47", Journal of Virology, 82(21):10946-10952 (2008).
Written Opinion of the International Searching Authority for International Application No. PCT/US2011/027328, "Nuclear Transport Modulators and Uses Thereof" dated Apr. 29, 2011, 8 pages.
Written Opinion of the International Searching Authority for International Application No. PCT/US2012/048319, "Hydrazide Containing Nuclear Transport Modulators and Uses Thereof" dated Nov. 9, 2012, 9 pages.
Written Opinion of the International Searching Authority for International Application No. PCT/US2012/048368, "Nuclear Transport Modulators and Uses Thereof" dated Sep. 21, 2012, 11 pages.
Yao, Y., et al., "The expression of CRM1 is associated with prognosis in human osteosarcoma", Oncology Reports, 21:229-235 (2009).
Yonemochi, "Physicochemical Properties for Amorphous Pharmaceuticals and their Stability," Cryobiol and Cryotechnol 51(1):25-30 (2005).
Zheng et al., "KPT-330 inhibitor of XPO1-mediated nuclear export has anti-proliferative activity in hepatocellular carcinoma," Cancer Chemother Pharmacol, 74:487-495 (2014).
Zimmerman, T.L. et al., "Nuclear Export of Retinoid X Receptor α in Response to Interleukin-1β-mediated Cell Signaling Roles for JNK and Ser260", The Journal of Biological Chemistry, 281(22):15434-15440 (2006).

* cited by examiner

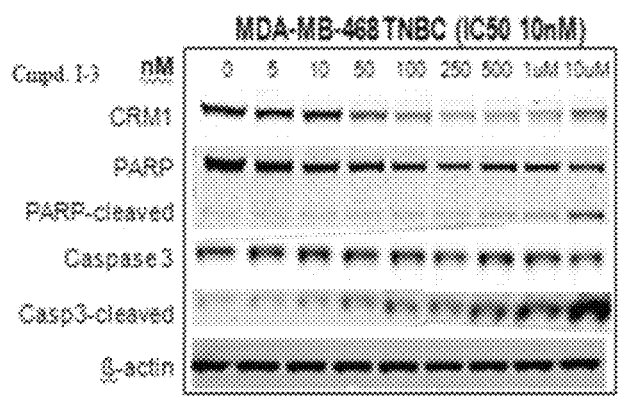
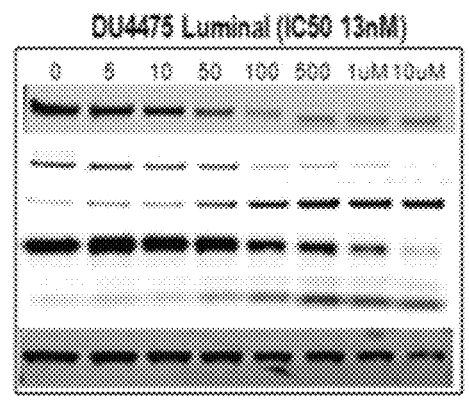
FIG. 2A     FIG. 2B
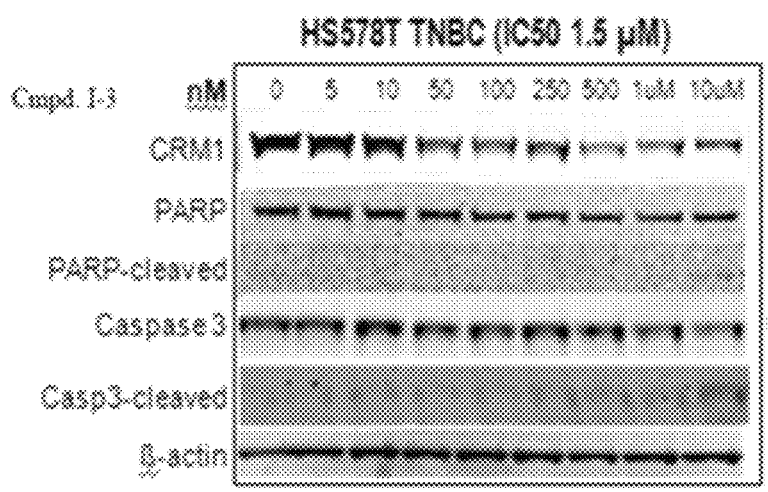
FIG. 2C

HYDRAZIDE CONTAINING NUCLEAR TRANSPORT MODULATORS AND USES THEREOF

RELATED APPLICATIONS

This application is a continuation of U.S. application Ser. No. 16/203,181, filed Nov. 28, 2018, which is a continuation of U.S. application Ser. No. 15/629,307, filed Jun. 21, 2017, which is a continuation of U.S. application Ser. No. 14/940,310, filed Nov. 13, 2015, (now U.S. Pat. No. 9,714,226), which is a continuation of U.S. application Ser. No. 14/735,853, filed Jun. 10, 2015 (now U.S. Pat. No. 9,206,158), which is a continuation of U.S. application Ser. No. 14/235,306, which is the U.S. National Stage Application of International Application No. PCT/US2012/048319, filed on Jul. 26, 2012 (now U.S. Pat. No. 9,079,865), published in English, which claims the benefit of U.S. Provisional Application No. 61/513,428, filed Jul. 29, 2011, U.S. Provisional Application No. 61/513,432, filed Jul. 29, 2011, U.S. Provisional Application No. 61/610,178, filed Mar. 13, 2012, U.S. Provisional Application No. 61/654,651, filed Jun. 1, 2012, and U.S. Provisional Application No. 61/653,588, filed May 31, 2012. The contents of the above applications are incorporated herein by reference in their entirety.

BACKGROUND OF THE INVENTION

Cells from most major human solid and hematologic malignancies exhibit abnormal cellular localization of a variety of oncogenic proteins, tumor suppressor proteins, and cell cycle regulators (Cronshaw et al. 2004, Falini et al 2006). For example, certain p53 mutations lead to localization in the cytoplasm rather than in the nucleus. This results in the loss of normal growth regulation, despite intact tumor suppressor function. In other tumors, wild-type p53 is sequestered in the cytoplasm or rapidly degraded, again leading to loss of its suppressor function. Restoration of appropriate nuclear localization of functional p53 protein can normalize some properties of neoplastic cells (Cai et al. 2008; Hoshino et al. 2008; Lain et al. 1999a; Lain et al. 1999b; Smart et al. 1999), can restore sensitivity of cancer cells to DNA damaging agents (Cai et al. 2008), and can lead to regression of established tumors (Sharpless & DePinho 2007, Xue et al. 2007). Similar data have been obtained for other tumor suppressor proteins such as forkhead (Turner and Sullivan 2008) and c-Abl (Vignari and Wang 2001). In addition, abnormal localization of several tumor suppressor and growth regulatory proteins may be involved in the pathogenesis of autoimmune diseases (Davis 2007, Nakahara 2009). CRM1 inhibition may provide particularly interesting utility in familial cancer syndromes (e.g., Li-Fraumeni Syndrome due to loss of one p53 allele, BRCA1 or 2 cancer syndromes), where specific tumor suppressor proteins (TSP) are deleted or dysfunctional and where increasing TSP levels by systemic (or local) administration of CRM1 inhibitors could help restore normal tumor suppressor function.

Specific proteins and RNAs are carried into and out of the nucleus by specialized transport molecules, which are classified as importins if they transport molecules into the nucleus, and exportins if they transport molecules out of the nucleus (Terry et al. 2007; Sorokin et al. 2007). Proteins that are transported into or out of the nucleus contain nuclear import/localization (NLS) or export (NES) sequences that allow them to interact with the relevant transporters. Chromosomal Region Maintenance 1 (Crm1 or CRM1), which is also called exportin-1 or Xpo1, is a major exportin.

Overexpression of Crm1 has been reported in several tumors, including human ovarian cancer (Noske et al. 2008), cervical cancer (van der Watt et al. 2009), pancreatic cancer (Huang et al. 2009), hepatocellular carcinoma (Pascale et al. 2005) and osteosarcoma (Yao et al. 2009) and is independently correlated with poor clinical outcomes in these tumor types.

Inhibition of Crm1 blocks the exodus of tumor suppressor proteins and/or growth regulators such as p53, c-Abl, p21, p27, pRB, BRCA1, IkB, ICp27, E2F4, KLF5, YAP1, ZAP, KLF5, HDAC4, HDAC5 or forkhead proteins (e.g., FOXO3a) from the nucleus that are associated with gene expression, cell proliferation, angiogenesis and epigenetics. Crm1 inhibitors have been shown to induce apoptosis in cancer cells even in the presence of activating oncogenic or growth stimulating signals, while sparing normal (untransformed) cells. Most studies of Crm1 inhibition have utilized the natural product Crm1 inhibitor Leptomycin B (LMB). LMB itself is highly toxic to neoplastic cells, but poorly tolerated with marked gastrointestinal toxicity in animals (Roberts et al. 1986) and humans (Newlands et al. 1996). Derivatization of LMB to improve drug-like properties leads to compounds that retain antitumor activity and are better tolerated in animal tumor models (Yang et al. 2007, Yang et al. 2008, Mutka et al. 2009). Therefore, nuclear export inhibitors could have beneficial effects in neoplastic and other proliferative disorders.

In addition to tumor suppressor proteins, Crm1 also exports several key proteins that are involved in many inflammatory processes. These include IkB, NF-kB, Cox-2, RXRα, Commdl, HIF1, HMGB1, FOXO, FOXP and others. The nuclear factor kappa B (NF-kB/rel) family of transcriptional activators, named for the discovery that it drives immunoglobulin kappa gene expression, regulate the mRNA expression of variety of genes involved in inflammation, proliferation, immunity and cell survival. Under basal conditions, a protein inhibitor of NF-kB, called IkB, binds to NF-kB in the nucleus and the complex IkB-NF-kB renders the NF-kB transcriptional function inactive. In response to inflammatory stimuli, IkB dissociates from the IkB-NF-kB complex, which releases NF-kB and unmasks its potent transcriptional activity. Many signals that activate NF-kB do so by targeting IkB for proteolysis (phosphorylation of IkB renders it "marked" for ubiquitination and then proteolysis). The nuclear IkBa-NF-kB complex can be exported to the cytoplasm by Crm1 where it dissociates and NF-kB can be reactivated. Ubiquitinated IkB may also dissociate from the NF-kB complex, restoring NF-kB transcriptional activity. Inhibition of Crm1 induced export in human neutrophils and macrophage like cells (U937) by LMB not only results in accumulation of transcriptionally inactive, nuclear IkBa-NF-kB complex but also prevents the initial activation of NF-kB even upon cell stimulation (Ghosh 2008, Huang 2000). In a different study, treatment with LMB inhibited IL-1β induced NF-kB DNA binding (the first step in NF-kB transcriptional activation), IL-8 expression and intercellular adhesion molecule expression in pulmonary microvascular endothelial cells (Walsh 2008). COMMD1 is another nuclear inhibitor of both NF-kB and hypoxia-inducible factor 1 (HIF1) transcriptional activity. Blocking the nuclear export of COMMD1 by inhibiting Crm1 results in increased inhibition of NF-kB and HIF1 transcriptional activity (Muller 2009).

Crm1 also mediates retinoid X receptor a (RXRα) transport. RXRα is highly expressed in the liver and plays a central role in regulating bile acid, cholesterol, fatty acid, steroid and xenobiotic metabolism and homeostasis. During liver inflammation, nuclear RXRα levels are significantly reduced, mainly due to inflammation-mediated nuclear export of RXRα by Crm1. LMB is able to prevent IL-1 induced cytoplasmic increase in RXRα levels in human liver derived cells (Zimmerman 2006).

The role of Crm1-mediated nuclear export in NF-kB, HIF-1 and RXRα signalling suggests that blocking nuclear export can be potentially beneficial in many inflammatory processes across multiple tissues and organs including the vasculature (vasculitis, arteritis, polymyalgia rheumatic, atherosclerosis), dermatologic (see below), rheumatologic (rheumatoid and related arthritis, psoriatic arthritis, spondyloarthropathies, crystal arthropathies, systemic lupus erythematosus, mixed connective tissue disease, myositis syndromes, dermatomyositis, inclusion body myositis, undifferentiated connective tissue disease, Sjogren's syndrome, scleroderma and overlap syndromes, etc.).

CRM1 inhibition affects gene expression by inhibiting/activating a series of transcription factors like ICp27, E2F4, KLF5, YAP1, and ZAP.

Crm1 inhibition has potential therapeutic effects across many dermatologic syndromes including inflammatory dermatoses (atopy, allergic dermatitis, chemical dermatitis, psoriasis), sun-damage (ultraviolet (UV) damage), and infections. CRM1 inhibition, best studied with LMB, showed minimal effects on normal keratinocytes, and exerted anti-inflammatory activity on keratinocytes subjected to UV, TNFα, or other inflammatory stimuli (Kobayashi & Shinkai 2005, Kannan & Jaiswal 2006). Crm1 inhibition also upregulates NRF2 (nuclear factor erythroid-related factor 2) activity, which protects keratinocytes (Schafer et al. 2010, Kannan & Jaiswal 2006) and other cell types (Wang et al. 2009) from oxidative damage. LMB induces apoptosis in keratinocytes infected with oncogenic human papillomavirus (HPV) strains such as HPV16, but not in uninfected keratinocytes (Jolly et al. 2009).

Crm1 also mediates the transport of key neuroprotectant proteins that may be useful in neurodegenerative diseases including Parkinson's disease (PD), Alzheimer's disease, and amyotrophic lateral sclerosis (ALS). For example, by (1) forcing nuclear retention of key neuroprotective regulators such as NRF2 (Wang 2009), FOXA2 (Kittappa et al. 2007), parking in neuronal cells, and/or (2) inhibiting NFκB transcriptional activity by sequestering IκB to the nucleus in glial cells, Crm1 inhibition could slow or prevent neuronal cell death found in these disorders. There is also evidence linking abnormal glial cell proliferation to abnormalities in CRM1 levels or CRM1 function (Shen 2008).

Intact nuclear export, primarily mediated through CRM1, is also required for the intact maturation of many viruses. Viruses where nuclear export, and/or CRM1 itself, has been implicated in their lifecycle include human immunodeficiency virus (HIV), adenovirus, simian retrovirus type 1, Borna disease virus, influenza (usual strains as well as H1N1 and avian H5N1 strains), hepatitis B (HBV) and C (HCV) viruses, human papillomavirus (HPV), respiratory syncytial virus (RSV), Dungee, Severe Acute Respiratory Syndrome coronavirus, yellow fever virus, West Nile virus, herpes simplex virus (HSV), cytomegalovirus (CMV), and Merkel cell polyomavirus (MCV). (Bhuvanakantham 2010, Cohen 2010, Whittaker 1998). It is anticipated that additional viral infections reliant on intact nuclear export will be uncovered in the future.

The HIV-1 Rev protein, which traffics through nucleolus and shuttles between the nucleus and cytoplasm, facilitates export of unspliced and singly spliced HIV transcripts containing Rev Response Elements (RRE) RNA by the CRM1 export pathway. Inhibition of Rev-mediated RNA transport using CRM1 inhibitors such as LMB or PKF050-638 can arrest the HIV-1 transcriptional process, inhibit the production of new HIV-1 virions, and thereby reduce HIV-1 levels (Pollard 1998, Daelemans 2002).

Dengue virus (DENV) is the causative agent of the common arthropod-borne viral disease, Dengue fever (DF), and its more severe and potentially deadly Dengue hemorrhagic fever (DHF). DHF appears to be the result of an over exuberant inflammatory response to DENV. NS5 is the largest and most conserved protein of DENV. CRM1 regulates the transport of NS5 from the nucleus to the cytoplasm, where most of the NS5 functions are mediated. Inhibition of CRM1-mediated export of NS5 results in altered kinetics of virus production and reduces induction of the inflammatory chemokine interleukin-8 (IL-8), presenting a new avenue for the treatment of diseases caused by DENV and other medically important flaviviruses including hepatitis C virus (Rawlinson 2009).

Other virus-encoded RNA-binding proteins that use CRM1 to exit the nucleus include the HSV type 1 tegument protein (VP13/14, or hUL47), human CMV protein pp65, the SARS Coronavirus ORF 3b Protein, and the RSV matrix (M) protein (Williams 2008, Sanchez 2007, Freundt 2009, Ghildyal 2009).

Interestingly, many of these viruses are associated with specific types of human cancer including hepatocellular carcinoma (HCC) due to chronic HBV or HCV infection, cervical cancer due to HPV, and Merkel cell carcinoma associated with MCV. CRM1 inhibitors could therefore have beneficial effects on both the viral infectious process as well as on the process of neoplastic transformation due to these viruses.

CRM1 controls the nuclear localization and therefore activity of multiple DNA metabolizing enzymes including histone deacetylases (HDAC), histone acetyltransferases (HAT), and histone methyltransferases (HMT). Suppression of cardiomyocyte hypertrophy with irreversible CRM1 inhibitors has been demonstrated and is believed to be linked to nuclear retention (and activation) of HDAC 5, an enzyme known to suppress a hypertrophic genetic program (Monovich et al. 2009). Thus, CRM1 inhibition may have beneficial effects in hypertrophic syndromes, including certain forms of congestive heart failure and hypertrophic cardiomyopathies.

CRM1 has also been linked to other disorders. Leber's disorder, a hereditary disorder characterized by degeneration of retinal ganglion cells and visual loss, is associated with inaction of the CRM1 switch (Gupta N 2008). There is also evidence linking neurodegenerative disorders to abnormalities in nuclear transport.

To date, however, small-molecule, drug-like Crm1 inhibitors for use in vitro and in vivo are uncommon.

SUMMARY OF THE INVENTION

The present invention relates to compounds, or pharmaceutically acceptable salts thereof, useful as nuclear transport modulators. The invention also provides pharmaceutically acceptable compositions comprising compounds of the present invention and methods of using said compounds and compositions in the treatment of various disorders, such as those associated with abnormal cellular responses triggered by improper nuclear transport.

In one embodiment of the invention, the compounds are represented by formula I

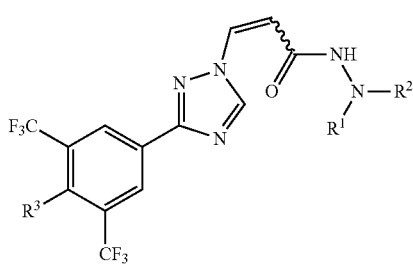

or a pharmaceutically acceptable salt thereof, wherein the values and alternative values for each variable are as defined and described herein.

Another embodiment of the invention is a composition comprising a compound of the invention, or a pharmaceutically acceptable salt thereof, and a pharmaceutically acceptable carrier.

Yet another embodiment of the invention is a method for treating a disorder associated with CRM1 activity, the method comprising administering to a subject in need thereof a therapeutically effective amount of a compound of the invention, or a pharmaceutically acceptable salt thereof, or a composition comprising a compound of the invention, or a pharmaceutically acceptable salt thereof.

Another embodiment of the invention is use of a compound of the invention for treating a disorder associated with CRM1 activity in a subject.

Another embodiment of the invention is use of a compound of the invention for the manufacture of a medicament for treating a disorder associated with CRM1 activity in a subject.

The nuclear transport modulators of the present invention, and pharmaceutically acceptable salts and/or compositions thereof, provide excellent in vivo exposure as measured by AUC in mouse, rat, dog and monkey, while exhibiting low levels of brain penetration. Therefore, compounds of the present invention, and pharmaceutically acceptable salts and/or compositions thereof, are useful for treating a variety of diseases, disorders or conditions, associated with abnormal cellular responses triggered by improper nuclear transport, such as those diseases, disorders, or conditions described herein. Compounds provided by this invention are also useful for the study of nuclear transport modulation in biological and pathological phenomena; the study of intracellular signal transduction pathways mediated by kinases; and the comparative evaluation of nuclear transport modulators.

BRIEF DESCRIPTION OF THE FIGURES

FIG. 2A is a Western blot image showing the effect of increasing concentrations of Compound 1-3 on CRM1 and apoptosis marker proteins in MDA-MB-468 TNBC cells.

FIG. 2B is a Western blot image showing the effect of increasing concentrations of Compound I-3 on CRM1 and apoptosis marker proteins in DU4475 luminal BC cells.

FIG. 2C is a Western blot image showing the effect of increasing concentrations of Compound I-3 on CRM1 and apoptosis marker proteins in HS578T TNBC cells.

DETAILED DESCRIPTION

Figure 1:
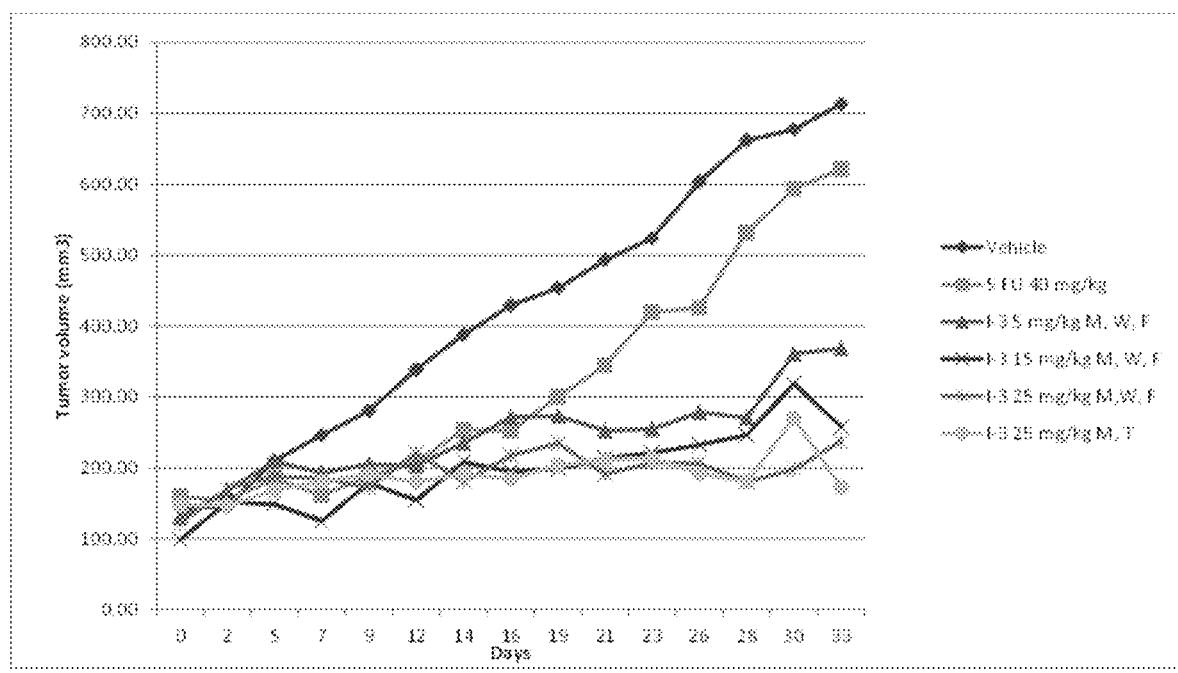
FIG. 1 is a graph of tumor volume as a function of time and shows the effect of Compound 1-3 on tumor volume in a mouse xenograft model of Triple Negative Breast Cancer (TNBC).

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

Compounds of the Invention

One embodiment of the invention is compounds represented by formula I:

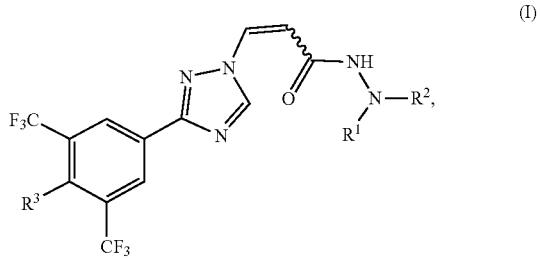

or a pharmaceutically acceptable salt thereof, wherein:

$R^1$ is selected from hydrogen and methyl;

$R^2$ is selected from pyridin-2-yl, pyridin-3-yl, pyridin-4-yl, pyrazin-2-yl, and quinoxalin-2-yl, pyrimidin-4-yl, 1,1-dioxotetrahydrothiophen-3-yl and cyclopropyl, wherein $R^2$ is optionally substituted with one or more independent substituents selected from methyl and halogen; or R¹ and R² are taken together with their intervening atoms to form 4-hydroxypiperidin-1-yl, pyrrolidin-1-yl, azepan-1-yl, 4-benzylpiperazin-1-yl, 4-ethylpiperazin-1-yl, 3-hydroxyazetidin-1-yl, or morpholin-4-yl;

R³ is selected from hydrogen and halo; and

∿ represents a single bond wherein a carbon-carbon double bond bound thereto is in an (E)- or (Z)-configuration.

As described generally above, R is selected from hydrogen and methyl. In some embodiments, R is hydrogen. In some embodiments, R is methyl.

As described generally above, R² is selected from pyridin-2-yl, pyridin-3-yl, pyridin-4-yl, pyrazin-2-yl, quinoxalin-2-yl, pyrimidin-4-yl, 1,1-dioxotetrahydrothiophen-3-yl and cyclopropyl, wherein R² is optionally substituted with one or more independent substituents selected from methyl and halogen. In some embodiments of formula I, R is pyridin-2-yl. In some embodiments of formula I, R² is pyridin-3-yl. In some embodiments of formula I, R² is pyridin-4-yl. In some embodiments of formula I, R² is pyrazin-2-yl. In some embodiments of formula I, R² is pyrimidin-4-yl. In some embodiments of formula I, R² is quinoxalin-2-yl. In some embodiments of formula I, R² is selected from pyridin-2-yl, pyridin-3-yl and pyridin-4-yl. In some embodiments of formula I, R² is selected from pyridin-2-yl, pyridin-3-yl, pyridin-4-yl, pyrazin-2-yl and pyrimidin-4-yl. In some embodiments of formula I, R² is selected from pyridin-2-yl, pyridin-4-yl, pyrazin-2-yl and pyrimidin-4-yl.

In some embodiments, R² is selected from:

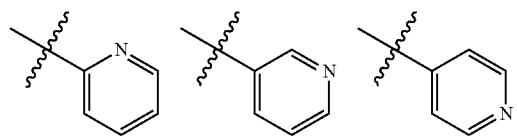

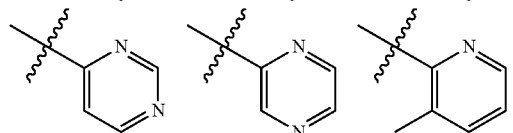

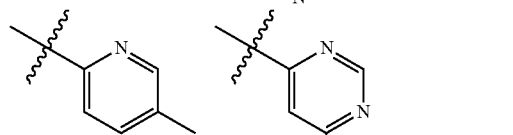

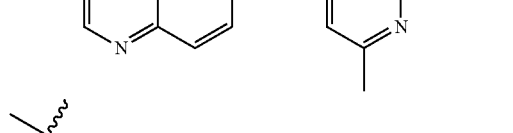

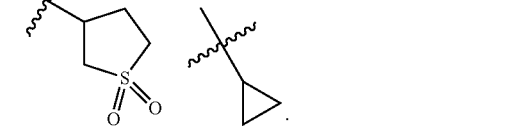

In some embodiments of formula I, R² is optionally substituted with a single substituent selected from methyl and chloro. In some embodiments of formula I, R² is optionally substituted with a methyl group. In some embodiments of formula I, R² is optionally substituted with a chloro group. In some embodiments, R² is selected from:

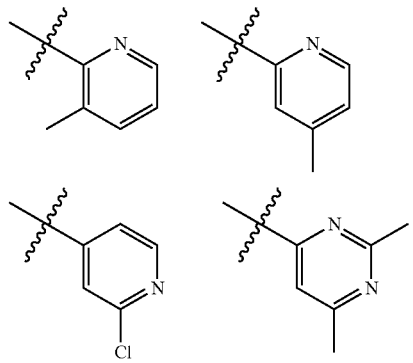

In some embodiments, R² is selected from:

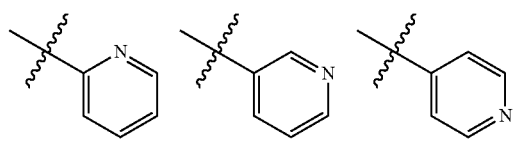

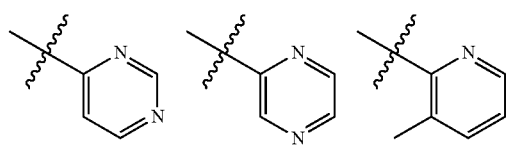

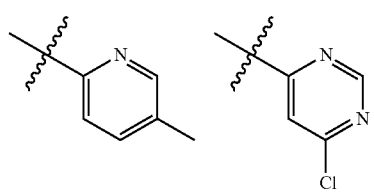

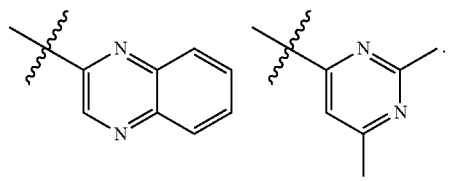

In some embodiments, R² is selected from:

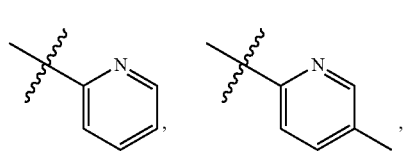

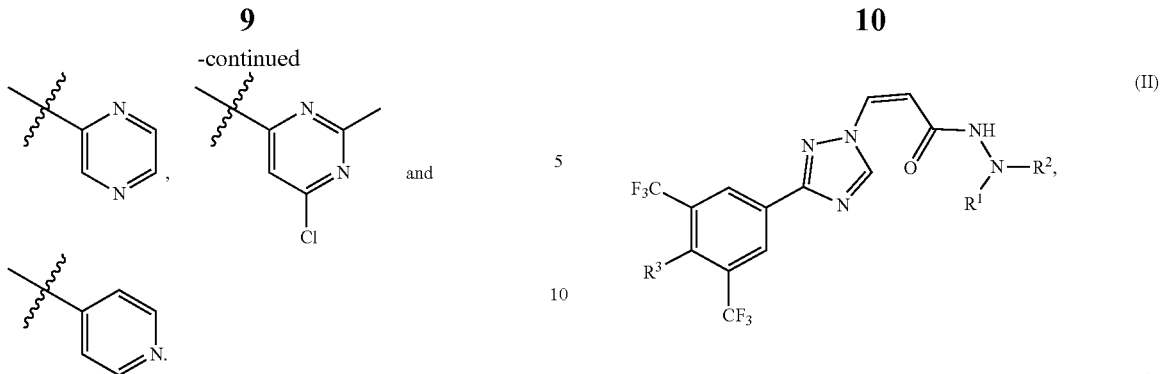

In some embodiments of formula I, $R^1$ and $R^2$ are taken together with their intervening atoms to form 4-hydroxypiperidin-1-yl, pyrrolidin-1-yl, azepan-1-yl, 4-benzylpiperazin-1-yl, 4-ethylpiperazin-1-yl, 3-hydroxyazetidin-1-yl, or morpholin-4-yl. In some embodiments of formula I, $R^1$ and $R^2$ are taken together with their intervening atoms to form 4-hydroxypiperidin-1-yl.

As described generally above, $R^3$ is selected from hydrogen and halogen. In some embodiments, $R^3$ is hydrogen. In some embodiments, $R^3$ is halogen (e.g., chloro, bromo, iodo or fluoro). In some such embodiments, $R^3$ is chloro.

As described generally above, the carbon-carbon double bond in between the triazole moiety and the carbonyl moiety is in an (E)-configuration or a (Z)-configuration. In some embodiments, that double bond is in a (E)-configuration. In some embodiments, that double bond is in a (Z)-configuration and the compound is represented by formula II or a pharmaceutically acceptable salt thereof, wherein $R^1$, $R^2$ and $R^3$ are as defined above and described herein.

A further embodiment of the invention is a compound represented by formula II, or a pharmaceutically acceptable salt thereof, wherein the values and alternative values for the variables are as defined above for a compound of formula I.

In a first aspect of this further embodiment, $R^1$ is as defined above; and $R^2$ is selected from pyridin-2-yl, pyridin-4-yl, pyrazin-2-yl and pyrimidin-4-yl, wherein $R^2$ is optionally substituted with a single substituent selected from methyl and chloro; or $R^1$ and $R^2$ are taken together with their intervening atoms to form 4-hydroxypiperidin-1-yl.

In a specific aspect of the first aspect $R^3$ is hydrogen. The values and alternative values for the remaining variables are as described above for a compound of formula I, or in the further embodiment, or first aspect thereof.

Exemplary compounds of formula I are set forth in Table 1.

TABLE 1

Exemplary compound of formula I.

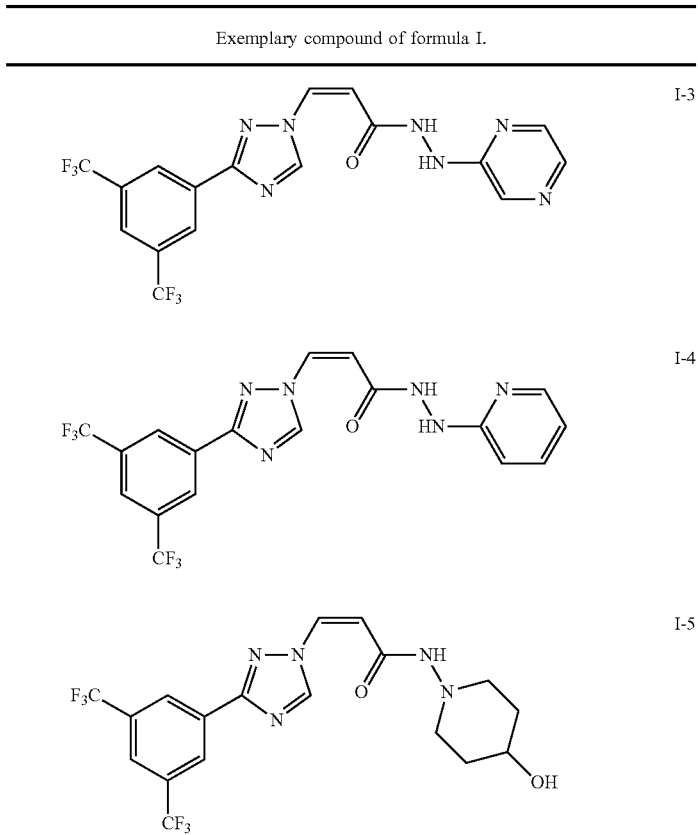

TABLE 1-continued
Exemplary compound of formula I.
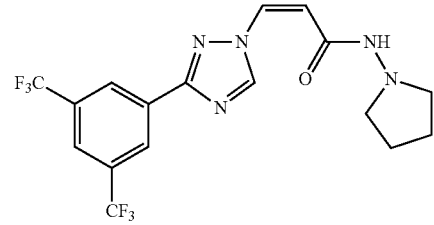 [SMILES: O=C(/C=C\n1cnc(-c2cc(C(F)(F)F)cc(C(F)(F)F)c2)n1)NN1CCCC1]
I-6
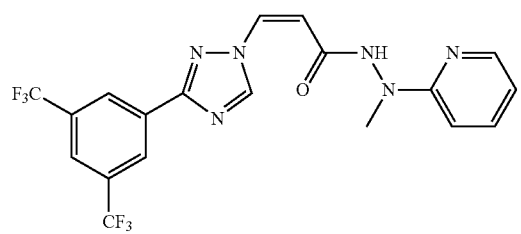 [SMILES: CN(NC(=O)/C=C\n1cnc(-c2cc(C(F)(F)F)cc(C(F)(F)F)c2)n1)c1ccccn1]
I-7
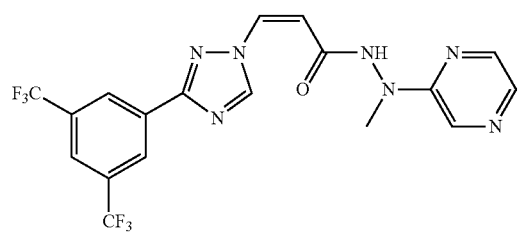 [SMILES: CN(NC(=O)/C=C\n1cnc(-c2cc(C(F)(F)F)cc(C(F)(F)F)c2)n1)c1cnccn1]
I-8
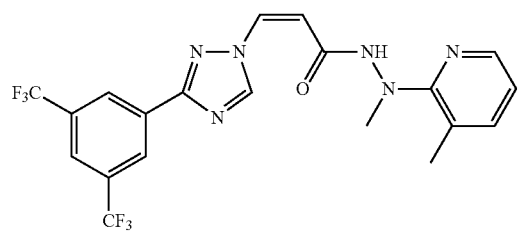 [SMILES: Cc1cccnc1N(C)NC(=O)/C=C\n1cnc(-c2cc(C(F)(F)F)cc(C(F)(F)F)c2)n1]
I-9
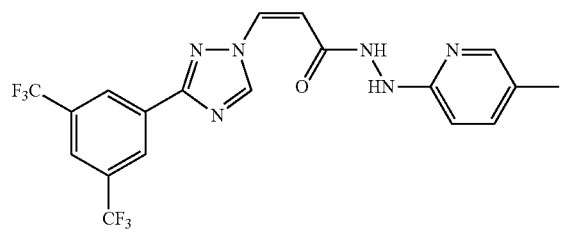 [SMILES: Cc1ccc(NNC(=O)/C=C\n2cnc(-c3cc(C(F)(F)F)cc(C(F)(F)F)c3)n2)nc1]
I-10
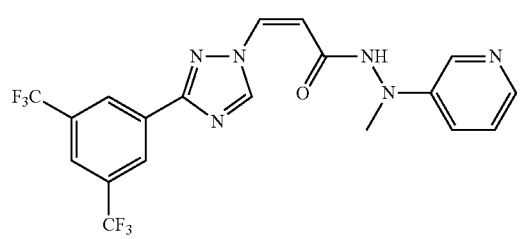 [SMILES: CN(NC(=O)/C=C\n1cnc(-c2cc(C(F)(F)F)cc(C(F)(F)F)c2)n1)c1cccnc1]
I-11

TABLE 1-continued
Exemplary compound of formula I.
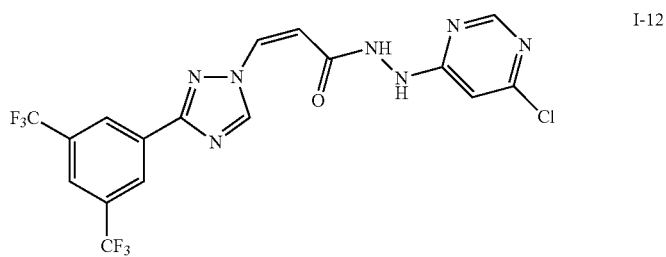
I-12
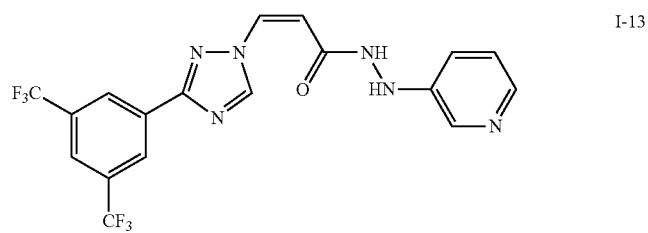
I-13
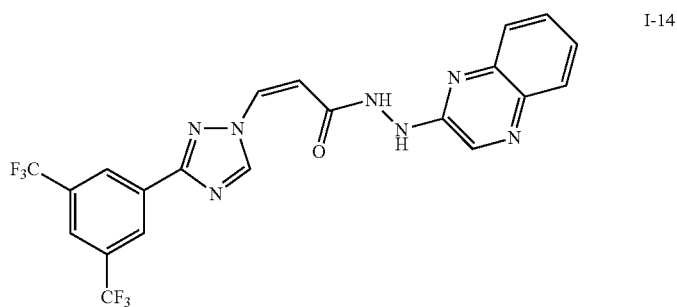
I-14
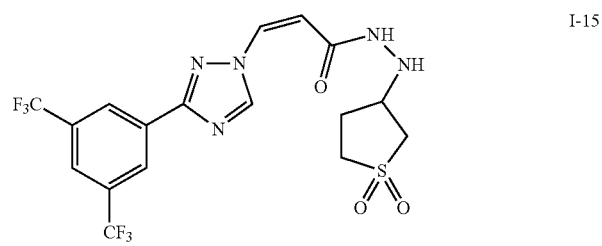
I-15
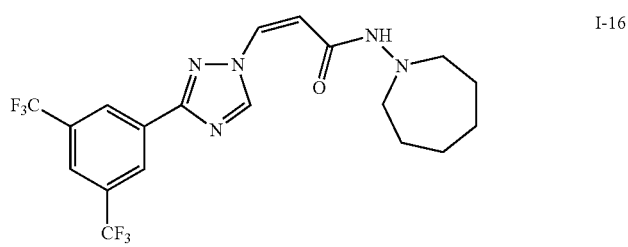
I-16
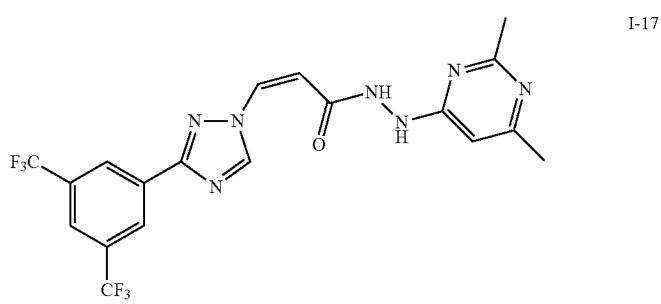
I-17

TABLE 1-continued
Exemplary compound of formula I.
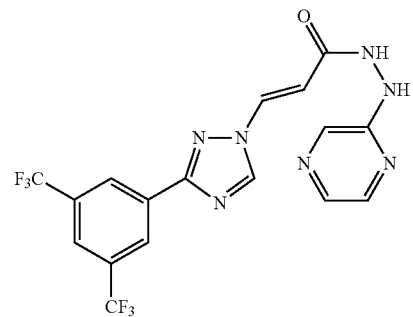
I-18
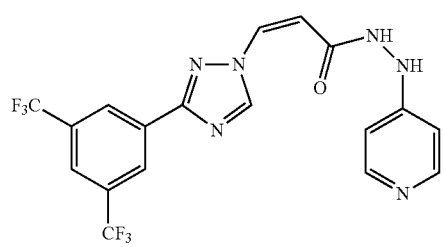 [SMILES: O=C(/C=C\n1cnc(-c2cc(C(F)(F)F)cc(C(F)(F)F)c2)n1)NNc1ccncc1]
I-19
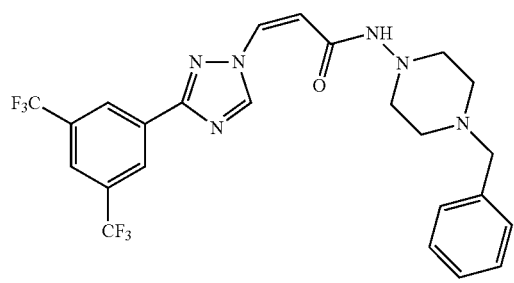 [SMILES: O=C(/C=C\n1cnc(-c2cc(C(F)(F)F)cc(C(F)(F)F)c2)n1)NN1CCN(Cc2ccccc2)CC1]
I-20
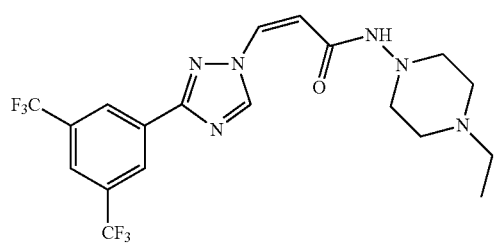 [SMILES: CCN1CCN(NC(=O)/C=C\n2cnc(-c3cc(C(F)(F)F)cc(C(F)(F)F)c3)n2)CC1]
I-21
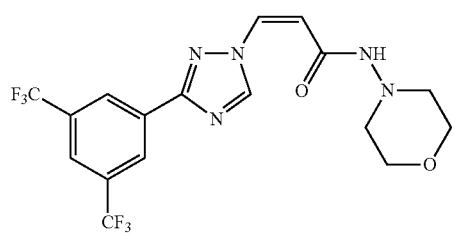
I-22
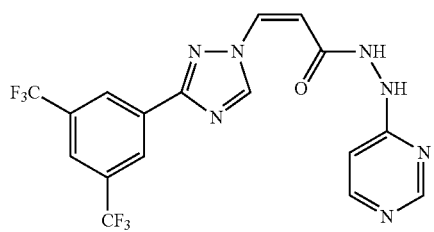
I-23

TABLE 1-continued

Exemplary compound of formula I.

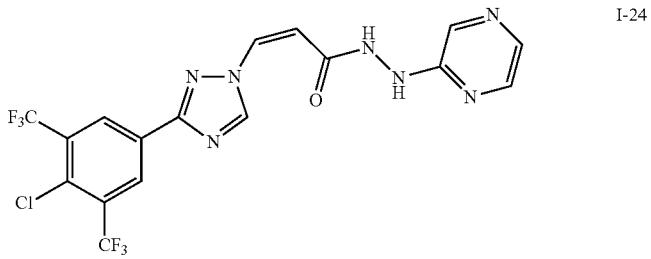

I-24

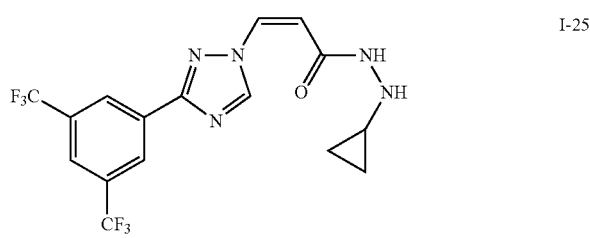

I-25

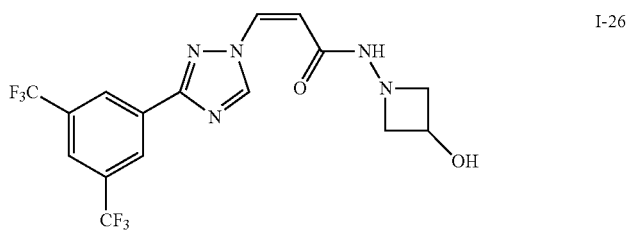

I-26

In some embodiments, the compound of the invention is selected from any one of compounds I-3 to I-26. In one aspect of these embodiments, the compound is selected from compounds I-3, I-4, I-5, I-7, I-8, I-10, I-12, I-18, I-19 and I-24. In a more specific aspect, the compound of the invention is selected from I-3 and I-4.

Pharmacokinetics (PK) play an increasing role in drug discovery and development. Pharmacokinetics is the quantitative study of the time course of drug absorption, distribution, metabolism and/or excretion. When a drug is administered, it distributes rapidly from its administration site into the systemic blood circulation. One measure of the extent of a therapeutic agent's distribution is the area under the plasma concentration-time curve (AUC), calculated to the last measured concentration ($AUC_t$) and extrapolated to infinity ($AUC_{Inf}$). AUC is thus a useful metric to quantitate drug exposure.

Generally, the higher the exposure of a therapeutic agent, the greater the effects of the agent. However, high exposure of a therapeutic agent may have deleterious effects on certain tissues such as the brain. While the blood-brain barrier (BBB), a protective network consisting of tight junctions between endothelial cells, restricts the diffusion of hydrophilic and/or large molecules, drugs with high AUC are still capable of penetrating the BBB and/or cerebrospinal fluid. Such penetration is often undesirable and can lead to unwanted side effects. Current drug discovery efforts are aimed, in part, at striking a balance between maximizing drug exposure (e.g., AUC), while minimizing brain penetration.

The brain to plasma (B:P) ratio is one method of quantifying the relative distribution of a therapeutic agent in brain tissue to that in circulation and, as such, provides one indication of the brain penetration of a given therapeutic agent. A high brain to plasma ratio is preferred when targeting diseases localized in the central nervous system (CNS), including the brain and the cerebrospinal fluid. However, a lower brain to plasma ratio is generally preferable for non-CNS therapeutic agents to minimize brain penetration and avoid potential side effects caused by unwanted accumulation of the therapeutic agents in the brain and CNS tissue.

As set forth in more detail in the Exemplification, the compounds of the present invention display a higher AUC and/or a lower B:P as compared to other nuclear transport inhibitors, such as those disclosed in co-owned U.S. patent application Ser. No. 13/041,377, filed Mar. 5, 2011 and published as US 2009/0275607 on Nov. 10, 2011. In some embodiments of the present invention, the compound of formula I has a nuclear export activity of less than about 1 μM, an $AUC_{Inf}$ of greater than about 3300 (e.g., greater than about 3500), and a B:P ratio of less than about 2.5 when dosed in a mouse at 10 mg/kg po.

Synthetic Methods of the Invention

In accordance with the present invention, there is provided a method of preparing (Z)-olefin derivatives of a compound of formula Z useful in preparing compound of the invention (e.g., precursors to the compounds of the invention):

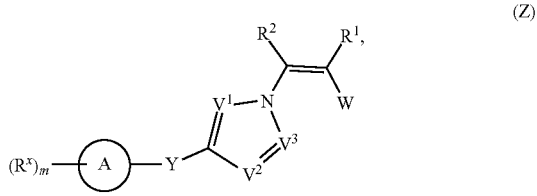

or a pharmaceutically acceptable salt thereof, wherein:

Ring A is an optionally substituted ring selected from phenyl, an 8-10-membered bicyclic aryl ring, a 5-6-membered monocyclic heteroaryl ring having 1-4 heteroatoms independently selected from nitrogen, oxygen, and sulfur, and an 8-10-membered bicyclic heteroaryl ring having 1-4 heteroatoms independently selected from nitrogen, oxygen, and sulfur;

Y is a covalent bond or -L-;

L is a bivalent $C_{1-8}$ saturated or unsaturated, straight or branched, hydrocarbon radical, wherein one or two methylene units of L is optionally replaced by —NR—, —N(R)C(O)—, —C(O)N(R)—, —O—, —C(O)—, —OC(O)—, —C(O)O—, —S—, —SO—, —SO$_2$—, —C(S)—, —C(NOR)— or —C(NR)—;

each R is independently hydrogen or an optionally substituted group selected from $C_{1-6}$ aliphatic, phenyl, a 4-7-membered saturated or partially unsaturated carbocyclic ring, a 4-7-membered saturated or partially unsaturated heterocyclic ring having 1-2 heteroatoms independently selected from nitrogen, oxygen, and sulfur, a 5-6-membered monocyclic heteroaryl ring having 1-4 heteroatoms independently selected from nitrogen, oxygen, and sulfur, an 8-10-membered bicyclic aryl ring, and an 8-10-membered bicyclic heteroaryl ring having 1-4 heteroatoms independently selected from nitrogen, oxygen, and sulfur; or two R groups on the same nitrogen are taken together with the nitrogen atom to which they are attached to form a 4-7-membered saturated or partially unsaturated heterocyclic ring having 1-4 heteroatoms independently selected from nitrogen, oxygen, and sulfur, or a 5-6-membered heteroaryl ring having 1-4 heteroatoms independently selected from nitrogen, oxygen, and sulfur;

each of $V^1$, $V^2$ and $V^3$ is independently C(R$^y$) or N;

each R$^x$ and R$^y$ is independently selected from —R, halogen, —OR, —SR, —N(R)$_2$, —CN, —NO$_2$, —N$_3$, —SOR, —SO$_2$R, —SO$_2$NR, —C(O)R, —CO$_2$R, —C(O)OR, —C(O)N(R)$_2$, —NRC(O)R, —OC(O)R, —OC(O)N(R)$_2$, —NRC(O)OR, —NRC(O)NR$_2$ and —NRSO$_2$R;

each R$^1$ and R$^2$ is independently hydrogen, deuterium, tritium or halogen; W is —CN, haloalkyl, —NO$_2$ or —C(=Z)R$^3$;

Z is O, S, or NR;

R$^3$ is selected from hydrogen, —R, OR, —SR and —N(R$^4$)$_2$;

each R$^4$ is independently —R; or two R$^4$ on the same nitrogen are taken together with the nitrogen atom to which they are attached to form a 4-7-membered saturated or partially unsaturated heterocyclic ring having 1-4 heteroatoms independently selected from nitrogen, oxygen, and sulfur, or a 5-6-membered heteroaryl ring having 1-4 heteroatoms independently selected from nitrogen, oxygen, and sulfur, wherein the ring thereby formed is optionally substituted with —(R$^5$)$_n$;

each R$^5$ is independently selected from —R, halogen, —OR, —SR, —N(R)$_2$, —CN, —NO$_2$, —N$_3$, —SOR, —SO$_2$R, —SO$_2$NR, —C(O)R, —CO$_2$R, —C(O)OR, —C(O)N(R)$_2$, —NRC(O)R, —OC(O)R, —OC(O)N(R)$_2$, —NRC(O)OR, —NRC(O)NR$_2$ and —NRSO$_2$R; and each m and n is independently an integer selected from 0, 1, 2, 3 and 4.

Compounds of formula Z have been described, for example, in U.S. Ser. No. 13/041,377, filed Mar. 5, 2011, and in U.S. Provisional Application Nos. 61/513,428, filed Jul. 29, 2011, and 61/653,588, filed Jun. 1, 2012. Compounds of formula Z are generally synthesized as a mixture of (E)- and (Z)-olefin isomers, which must be separated. The separation of (E)- and (Z)-olefin isomers requires extensive chromatography and results in a loss of 50% of the advanced intermediate A, as the undesired isomer cannot typically be converted to the desired isomer. A 50% yield is inefficient and costly at any step of a synthesis, but such unacceptable yields are even more problematic at the end of a multi-step synthesis. It has now been surprisingly discovered that the use of sterically hindered bases in a 1,4-nucleophilic addition can effect (Z)-selectivity of the reaction, thereby providing the cis-olefin isomer as the major or exclusive product. Accordingly, the present invention provides a (Z)-selective synthesis of compounds of formula Z, and methods of preparing synthetic intermediates useful for preparing compounds of formula Z. A key step in the synthesis of compounds of formula Z is depicted in Scheme I.

In certain embodiments, the compounds of formula Z are prepared according to Scheme I, set forth below:

Scheme I

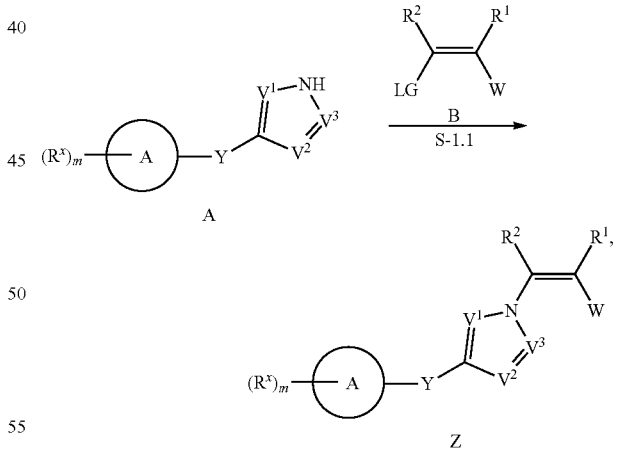

wherein LG is a leaving group and each of Ring A, Y, $V^1$, $V^2$, $V^3$, R$^x$, R$^1$, R$^2$, W and m is as defined above with respect to a compound of formula Z and described in embodiments herein.

In some embodiments of step S-1.1, intermediate A is coupled with intermediate B via a 1,4-nucleophilic addition/elimination reaction. In some embodiments of step S-1.1, LG is a suitable leaving group. In some such embodiments of step S-1.1, LG is a halogen. In some embodiments, LG is iodo. In some embodiments of step S-1.1, LG is bromo. In some embodiments of step 5-1.1, LG is a sulfonate. In some such embodiments, LG is methanesulfonate (mesylate).

In some embodiments of step S-1.1, intermediate A is coupled with intermediate B in the presence of a sterically-hindered nucleophilic base. One of ordinary skill will be able to select a suitable sterically-hindered base. Suitable sterically-hindered nucleophilic bases for use in the present invention include 1,8-diazabicyclo[5.4.0]undec-7-ene (DBU), 1,5-diazabicyclo[4.3.0]non-5-ene (DBN), 1,4-diazabicyclo(2.2.2)octane (DABCO), N,N-dicyclohexylmethylamine, 2,6-di-tert-butyl-4-methylpyridine, quinuclidine, 1,2,2,6,6-pentamethylpiperidine (PMP), 7-methyl-1,5,7-triazabicyclo(4.4.0)dec-5-ene (MTBD), triphenylphosphine, tri-tert-butylphosphine and tricyclohexylphosphine.

In certain embodiments, the compounds of formula Y are prepared according to Scheme II, set forth below:

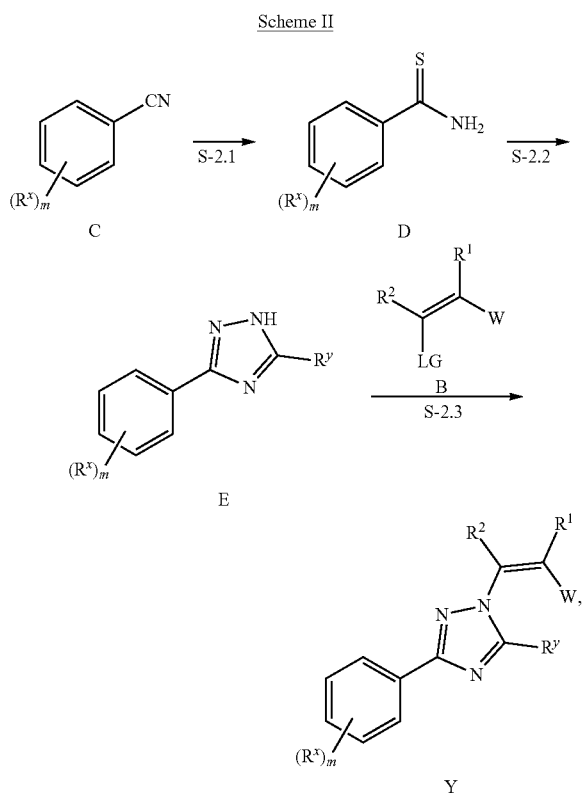

wherein LG is a leaving group and each of $R^x$, $R^y$, $R^1$, $R^2$, W and m is as defined above with respect to a compound of formula Z and described in embodiments herein.

In some embodiments of step S-2.1, intermediate C is reacted with a thiolate salt to provide intermediate D. In some embodiments of step S-2.1, the thiolate salt is sodium thiolate. In some embodiments of step S-2.1, the thiolate salt is potassium thiolate.

At step S-2.2, intermediate D is reacted with a hydrazine equivalent to provide intermediate E.

At step S-2.3, intermediate E is coupled with intermediate B to provide a compound of formula Y. In some embodiments of step S-2.3, LG is a suitable leaving group. In some such embodiments of step S-2.3, LG is a halogen. In some embodiments, LG is iodo. In some embodiments of step S-2.3, LG is bromo. In some embodiments of step S-2.3, LG is a sulfonate. In some such embodiments, LG is methanesulfonate (mesylate).

In some embodiments of step S-2.3, intermediate E is coupled with intermediate B in the presence of a sterically-hindered nucleophilic base. One of ordinary skill will be able to select a suitable sterically-hindered base. Suitable sterically-hindered nucleophilic bases for use in the present invention include 1,8-diazabicyclo[5.4.0]undec-7-ene (DBU), 1,5-diazabicyclo[4.3.0]non-5-ene (DBN), 1,4-diazabicyclo(2.2.2)octane (DABCO), N,N-dicyclohexylmethylamine, 2,6-di-tert-butyl-4-methylpyridine, quinuclidine, 1,2,2,6,6-pentamethylpiperidine (PMP), 7-methyl-1,5,7-triazabicyclo(4.4.0)dec-5-ene (MTBD), triphenylphosphine, tri-tert-butylphosphine and tricyclohexylphosphine.

According to one aspect, the present invention provides a method for providing a compound of formula Z:

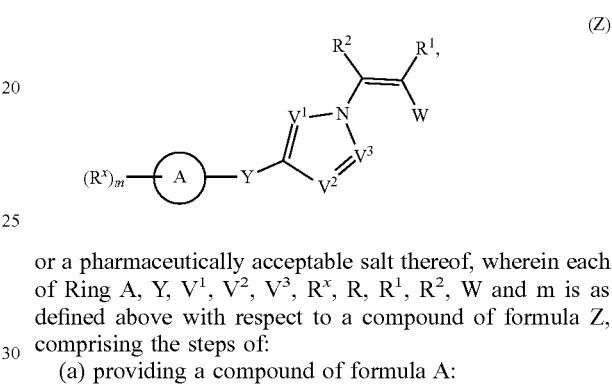

or a pharmaceutically acceptable salt thereof, wherein each of Ring A, Y, $V^1$, $V^2$, $V^3$, $R^x$, R, $R^1$, $R^2$, W and m is as defined above with respect to a compound of formula Z, comprising the steps of:

(a) providing a compound of formula A:

wherein each of Ring A, $R^x$, Y, $V^1$, $V^2$, $V^3$ and m is as defined above for a compound of formula Z; and (b) reacting said compound of formula A with an olefin of formula B:

(B)

$$\underset{LG}{\overset{R^2}{\underset{}{\rule{1em}{0pt}}}} \overset{R^1}{=} W$$

wherein:
LG is halogen, —OSO$_2$R or —OSO$_2$CF$_3$; and
each of R, W, $R^1$ and $R^2$ is as defined above for a compound of formula Z;
in the presence of a sterically-hindered nucleophilic base to form a compound of formula Z.

As described above, a compound of formula A is coupled with intermediate B via a 1,4-nucleophilic addition/elimination reaction. In some embodiments, a compound of formula A is coupled with intermediate B in the presence of a sterically-hindered nucleophilic base. Suitable sterically-hindered bases include tertiary amine bases. In some embodiments, a suitable sterically-hindered bases includes sterically-hindered secondary amine bases. In some embodiments, the sterically-hindered nucleophilic base is selected from 1,8-diazabicyclo[5.4.0]undec-7-ene (DBU), 1,5-diazabicyclo[4.3.0]non-5-ene (DBN), 1,4-diazabicyclo(2.2.2)octane (DABCO), N,N-dicyclohexylmethylamine, 2,6-di-tert-butyl-4-methylpyridine, quinuclidine, 1,2,2,6,6-pentamethylpiperidine (PMP), 7-methyl-1,5,7-triazabicyclo(4.4.0)dec-5-ene (MTBD), triphenylphosphine, tri-tert-butylphosphine and tricyclohexylphosphine. In some embodiments, the sterically-hindered nucleophilic base is 1,4-diazabicyclo(2.2.2)octane (DABCO). In some embodiments, the sterically-hindered nucleophilic base is 1,8-diazabicyclo[5.4.0]undec-7-ene (DBU).

In some embodiments, the sterically-hindered nucleophilic base is a phosphine. In some such embodiments, the sterically-hindered nucleophilic base is triphenylphosphine.

In some embodiments, step (b) above is performed at a temperature range of about 0° C. to about 100° C. In some embodiments, step (b) is performed at a temperature of about 0° C. In some embodiments, step (b) is performed at a temperature of about 25° C. In some embodiments, step (b) is performed at a temperature of about 50° C. In some embodiments, step (b) is performed at a temperature of about 100° C.

One of ordinary skill will recognize that the 1,4-nucleophilic addition/elimination reaction of a compound of formula A and intermediate B requires the use of a polar, aprotic organic solvent. Suitable polar, aprotic organic solvents include ethers such as dioxane, tetrahydrofuran and methyl tert-butyl ether (MTBE), and amides such as dimethylformamide (DMF) and dimethylacetamide (DMA). One of ordinary skill is capable of selecting the appropriate solvent for the desired reaction temperature.

According to another aspect, the present invention provides a method of providing a compound of formula Y:

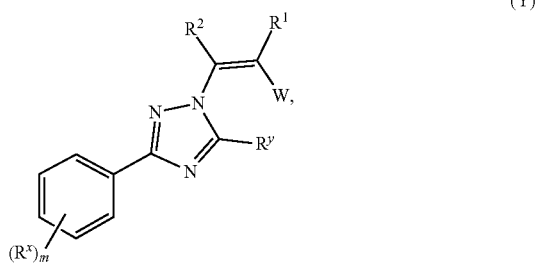

(Y)

or a pharmaceutically acceptable salt thereof, wherein each of R, $R^x$, $R^y$, $R^1$, $R^2$, W and m is as defined above with respect to a compound of formula Z, comprising the steps of:

(a) providing a compound of formula E:

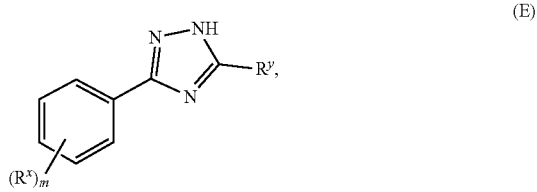

(E)

wherein each of $R^x$, $R^y$ and m is as defined above for a compound of formula Y; and (b) reacting said compound of formula E with an olefin of formula B:

(B)

wherein:

LG is halogen, —OSO$_2$R or —OSO$_2$CF$_3$; and each of R, W, $R^1$ and $R^2$ is as defined above for a compound of formula Y, in the presence of a sterically-hindered nucleophilic base to form a compound of formula Y.

As described above, a compound of formula E is coupled with intermediate B via a 1,4-nucleophilic addition/elimination reaction. In some embodiments, a compound of formula E is coupled with intermediate B in the presence of a sterically-hindered nucleophilic base. Suitable sterically-hindered bases include tertiary amine bases. In some embodiments, a suitable sterically-hindered bases includes sterically-hindered secondary amine bases. In some embodiments, the sterically-hindered nucleophilic base is selected from 1,8-diazabicyclo[5.4.0]undec-7-ene (DBU), 1,5-diazabicyclo[4.3.0]non-5-ene (DBN), 1,4-diazabicyclo(2.2.2)octane (DABCO), N,N-dicyclohexylmethylamine, 2,6-di-tert-butyl-4-methylpyridine, quinuclidine, 1,2,2,6,6-pentamethylpiperidine (PMP), 7-methyl-1,5,7-triazabicyclo(4.4.0)dec-5-ene (MTBD), triphenylphosphine, tri-tert-butylphosphine and tricyclohexylphosphine. In some embodiments, the sterically-hindered nucleophilic base is 1,4-diazabicyclo(2.2.2)octane (DABCO). In some embodiments, the sterically-hindered nucleophilic base is 1,8-diazabicyclo[5.4.0]undec-7-ene (DBU).

In some embodiments, the sterically-hindered nucleophilic base is a phosphine. In some such embodiments, the sterically-hindered nucleophilic base is triphenylphosphine.

In some embodiments, step (b) above is performed at a temperature range of about 0° C. to about 100° C. In some embodiments, step (b) is performed at a temperature of about 0° C. In some embodiments, step (b) is performed at a temperature of about 25° C. In some embodiments, step (b) is performed at a temperature of about 50° C. In some embodiments, step (b) is performed at a temperature of about 100° C.

One of ordinary skill will recognize that the 1,4-nucleophilic addition/elimination reaction of a compound of formula E and intermediate B requires the use of a polar, aprotic organic solvent. Suitable polar, aprotic organic solvents include ethers such as dioxane, tetrahydrofuran and methyl tert-butyl ether (MTBE), and amides such as dimethylformamide (DMF) and dimethylacetamide (DMA). One of ordinary skill is capable of selecting the appropriate solvent for the desired reaction temperature.

In some embodiments of a compound of formula Y, W is —CN. In some embodiments, W is haloalkyl. In some such embodiments, W is —CF$_3$. In some embodiments, W is —NO$_2$.

In some embodiments, W is —C(=Z)$R^3$. In some such embodiments, Z is O. In some embodiments, W is —C(O)$R^3$, wherein $R^3$ is selected from —OR, —SR or —N($R^4$)$_2$. In some embodiments, W is —C(O)OR. In some embodiments, W is —C(O)OR, wherein R is selected from methyl, ethyl, isopropyl, butyl, tert-butyl and sec-butyl. In some embodiments, W is —C(O)OCH$_3$. In some embodiments, W is —C(O)OCH$_2$CH$_3$. In some embodiments, W is —C(O)OCH(CH$_3$)$_2$.

In some embodiments, W is —C(O)N(R$^4$)$_2$. In some embodiments, W is —(O)NH(R$^4$). In some embodiments, W is —C(O)NH$_2$. In some embodiments, W is —C(=O)N(R$^4$)$_2$, wherein both R$^4$ groups are taken together with the nitrogen atom to which they are attached to form a 4-7 membered saturated heterocyclic ring having 1-4 heteroatoms independently selected from nitrogen, oxygen, and sulfur, wherein the ring thereby formed is optionally substituted with —(R$^5$)$_n$. In some embodiments, W is —C(O)N(R$^4$)$_2$, wherein both R$^4$ groups are taken together with the nitrogen atom to which they are attached to form a 4-7 membered saturated heterocyclic ring having 1-3 heteroatoms independently selected from nitrogen, oxygen, and sulfur, wherein the ring thereby formed is optionally substituted with —(R$^5$)$_n$. In some embodiments, W is —C(O)N(R$^4$)$_2$, wherein both R$^4$ groups are taken together with the nitrogen atom to which they are attached to form a 4-7 membered saturated heterocyclic ring having 1-2 heteroatoms independently selected from nitrogen, oxygen, or sulfur, wherein the ring thereby formed is optionally substituted with —(R$^5$)$_n$. In some embodiments, W is —C(O)N(R$^4$)$_2$, wherein both R$^4$ groups are taken together with the nitrogen atom to which they are attached to form a 4-7-membered saturated heterocyclic ring having 1 nitrogen atom, wherein the ring thereby formed is optionally substituted with —(R$^5$)$_n$.

In some embodiments, W is —C(O)N(R$^4$)$_2$, wherein both R$^4$ groups are taken together with the nitrogen atom to which they are attached to form a 4-6-membered saturated heterocyclic ring having 1 nitrogen atom, wherein the ring thereby formed is optionally substituted with —(R$^5$). In some embodiments, W is —C(O)N(R$^4$)$_2$, wherein both R$^4$ groups are taken together with the nitrogen atom to which they are attached to form a 4-5-membered saturated heterocyclic ring having 1 nitrogen atom, wherein the ring thereby formed is optionally substituted with —(R$^5$). In some embodiments, W is —C(O)N(R$^4$)$_2$, wherein both R$^4$ groups are taken together with the nitrogen atom to which they are attached to form a 4-membered saturated heterocyclic ring having 1 nitrogen atom, wherein the ring thereby formed is optionally substituted with —(R$^5$). In some embodiments, W is —C(O)N(R$^4$)$_2$, wherein both R$^4$ groups are taken together with the nitrogen atom to which they are attached to form a 4-membered saturated heterocyclic ring having 1 nitrogen atom, wherein the ring thereby formed is substituted with at least one fluorine. In some embodiments, W is —C(O)N(R$^4$)$_2$, wherein both R$^4$ groups are taken together with the nitrogen atom to which they are attached to form a 4-membered saturated heterocyclic ring having 1 nitrogen atom, wherein the ring thereby formed is substituted with at least two fluorines. In some embodiments, W is

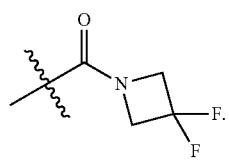 [SMILES: *C(=O)N1CC(F)(F)C1]

In some embodiments, R$^1$ is hydrogen. In some embodiments, R$^1$ is deuterium. In some embodiments, R$^2$ is hydrogen. In some embodiments, R$^2$ is deuterium. In some embodiments, R$^1$ and R$^2$ are each hydrogen.

In some embodiments, m is 1. In some embodiments, m is 2. In some such embodiments, R$^x$ is haloalkyl. In some embodiments, R$^x$ is —CF$_3$.

In some embodiments, R is hydrogen.

In some embodiments, the present invention provides a method of providing a compound of formula E.

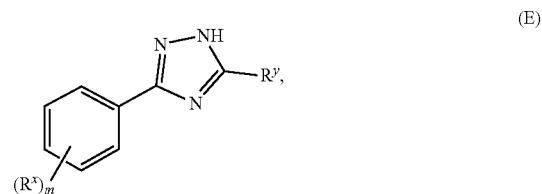

wherein R, R and m are as described for a compound of formula Z, comprising the steps of:

(a) providing a compound of formula D:

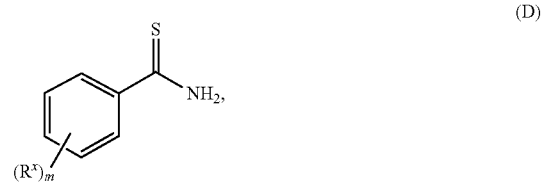

wherein each of R$^x$ and m is as defined above for a compound of formula E; and (b) reacting said compound of formula D to form a compound of formula E.

In some embodiments, conditions effective to form a compound of formula D includes a hydrazine equivalent. Thus, in some embodiments, step (b) of the method of providing a compound of formula E includes reaction said compound of formula D with a hydrazine equivalent to the form the compound of formula E. In some embodiments, intermediate D is reacted with hydrazine hydrate to provide a compound of formula E. In some embodiments, intermediate D is reacted with a protected form of hydrazine such as tert-butyl hydrazinecarboxylate and subsequently deprotected to provide intermediate D.

One of ordinary skill will recognize that the addition of hydrazine to intermediate D requires a polar, aprotic organic solvent. Suitable polar, aprotic organic solvents include ethers such as dioxane, tetrahydrofuran and methyl tert-butyl ether (MTBE), alcohols such as isopropyl alcohol, and amides such as dimethylformamide (DMF) and dimethyl-acetamide (DMA). One of ordinary skill is capable of selecting the appropriate solvent for the desired reaction temperature.

In some embodiments, the present invention provides a method for preparing a compound of formula D:

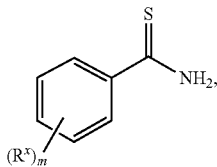
(D)

wherein $R^x$ and m are as defined above for a compound of formula Z,
comprising the steps of:
(a) providing a compound of formula C:

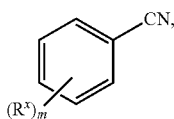
(C)

wherein each of $R^x$ and m is as defined above for a compound of formula D; and
(b) reacting said compound of formula C to form a compound of formula D.

As described above, in some embodiments, intermediate C is treated with a thiolate salt to provide intermediate D. In some embodiments, the thiolate salt is sodium thiolate. One of ordinary skill will recognize that the reaction of intermediate C with a thiolate salt requires the use of a polar, aprotic solvent. Suitable polar, aprotic solvents include ethers such as dioxane, tetrahydrofuran and methyl tert-butyl ether (MTBE).

In some embodiments, the present invention provides a method for preparing a compound of formula B:

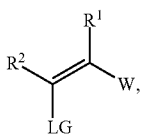
(B)

wherein:
LG is halogen, —$OSO_2R$ or —$OSO_2CF_3$; and
each of R, $R^1$, $R^2$ and W are as defined above for a compound of formula Z,
comprising the steps of:
(a) providing a compound of formula F:

(F)

wherein each of $R^2$ and W is as defined above for a compound of formula B; and
(b) reacting said compound of formula F to form a compound of formula B.

As described above, in some embodiments of intermediate B, LG is a halogen. In some such embodiments, a compound of formula F is treated with a halide salt. In some embodiments, a compound of formula F is treated with a sodium halide. In some such embodiments, a compound of formula F is treated with sodium iodide. In some embodiments, intermediate F is treated with a halide salt in the presence of an acid. Suitable acids include both mineral acids and organic acids. In some embodiments, intermediate F is treated with a halide salt and an organic acid such as acetic acid. In some embodiments, intermediate F is treated with sodium iodide in the presence of acetic acid to provide a compound of formula B.

One of ordinary skill will recognize that the addition of a halide salt to intermediate F requires a polar, aprotic organic solvent. Suitable polar, aprotic organic solvents include ethers such as dioxane, tetrahydrofuran and methyl tert-butyl ether (MTBE).

According to another aspect, the present invention provides a method of providing a compound of formula X:

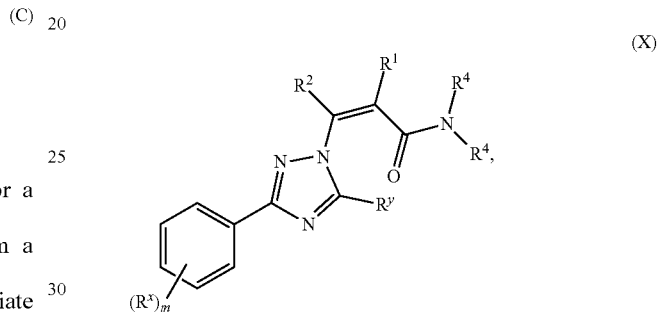
(X)

or a pharmaceutically acceptable salt thereof, wherein each of R, $R^x$, $R^y$, $R^1$, $R^2$, $R^4$ and m is as defined above with respect to a compound of formula Z,
comprising the steps of:
(a) providing a compound of formula E:

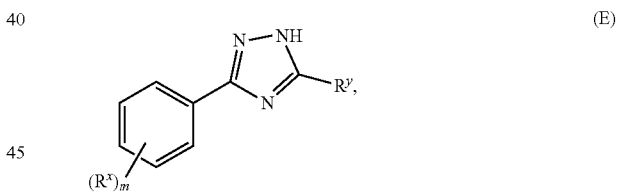
(E)

wherein each of R, $R^y$ and m is as defined above for a compound of formula X; and
(b) reacting said compound of formula E with an olefin of formula G:

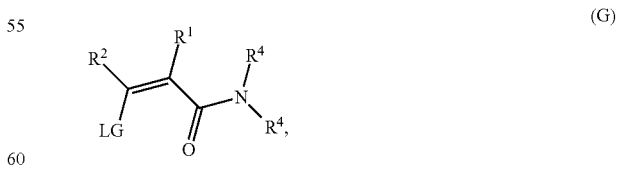
(G)

wherein:
LG is halogen, —$OSO_2R$ or —$OSO_2CF_3$; and
each of R, $R^1$, $R^2$ and $R^4$ is as defined above for a compound of formula X,
in the presence of a sterically-hindered nucleophilic base to form a compound of formula X.

According to another aspect, the present invention provides a method of providing a compound of formula W:

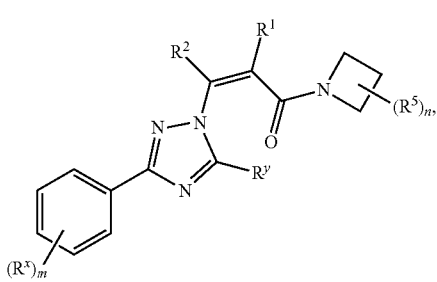
(W)

or a pharmaceutically acceptable salt thereof, wherein each of R, $R^x$, $R^y$, $R^1$, $R^2$, $R^5$, m and n is as defined above with respect to a compound of formula Z, comprising the steps of:

(a) providing a compound of formula E:

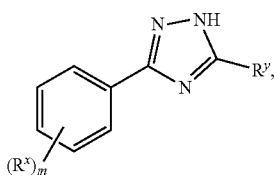
(E)

wherein each of R, $R^y$ and m is as defined above for a compound of formula W; and (b) reacting said compound of formula E with an olefin of formula H:

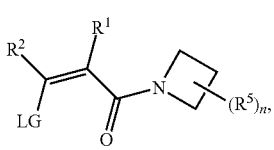
(H)

wherein:

LG is halogen, —OSO$_2$R or —OSO$_2$CF$_3$; and each of R, $R^1$, $R^2$, $R^5$ and n is as defined above for a compound of formula W, in the presence of a sterically-hindered nucleophilic base to form a compound of formula W.

According to another aspect, the present invention provides a method of providing a compound of formula V:

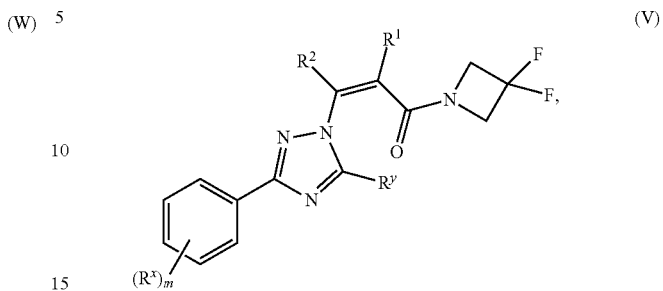
(V)

or a pharmaceutically acceptable salt thereof, wherein each of R, $R^x$, $R^y$, $R^1$, $R^2$, and m is as defined above with respect to a compound of formula Z, comprising the steps of:

(a) providing a compound of formula E:

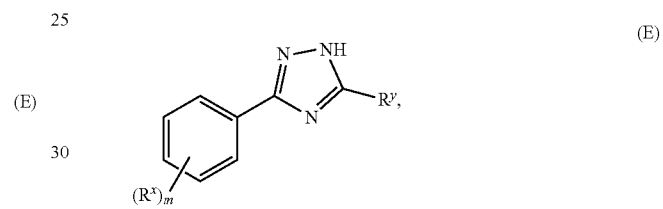
(E)

wherein each of $R^x$, $R^y$ and m is as defined above for a compound of formula V; and (b) reacting said compound of formula E with an olefin of formula J:

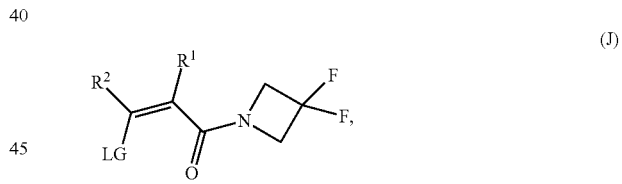
(J)

wherein:

LG is halogen, —OSO$_2$R or —OSO$_2$CF$_3$; and each of R, $R^1$ and $R^2$ is as defined above for a compound of formula V, in the presence of a sterically-hindered nucleophilic base to form a compound of formula V.

In some embodiments, the present invention provides a method for preparing a compound of formula G:

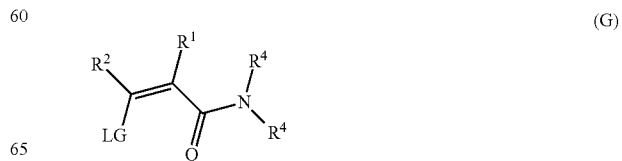
(G)

wherein:

LG is halogen, —OSO$_2$R or —OSO$_2$CF$_3$; and each of R, R$^1$, R$^2$ and R$^4$ is as described herein with respect to a compound of formula Z, comprising the steps of:

(a) providing a compound of formula K:

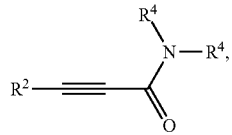

(K)

wherein each of R$^2$ and R$^4$ is as defined above for a compound of formula G; and (b) reacting said compound of formula K to form a compound of formula G.

As described above, in some embodiments of intermediate G, LG is a halogen. In some such embodiments, a compound of formula K is treated with a halide salt. In some embodiments, a compound of formula K is treated with a sodium halide. In some such embodiments, a compound of formula K is treated with sodium iodide. In some embodiments, intermediate K is treated with a halide salt in the presence of an acid. Suitable acids include both mineral acids and organic acids. In some embodiments, intermediate K is treated with a halide salt and an organic acid such as acetic acid. In some embodiments, intermediate K is treated with sodium iodide in the presence of acetic acid to provide a compound of formula G.

In some embodiments, the present invention provides a method for preparing a compound of formula K:

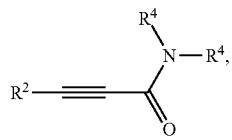

(K)

wherein each of R$^2$ and R$^4$ is as defined above with respect to a compound of formula Z, comprising the steps of:

(a) providing a compound of formula L:

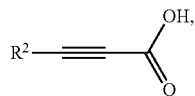

(L)

wherein R$^2$ is hydrogen, deuterium, tritium or halogen; and (b) reacting said compound of formula L with HN(R$^4$)$_2$, wherein each R$^4$ is as defined above with respect to a compound of formula K, to form a compound of formula K.

In some embodiments, a compound of formula L is treated with an amide coupling agent in the presence of HN(R$^4$)$_2$ to form a compound of formula K. Suitable amide coupling agents include HOBt, HOAt, HAMDU, HAMTU, PyBOP, PyBrOP, TBTU, HATU and T3P.

One of ordinary skill will recognize that the use of such amide coupling reagents requires the use of a base. Suitable bases include organic bases, such as triethylamine, diisopropylethyl amine, pyridine, 4-dimethylpyridine (DMAP), and the like.

In some embodiments, a compound of formula L is reacted with a chlorinating agent such as thionyl chloride to form an acyl chloride, which is then reacted with HN(R$^4$)$_2$ to form a compound of formula K.

In some embodiments, the present invention provides a method for preparing a compound of formula G:

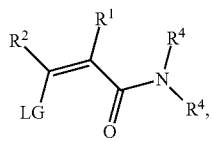

(G)

wherein:

LG is halogen, —OSO$_2$R or —OSO$_2$CF$_3$; and each of R, R$^1$, R$^2$ and R$^4$ is as defined above with respect to a compound of formula Z, comprising the steps of:

(a) providing a propargylic acid of formula L:

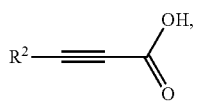

(L)

wherein R$^2$ is as defined above for a compound of formula G, (b) reacting said compound of formula L with an alcohol having the formula HO—R to form a propargylic ester of formula M:

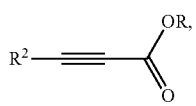

(M)

wherein each of R and R$^2$ is as defined above for a compound of formula G;

(c) reacting said propargylic ester of formula M to form a compound of formula N:

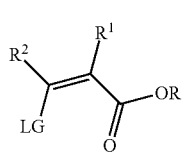

(N)

wherein each of R, R$^1$, R$^2$ and LG is as defined above for a compound of formula G;

(d) hydrolyzing said compound of formula N to form a compound of formula Q:

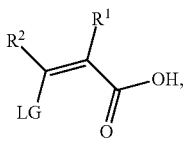
(Q)

wherein each of R, $R^1$, $R^2$ and LG is as defined above for a compound of formula G; and (e) reacting said compound of formula Q with $HN(R^4)_2$, wherein each $R^4$ is as defined above for a compound of formula G, to form a compound of formula G.

In some embodiments, a propargylic acid of formula L is treated with an alcohol to form a propargylic ester of formula M. Suitable alcohols include methanol, ethanol and isopropanol. One of ordinary skill will recognize that the esterification of a propargylic acid of formula L can be effected by catalytic acid. Thus, in some embodiments, a propargylic acid of formula L is treated with methanol or ethanol in the presence of catalytic sulfuric acid to provide a propargylic ester of formula M.

One of ordinary skill will recognize that such esterification can be performed at temperatures of about 25° C. to about 100° C., or up to the boiling point of the alcohol. In some embodiments, the esterification of a propargylic acid of formula L is heated to reflux (the boiling point of the alcohol).

As described above, in some embodiments of a compound of formula N, LG is a halogen. In some such embodiments, a compound of formula M is treated with a halide salt.

In some embodiments, a compound of formula M is treated with a sodium halide. In some such embodiments, a compound of formula M is treated with sodium iodide. In some embodiments, a compound of formula M is treated with a halide salt in the presence of an acid. Suitable acids include both mineral acids and organic acids. In some embodiments, a compound of formula M is treated with a halide salt and an organic acid such as acetic acid. In some embodiments, a compound of formula M is treated with sodium iodide in the presence of acetic acid to provide a compound of formula N.

In some embodiments, the ester of a compound of formula N is hydrolyzed to the acrylic acid. Suitable hydrolysis conditions are known to those skilled in the art and include hydroxide such as lithium hydroxide, sodium hydroxide, potassium hydroxide and cesium hydroxide in the presence of water. One of ordinary skill will recognize that such hydrolysis can be performed at temperatures of about 25° C. to about 100° C. In some embodiments, the hydrolysis of an acrylate of formula N is heated to reflux.

In some embodiments, an acrylic acid of formula Q is reacted with $HN(R^4)_2$ to form a compound of formula G. In some embodiments, an acrylic acid of formula Q is treated with an amide coupling agent in the presence of $HN(R^4)_2$ to form a compound of formula G. Suitable amide coupling agents include HOBt, HOAt, HAMDU, HAMTU, PyBOP, PyBrOP, TBTU, HATU and T3P. One of ordinary skill will recognize that the use of such amide coupling reagents requires the use of a base. Suitable bases include organic bases such as triethylamine, diisopropylethyl amine, pyridine, 4-dimethylpyridine (DMAP), and the like.

In some embodiments, a compound of formula Q is reacted with a chlorinating agent such as thionyl chloride to form an acyl chloride, which is then reacted with $HN(R^4)_2$ to form a compound of formula G.

In some embodiments, the present invention provides a method of providing a compound of formula V:

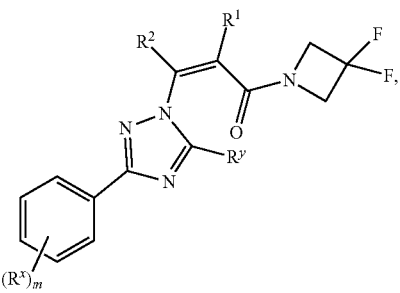
(V)

or a pharmaceutically acceptable salt thereof, wherein each of R, $R^x$, $R^y$, $R^1$, $R^2$ and m is as defined above with respect to a compound of formula Z, comprising the steps of:

(a) providing a compound of formula L:

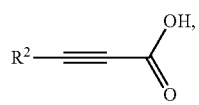
(L)

wherein $R^2$ is as defined above for a compound of formula V;

(b) reacting said compound of formula L with

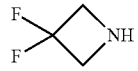

to form a compound of formula R:

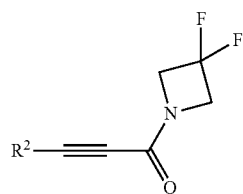
(R)

wherein $R^2$ is as defined above for a compound of formula V;

(c) reacting said compound of formula R to provide a compound of formula J:

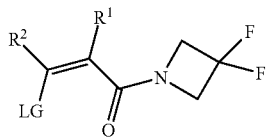

(J)

wherein:
LG is halogen, —OSO$_2$R or —OSO$_2$CF$_3$; and
each of R, R$^1$ and R$^2$ is as defined above for a compound of formula V; and (d) reacting said compound of formula J with a compound of formula E:

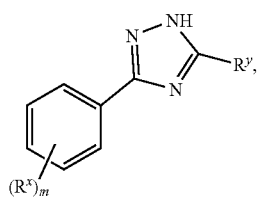

(E)

wherein each of R$^x$, R$^y$ and m is as defined above for a compound of formula V,
in the presence of a sterically-hindered nucleophilic base to provide a compound of formula V.

In some embodiments, the present invention provides a method of providing a compound of formula V:

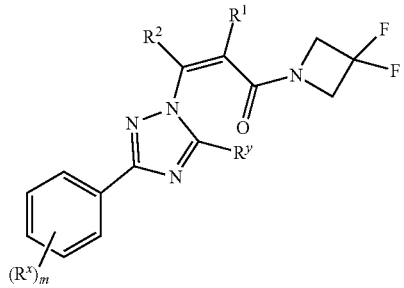

(V)

or a pharmaceutically acceptable salt thereof, wherein each of R, R$^x$, R$^y$, R$^1$, R$^2$ and m is as defined above with respect to a compound of formula Z,
comprising the steps of:
(a) providing a compound of formula L:

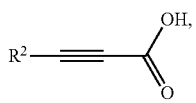

(L)

wherein R$^2$ is as defined above for a compound of formula V;

(b) reacting said compound of formula L with an alcohol having the formula HO—R to form a compound of formula M:

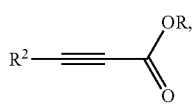

(M)

wherein each of R and R$^2$ is as defined above for a compound of formula V, (c) reacting said compound of formula M to provide a compound of formula N:

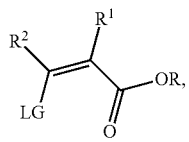

(N)

wherein:
LG is halogen, —OSO$_2$R or —OSO$_2$CF$_3$; and
each of R, R$^1$ and R$^2$ is as defined above for a compound of formula V;

(d) hydrolyzing said compound of formula N to form a compound of formula Q:

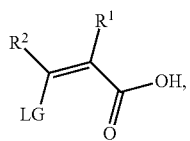

(Q)

wherein each of R$^1$, R$^2$ and LG is as defined above for a compound of formula V;

(e) reacting said compound of formula Q with

to form a compound of formula J:

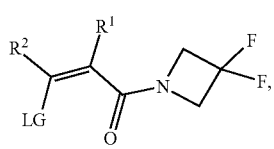

(J)

wherein:
LG is halogen, —OSO$_2$R or —OSO$_2$CF$_3$; and
each of R, R$^1$ and R$^2$ is as defined above for a compound of formula V; and (f) reacting said compound of formula J with a compound of formula E:

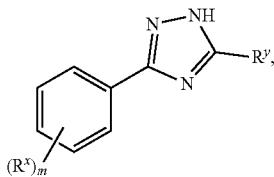
(E)

wherein each of R, R$^y$ and m is as defined above for a compound of formula V, in the presence of a sterically-hindered nucleophilic base to provide a compound of formula V.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

The term "aliphatic" or "aliphatic group," as used herein, denotes a monovalent hydrocarbon radical that is straight-chain (i.e., unbranched), branched, or cyclic (including fused, bridged, and spiro-fused polycyclic). An aliphatic group can be saturated or can contain one or more units of unsaturation, but is not aromatic. Unless otherwise specified, aliphatic groups contain 1-6 carbon atoms. However, in some embodiments, an aliphatic group contains 1-10 or 2-8 carbon atoms. In some embodiments, aliphatic groups contain 1-4 carbon atoms and, in yet other embodiments, aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl," as used herein, means a saturated, straight-chain or branched aliphatic group. In one aspect, an alkyl group contains 1-10 or 2-8 carbon atoms. Alkyl includes, but is not limited to, methyl, ethyl, propyl, iso-propyl, n-butyl, sec-butyl, t-butyl, and the like.

The term "alkenyl," as used herein, means a straight-chain or branched aliphatic group having one or more carbon-carbon double bonds (i.e., —CH=CH—). In one aspect, an alkenyl group has from two to eight carbon atoms, and includes, for example, and without being limited thereto, ethenyl, 1-propenyl, 1-butenyl and the like. The term "alkenyl" encompasses radicals having carbon-carbon double bonds in the "cis" and "trans" or, alternatively, the "E" and "Z" configurations. If an alkenyl group includes more than one carbon-carbon double bond, each carbon-carbon double bond is independently a cis or trans double bond, or a mixture thereof.

The term "alkynyl," as used herein, means a straight-chain or branched aliphatic radical having one ore more carbon-carbond triple bonds (i.e., —C≡C—). In one aspect, an alkyl group has from two to eight carbon atoms, and includes, for example, and without being limited thereto, 1-propynyl (propargyl), 1-butynyl and the like.

The terms "cycloaliphatic," "carbocyclyl," "carbocyclo," and "carbocyclic," used alone or as part of a larger moiety, refer to a saturated or partially unsaturated cyclic aliphatic monocyclic or bicyclic ring system, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. The terms "cycloaliphatic," "carbocyclyl," "carbocyclo," and "carbocyclic" also include aliphatic rings that are fused to one or more aromatic or nonaromatic rings, such as decahydronaphthyl, tetrahydronaphthyl, decalin, or bicyclo [2.2.2]octane.

The term "cycloalkyl," as used herein, means a saturated cyclic aliphatic monocyclic or bicyclic ring system having from 3-10 members. A cycloalkyl can be optionally substituted as described herein. In some embodiments, a cycloalkyl has 3-6 carbons.

The term "heterocycloalkyl," as used herein, means a saturated or unsaturated aliphatic ring system in which at least one carbon atom is replaced with a heteroatom selected from N, S and O. A heterocycloalkyl can contain one or more rings, which may be attached together in a pendent manner or may be fused. In one aspect, a heterocycloalkyl is a three- to seven-membered ring system and includes, for example, and without being limited thereto, piperidinyl, piperazinyl, pyrrolidinyl, tetrahydrofuranyl and the like.

The term "heteroatom" means one or more of oxygen, sulfur, nitrogen, phosphorus, or silicon, and includes any oxidized form of nitrogen, sulfur, phosphorus, or silicon; the quaternized form of any basic nitrogen; and a substitutable nitrogen of a heterocyclic ring, for example N (as in 3,4-dihydro-2H-pyrrolyl), NH (as in pyrrolidinyl) or NR+ (as in N-substituted pyrrolidinyl).

The term "unsaturated," as used herein, means that a moiety has one or more units of unsaturation.

The term "halo" or "halogen," as used herein, means halogen and includes, for example, and without being limited thereto, fluoro, chloro, bromo, iodo and the like, in both radioactive and non-radioactive forms.

The term "haloalkyl," as used herein, means an aliphatic group which is substituted with one or more halogen atoms.

In some embodiments, haloalkyl refers to a perhalogenated aliphatic group. In some embodiments, haloalkyl refers to an alkyl group which is substituted with one or more halogen atoms. Exemplary haloalkyl groups include —$CF_3$, —$CCl_3$, —$CF_2CH_3$, —$CH_2CF_3$, —$CH_2(CF_3)_2$, —$CF_2(CF_3)_2$, and the like.

The term "aryl," alone or in combination, as used herein, means a carbocyclic aromatic system containing one or more rings, which may be attached together in a pendent manner or may be fused. In particular embodiments, aryl is one, two or three rings. In one aspect, the aryl has five to twelve ring atoms. The term "aryl" encompasses aromatic radicals such as phenyl, naphthyl, tetrahydronaphthyl, indanyl, biphenyl, phenanthryl, anthryl and acenaphthyl. An "aryl" group can have 1 to 4 substituents, such as lower alkyl, hydroxyl, halo, haloalkyl, nitro, cyano, alkoxy, lower alkylamino and the like.

The term "heteroaryl," alone or in combination, as used herein, means an aromatic system wherein at least one carbon atom is replaced by a heteroatom selected from N, S and O. A heteroaryl can contain one or more rings, which may be attached together in a pendent manner or may be fused. In particular embodiments, heteroaryl is one, two or three rings. In one aspect, the heteroaryl has five to twelve ring atoms. The term "heteroaryl" encompasses heteroaromatic groups such as triazolyl, imidazolyl, pyrrolyl, pyrazolyl, tetrazolyl, pyridyl, pyrimidinyl, pyrazinyl, pyridazinyl, indolyl, furyl, benzofuryl, thienyl, benzothienyl, quinolyl, oxazolyl, oxadiazolyl, isoxazolyl, and the like. A "heteroaryl" group can have 1 to 4 substituents, such as lower alkyl, hydroxyl, halo, haloalkyl, nitro, cyano, alkoxy, lower alkylamino and the like.

It is understood that substituents and substitution patterns on the compounds of the invention can be selected by one of ordinary skill in the art to provide compounds that are chemically stable and that can be readily synthesized by techniques known in the art, as well as those methods set forth below. In general, the term "substituted," whether preceded by the term "optionally" or not, means that one or more hydrogens of the designated moiety are replaced with a suitable substituent. Unless otherwise indicated, an "optionally substituted" group can have a suitable substituent at each substitutable position of the group and, when more than one position in any given structure may be substituted with more than one substituent selected from a specified group, the substituent can be either the same or different at every position. Alternatively, an "optionally substituted" group can be unsubstituted.

Combinations of substituents envisioned by this invention are preferably those that result in the formation of stable or chemically feasible compounds. If a substituent is itself substituted with more than one group, it is understood that these multiple groups can be on the same carbon atom or on different carbon atoms, as long as a stable structure results. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{1-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl monocyclic or bicyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —$(CH_2)_{0-2}R^•$, -(halo$R^•$), —$(CH_2)_{0-2}OH$, —$(CH_2)_{0-2}OR^•$, —$(CH_2)_{0-2}CH(OR^•)_2$; —O(halo$R^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)O$R^•$, or —$SSR^•$ wherein each $R^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted" group include the following: =O, =S, =NNR*2, =NNHC(O)R*, =NNHC(O)OR*, =NNHS(O)$_2$R*, =NR*, =NOR*, —$O(C(R^*_2))_{2-3}O$—, and —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —$O(CR^*2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —$R^•$, -(halo$R^•$), —OH, —$OR^•$, —O(halo$R^•$), —CN, —C(O)OH, —C(O)O$R^•$, —$NH_2$, —$NHR^•$, —$NR^•_2$, and —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, and —N(R†)S(O)$_2$R†; wherein each R† is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of RT, taken together with their intervening atom(s) form an unsubstituted 3-12-membered saturated, partially unsaturated, or aryl monocyclic or bicyclic ring having 0-4 heteroatoms independently selected from nitrogen, oxygen, and sulfur.

Suitable substituents on the aliphatic group of R† are independently halogen, —R°, -(haloR°), —OH, —OR°, —O(haloR°), —CN, —C(O)OH, —C(O)OR°, —NH$_2$, —NHR°, —NR°$_2$, or —NO$_2$, wherein each R° is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

As used herein, "hydrazine equivalent" means a chemical reagent that can be used to introduce a —N—N— moiety into a molecule. Hydrazine equivalents include hydrazine hydrate as well as protected forms of hydrazine, such as tert-butyl hydrazine carboxylate.

As used herein, "leaving group" refers to a functional group that is displaced from a molecule during a chemical reaction. Leaving groups include halogens, as well sulfonate groups, such as tosylate and mesylate.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds of this invention include salts derived from suitable inorganic and organic acids and bases that are compatible with the treatment of patients.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

In some embodiments, acid addition salts of the compounds of formula I are most suitably formed from pharmaceutically acceptable acids, and include, for example, those formed with inorganic acids, e.g., hydrochloric, sulfuric or phosphoric acids and organic acids e.g. succinic, maleic, acetic or fumaric acid.

Other non-pharmaceutically acceptable salts, e.g., oxalates can be used, for example, in the isolation of compounds of formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

A "pharmaceutically acceptable basic addition salt" is any non-toxic organic or inorganic base addition salt of the acid compounds represented by formula I, or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}$C- or $^{14}$C-enriched carbon are within the scope of this invention. Such compounds are useful, for example, as analytical tools, as probes in biological assays, or as therapeutic agents in accordance with the present invention.

The term "stereoisomers" is a general term for all isomers of an individual molecule that differ only in the orientation of their atoms in space. It includes mirror image isomers (enantiomers), geometric (cis/trans) isomers and isomers of compounds with more than one chiral center that are not mirror images of one another (diastereomers).

The term "treat" or "treating" means to alleviate one or more symptoms, to eliminate the causation of one or more symptoms, either on a temporary or permanent basis, or to prevent or delay the onset of one or more symptoms associated with a disorder or condition.

The term "therapeutically effective amount" means an amount of a compound that is effective in treating or lessening the severity of one or more symptoms of a disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of being administered to a patient. One example of such a carrier is pharmaceutically acceptable oil typically used for parenteral administration. Pharmaceutically acceptable carriers are well known in the art.

When introducing elements disclosed herein, the articles "a," "an," "the," and "said" are intended to mean that there are one or more of the elements. The terms "comprising," "having" and "including" are intended to be open-ended and mean that there may be additional elements other than the listed elements.

Formulation and Administration

Pharmaceutically Acceptable Compositions

Another embodiment of the invention is a composition comprising a compound of the invention, or a pharmaceutically acceptable salt thereof, and a pharmaceutically acceptable carrier, adjuvant, or vehicle. The amount of compound in a composition of the invention is an amount that is effective to measurably inhibit CRM1 in a biological sample or in a patient. In certain embodiments, a composition of the invention is formulated for administration to a patient in need of the composition. The term "patient," as used herein, means an animal. In some embodiments, the animal is a mammal. In certain embodiments, the patient is a veterinary patient (i.e., a non-human mammal patient). In some embodiments, the patient is a dog. In other embodiments, the patient is a human.

The phrase "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitoneally.

The term "parenteral," as used herein, includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For ophthalmic use, pharmaceutically acceptable compositions can be formulated as micronized suspensions or in an ointment such as petrolatum.

Pharmaceutically acceptable compositions of this invention can also be administered by nasal aerosol or inhalation.

In some embodiments, pharmaceutically acceptable compositions of this invention are formulated for intra-peritoneal administration.

The amount of compounds of the present invention that may be combined with the carrier materials to produce a composition in a single dosage form will vary depending upon the host treated and the particular mode of administration. In one embodiment, a composition is formulated so that a dosage of between 0.01-100 mg/kg body weight/day of the inhibitor can be administered to a patient receiving the composition. In another embodiment, the dosage is from about 0.5 to about 100 mg/kg of body weight, or between 1 mg and 1000 mg/dose, every 4 to 120 hours, or according to the requirements of the particular drug. Typically, the pharmaceutical compositions of this invention will be administered from about 1 to about 6 times per day.

It should also be understood that a specific dosage and treatment regimen for any particular patient will depend upon a variety of factors, including the activity of the specific compound employed, the age, body weight, general health, sex, diet, time of administration, rate of excretion, drug combination, the judgment of the treating physician and the severity of the particular disease being treated. The amount of a compound of the present invention in the composition will also depend upon the particular compound in the composition.

In some embodiments, the composition further includes one or more additional therapeutic or prophylactic agents. When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents can be administered separately, as part of a multiple dose regimen, from the compounds of this invention. Alternatively, the additional agents can be part of a single dosage form, mixed together with a compound of the invention in a single composition.

Upon improvement of a patient's condition, a maintenance dose of a compound, composition or combination of this invention can be administered, if necessary. Subsequently, the dosage or frequency of administration, or both, can be reduced, as a function of the symptoms, to a level at which the improved condition is retained when the symptoms have been alleviated to the desired level. Patients may, however, require intermittent treatment on a long-term basis upon any recurrence of disease symptoms Uses of Compounds and Pharmaceutically Acceptable Compositions Compounds and compositions described herein are generally useful for the inhibition of CRM1 and are, therefore, useful for treating one or more disorders associated with activity of CRM1. Thus, in certain embodiments, the present invention provides a method for treating a CRM1-mediated disorder comprising the step of administering to a patient in need thereof a compound of the present invention, or pharmaceutically acceptable salt or composition thereof. The compounds and compositions described herein can also be administered to cells in culture, e.g., in vitro or ex vivo, or to a subject, e.g., in vivo, to treat, prevent, and/or diagnose a variety of disorders, including those described herein below.

The activity of a compound utilized in this invention as an inhibitor of CRM1 may be assayed in vitro, in vivo or in a cell line. Detailed conditions for assaying a compound utilized in this invention as an inhibitor of CRM1 are set forth in the Exemplification.

As used herein, the term "CRM1-mediated disorder or condition" or "disorder or condition associated with CRM1 activity" means any disease or other deleterious condition in which CRM1 plays a role. Accordingly, another embodiment of the present invention relates to treating or lessening the severity of one or more diseases in which CRM1 plays a role. In some embodiments, the present invention provides methods of treating a disease associated with expression or activity of p53, p73, p21, pRB, p27, IxB, NFκB, c-Abl, FOXO proteins, COX-2 in a subject comprising administering to the patient a therapeutically effective amount of a compound described herein. In another embodiment, the present invention relates to a method of treating or lessening the severity of a disease or condition selected from a proliferative disorder (e.g., cancer), an inflammatory disorder, an autoimmune disorder, a viral infection, an ophthalmological disorder or a neurodegenerative disorder, the method comprising administering to a patient in need thereof a compound or composition according to the present invention. In a more specific embodiment, the present invention relates to a method of treating or lessening the severity of cancer. Specific examples of the above disorders are set forth in detail below.

Cancers treatable by the compounds of this invention include, but are not limited to, hematologic malignancies (leukemias, lymphomas, myelomas, myelodysplastic and myeloproliferative syndromes) and solid tumors (carcinomas such as prostate, breast, lung, colon, pancreatic, renal, ovarian as well as soft tissue and osteosarcomas, and stromal tumors). Breast cancer (BC) can include, Basal-like Breast Cancer (BLBC), Triple Negative Breast Cancer (TNBC) and breast cancer that is both BLBC and TNBC. In addition, breast cancer can include invasive or non-invasive ductal or lobular carcinoma, tubular, medullary, mucinous, papillary, cribriform carcinoma of the breast, male breast cancer, recurrent or metastatic breast cancer, phyllodes tumor of the breast, paget's disease of the nipple.

Inflammatory disorders treatable by the compounds of this invention include, but are not limited to, multiple sclerosis, rheumatoid arthritis, degenerative joint disease, systemic lupus, systemic sclerosis, vasculitis syndromes (small, medium and large vessel), atherosclerosis, inflammatory bowel disease, irritable bowel syndrome, Crohn's disease, mucous colitis, ulcerative colitis, gastritis, sepsis, psoriasis and other dermatological inflammatory disorders (such as eczema, atopic dermatitis, contact dermatitis, urticaria, scleroderma, psoriasis, and dermatosis with acute inflammatory components, pemphigus, pemphigoid, allergic dermatitis), and urticarial syndromes. In some embodiments, the disorder or condition associated with CRM1 activity is multiple sclerosis, irritable bowel syndrome, rheumatoid arthritis, psoriasis or other dermatological inflammatory disorders.

Viral diseases treatable by the compounds of this invention include, but are not limited to, acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, poliomyelitis, rabies, influenza-like syndrome, severe bronchiolitis with pneumonia, German measles, congenital rubella, varicella, and herpes zoster. Viral diseases treatable by the compounds of this invention also include chronic viral infections, including hepatitis B and hepatitis C.

Exemplary ophthalmology disorders include, but are not limited to, macular edema (diabetic and nondiabetic macular edema), age-related macular degeneration (wet and dry forms), aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epitheliitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative diseases treatable by a compound of the invention include, but are not limited to, Parkinson's, Alzheimer's, and Huntington's, and amyotrophic lateral sclerosis (ALS/Lou Gehrig's Disease). In some embodiments, the disorder or condition associated with CRM1 activity is ALS.

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, and other renal disorders.

Compounds and compositions described herein may also be used to treat disorders related to food intake, such as obesity and hyperphagia. In some embodiments, the disorder or condition associated with CRM1 activity is obesity.

In some embodiments, the disorder or condition associated with CRM1 activity is muscular dystrophy, arthritis, for example, osteoarthritis and rheumatoid arthritis, ankylosing spondilitis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, musclewasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodontitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, or hearing loss.

In other embodiments, the disorder or condition associated with CRM1 activity is head injury, uveitis, inflammatory pain, allergen induced asthma, non-allergen induced asthma, glomerular nephritis, ulcerative colitis, necrotizing enterocolitis, hyperimmunoglobulinemia D with recurrent fever (HIDS), TNF receptor associated periodic syndrome (TRAPS), cryopyrin-associated periodic syndromes, Muckle-Wells syndrome (urticaria deafness amyloidosis), familial cold urticaria, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum, acne (PAPA), deficiency of the interleukin-1-receptor antagonist (DIRA), subarachnoid hemorrhage, polycystic kidney disease, transplant, organ transplant, tissue transplant, myelodysplastic syndrome, irritant-induced inflammation, plant irritant-induced inflammation, poison ivy/urushiol oil-induced inflammation, chemical irritant-induced inflammation, bee sting-induced inflammation, insect bite-induced inflammation, sunburn, burns, dermatitis, endotoxemia, lung injury, acute respiratory distress syndrome, alcoholic hepatitis, or kidney injury caused by parasitic infections.

In another embodiment, a compound or composition described herein may be used to treat or prevent allergies and respiratory disorders, including asthma, bronchitis, pulmonary fibrosis, allergic rhinitis, oxygen toxicity, emphysema, chronic bronchitis, acute respiratory distress syndrome, and any chronic obstructive pulmonary disease (COPD).

Another embodiment of the invention is use of a compound of formula I in the manufacture of a medicament for the treatment of a disorder or condition associated with CRM1 activity. In further aspects, the present invention provides a use of a compound of formula I for the manufacture of a medicament for the treatment of a disease associated with expression or activity of p53, p73, p21, pRB, p27, IκB, NFκB, c-Abl, FOXO proteins or COX-2 in a subject. In some embodiments, the present invention provides a use of a compound of formula I in the manufacture of a medicament for the treatment of any of cancer and/or neoplastic disorders, angiogenesis, autoimmune disorders, inflammatory disorders and/or diseases, epigenetics, hormonal disorders and/or diseases, viral diseases, neurodegenerative disorders and/or diseases and ophthalmologic disorders.

In some embodiments, the present invention provides a method for inhibiting CRM1 in a biological sample or a patient comprising contacting the biological sample with, or administering to the patient, a pharmaceutically acceptable salt of a compound of formula I, or pharmaceutically acceptable composition thereof.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth, benign or malignant. Exemplary neoplastic disorders include: carcinoma, sarcoma (e.g., soft tissue), osteosarcoma, metastatic disorders (e.g., tumors arising from prostate, brain, bone, gastrointestinal, lung, breast, ovarian, cervical, pancreas, kidney, head and neck, and liver origin), hematopoietic neoplastic disorders (e.g., leukemias, lymphomas, myeloma and other malignant plasma cell disorders), and metastatic tumors. In one embodiment, the cancer to be treated is selected from breast, ovarian, cervical, gastrointestinal, prostate, colon, lung, renal, brain, liver, and pancreatic cancer. Treatment with the compound may be in an amount effective to ameliorate at least one symptom of the neoplastic disorder, e.g., reduced cell proliferation, reduced tumor mass, etc.

In one embodiment, the neoplastic disorder is a Basal-like breast cancer (BLBC). BLBCs account for up to 15% of breast cancers (BC) and are usually triple negative breast cancer (TNBC), characterized by lack of ER, progesterone receptor PR, and HER-2 amplification. In a specific embodiment, the breast cancer is TNBC. In addition, most BRCA1-associated BCs are BLBC and TNBC, expressing basal cytokeratins and EGFR. BLBC is characterized by an aggressive phenotype, high histological grade, and poor clinical outcomes with high recurrence and metastasis rates.

Combination Therapies

In some embodiments, a compound described herein is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

In one embodiment of the invention, in which a second therapeutic agent is administered to a subject, the effective amount of the compound of the invention is less than its effective amount would be were the second therapeutic agent not administered. In another embodiment, the effective amount of the second therapeutic agent is less than its effective amount would be were the compound of the invention not administered. In this way, undesired side effects associated with high doses of either agent may be minimized. Other potential advantages (including, without limitation, improved dosing regimens and/or reduced drug cost) will be apparent to those of skill in the art.

Exemplary additional cancer treatments include, for example: chemotherapy, targeted therapies such as antibody therapies, kinase inhibitors, immunotherapy, and hormonal therapy, epigenetic therapy, proteosome inhibitors, and anti-angiogenic therapies. Examples of each of these treatments are provided below.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include aclarubicin, actinomycin, alitretinoin, altretamine, aminopterin, aminolevulinic acid, amrubicin, amsacrine, anagrelide, arsenic trioxide, asparaginase, atrasentan, belotecan, bexarotene, bendamustin, bleomycin, bortezomib, busulfan, camptothecin, capecitabine, carboplatin, carboquone, carmofur, carmustine, celecoxib, chlorambucil, chlormethine, cisplatin, cladribine, clofarabine, crisantaspase, cyclophosphamide, cytarabine, dacarbazine, dactinomycin, daunorubicin, decitabine, demecolcine, docetaxel, doxorubicin, efaproxiral, elesclomol, elsamitrucin, enocitabine, epirubicin, estramustine, etoglucid, etoposide, floxuridine, fludarabine, fluorouracil (5FU), fotemustine, gemcitabine, gliadel implants, hydroxycarbamide, hydroxyurea, idarubicin, ifosfamide, irinotecan, irofulven, ixabepilone, larotaxel, leucovorin, liposomal doxorubicin, liposomal daunorubicin, lonidamine, lomustine, lucanthone, mannosulfan, masoprocol, melphalan, mercaptopurine, mesna, methotrexate, methyl aminolevulinate, mitobronitol, mitoguazone, mitotane, mitomycin, mitoxantrone, nedaplatin, nimustine, oblimersen, omacetaxine, ortataxel, oxaliplatin, paclitaxel, pegaspargase, pemetrexed, pentostatin, pirarubicin, pixantrone, plicamycin, porfimer sodium, prednimustine, procarbazine, raltitrexed, ranimustine, rubitecan, sapacitabine, semustine, sitimagene ceradenovec, strataplatin, streptozocin, talaporfin, tegafururacil, temoporfin, temozolomide, teniposide, tesetaxel, testolactone, tetranitrate, thiotepa, tiazofurine, tioguanine, tipifarnib, topotecan, trabectedin, triaziquone, triethylenemelamine, triplatin, tretinoin, treosulfan, trofosfamide, uramustine, valrubicin, verteporfin, vinblastine, vincristine, vindesine, vinflunine, vinorelbine, vorinostat, zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted therapy constitutes the use of agents specific for the deregulated proteins of cancer cells. Small molecule targeted therapy drugs are generally inhibitors of enzymatic domains on mutated, overexpressed, or otherwise critical proteins within a cancer cell. Prominent examples are the tyrosine kinase inhibitors such as axitinib, bosutinib, cediranib, desatinib, erolotinib, imatinib, gefitinib, lapatinib, lestaurtinib, nilotinib, semaxanib, sorafenib, sunitinib, and vandetanib, and also cyclin-dependent kinase inhibitors such as alvocidib and seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and tositumomab typically used in a variety of B-cell malignancies. Other exemplary antibodies include cetuximab, panitumumab, trastuzumab, alemtuzumab, bevacizumab, edrecolomab, and gemtuzumab. Exemplary fusion proteins include aflibercept and denileukin diftitox. In some embodiments, targeted therapy can be used in combination with a compound described herein, e.g., Gleevec (Vignari and Wang 2001).

Targeted therapy can also involve small peptides as "homing devices" which can bind to cell surface receptors or affected extracellular matrix surrounding a tumor. Radionuclides which are attached to these peptides (e.g., RGDs) eventually kill the cancer cell if the nuclide decays in the vicinity of the cell. An example of such therapy includes BEXXAR®.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetic therapies include inhibitors of enzymes controlling epigenetic modifications, specifically DNA methyltransferases and histone deacetylases, which have shown promising anti-tumorigenic effects for some malignancies, as well as antisense oligonucleotides and siRNA.

Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal therapy agents include the administration of hormone agonists or hormone antagonists and include retinoids/retinoic acid, compounds that inhibit estrogen or testosterone, as well as administration of progestogens.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXEMPLIFICATION

Abbreviations atm Atmosphere
aq. Aqueous
BINAP 2,2'-bis(diphenylphosphino)-1,1'-binaphthyl
Boc tert-butoxycarbonyl
CDI N,N'-Carbonyldiimidazole
CH$_2$Cl$_2$ Dichloromethane
DCC N,N-Dicyclohexylcarbodiimide
DCM Dichloromethane
DBU Diaza(1,3)bicyclo[5.4.0]undecane
DIC N,N'-Diisopropylcarbodiimide
DIPEA N,N-Diisopropylethylamine
DMAP N,N-Dimethyl-4-aminopyridine
DMF N,N-Dimethylformamide
DMSO Dimethylsulfoxide
DPPF Diphenylphosphinoferrocene
EA Ethyl acetate
EDCI N-[3-(dimethylamino)propyl]-N'-ethylcarbodiimide hydrochloride
EDC 1-Ethyl-3-(3-dimethylaminopropyl)carbodiimide
eq. equivalent(s)
Et2O Diethylether
EtOAc Ethyl acetate
EtOH Ethanol
EtI Iodoethane
Et Ethyl
Fmoc 9-fluorenylmethyloxycarbonyl
GC Gas chromatography
h hour(s)
HetAr Heteroaryl
HOBt N-Hydroxybenzotriazole
HBTU O-(Benzotriazol-1-yl)-N,N,N',N'-tetramethyluroniumhexafluorophosphate
HPLC High performance liquid chromatography
LAH Lithium aluminium hydride
LCMS Liquid Chromatography Mass Spectrometry
MCPBA m-Chloroperbenzoic acid
MeCN Acetonitrile
MeOH Methanol
min Minutes
MeI Iodomethane
MeMgCl Methyl magnesium chloride
Me Methyl
NaOAc Sodium acetate
NMR Nuclear magnetic resonance
NMP N-Methyl pyrrolidinone
o.n. Over night
RT Room Temperature or Retention Time
T3P Propylphosphonic anhydride
TEA Triethylamine
THF Tetrahydrofuran
TLC Thin Layer Chromatography Throughout the following description of processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups, as well as examples of suitable protecting groups, are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Prepara- Example 1: Synthesis of Intermediate (Z)-3-(3-(3,5-bis(trifluoromethyl)phenyl)-1H-1,2,4-triazol-1-yl)acrylic acid

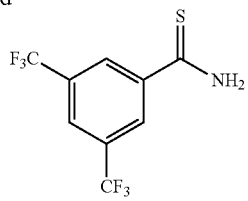

A 2-L, 3-necked, round-bottomed flask was charged with a solution of 3,5-bis(trifluoromethyl)benzonitrile (200 g) in DMF (1 L). The solution was then treated with NaSH (123.7 g, 2.0 eq.) and $MgCl_2$ (186.7 g, 1.0 eq.) and the reaction mixture was stirred at RT for 3 hours. The mixture was poured into an ice-water slurry (10 L) and the compound was extracted with EtOAc (3×1 L). The combined organic layers were washed with aqueous saturated brine (3×100 mL), dried over anhydrous $Na_2SO_4$, filtered, and concentrated under reduced pressure to afford 205 g of desired crude 3,5-bis(trifluoromethyl)benzothioamide (yield: 90%), which was used without purification in the following step.

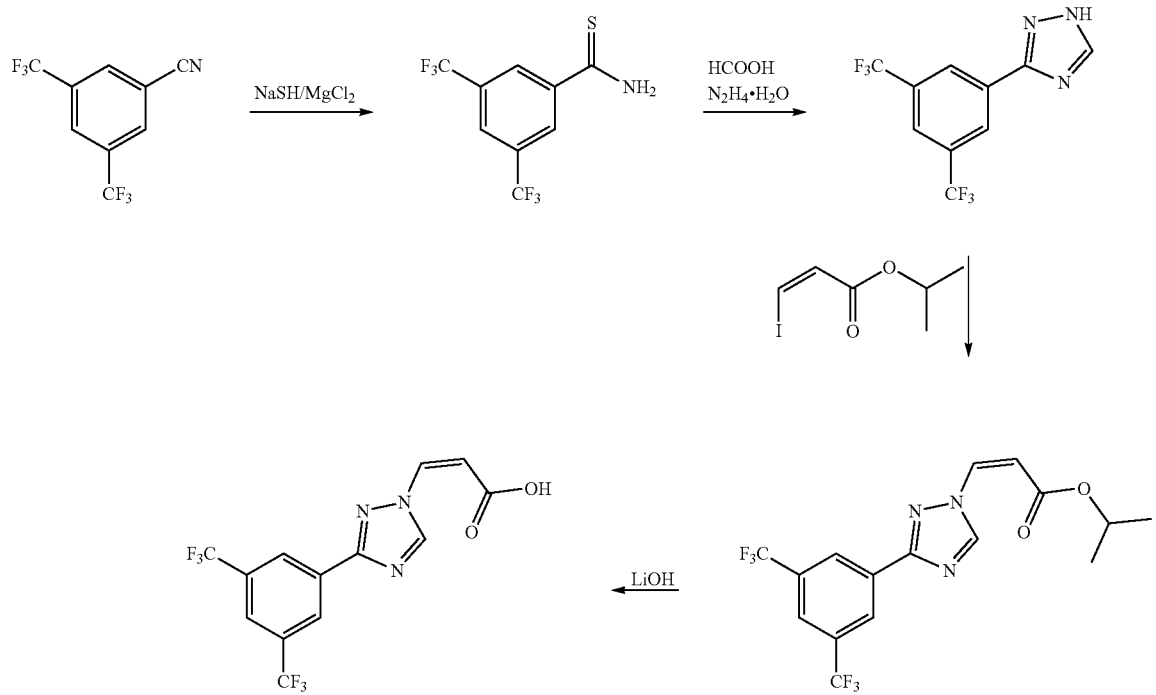

Synthesis of 3,5-bis(trifluoromethyl)benzothioamide

Synthesis of 3-(3,5-bis(trifluoromethyl)phenyl)-1H-1,2,4-triazole

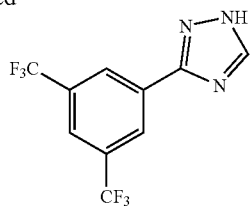

A 5-L, 3-necked, round-bottomed flask was charged with a solution of 3,5-bis(trifluoromethyl)benzothioamide (205.65 g) in DMF (1.03 L). Hydrazine hydrate (73.2 mL, 2.0 eq.) was added dropwise and the reaction mixture was stirred at RT for 1 h. HCOOH (1.03 L) was added dropwise and the reaction mixture was refluxed at 90° C. for 3 hours. After being allowed to cool to RT, the reaction mixture was poured into saturated aqueous sodium bicarbonate solution (7 L) and extracted with EtOAc (3×1 L). The combined organic layers were washed with aqueous saturated brine (3×500 mL), dried over anhydrous $Na_2SO_4$, filtered, and concentrated under reduced pressure (35° C., 20 mmHg) to afford 180 g of crude compound. This crude material was stirred with petroleum ether (3×500 mL), filtered and dried to obtain 160 g. of 3-(3,5-bis(trifluoromethyl)phenyl)-1H-1,2,4-triazole obtained as a pale yellow solid (yield: 75%).

Synthesis of (Z)-isopropyl 3-(3-(3,5-bis(trifluoromethyl)phenyl)-1H-1,2,4-triazol-1-yl)acrylate

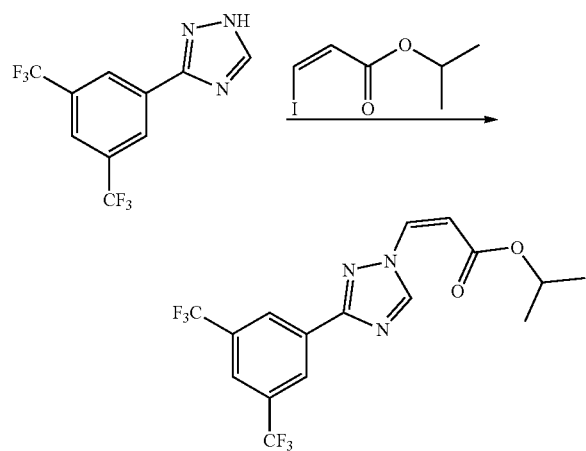

A 2-L, 3-necked, round-bottomed flask was charged with a solution of 3-(3,5-bis(trifluoromethyl)phenyl)-1H-1,2,4-triazole (160 g) in DMF (960 mL). The solution was treated with DABCO (127.74 g, 2 eq.) and stirred for 30 min before adding (Z)-isopropyl 3-iodoacrylate (150.32 g, 1.1 eq.) dropwise. After ca. 1 hour, the reaction mixture was poured into an ice-water slurry (5 L) and extracted with EtOAc (3×1 L). The combined organic layers were washed with aqueous saturated brine (3×100 mL), dried over anhydrous $Na_2SO_4$, filtered, and concentrated under reduced pressure (35° C., 20 mmHg) to afford 250 g of crude compound that was purified by column chromatography (60/120 silica gel) using a ethyl acetate/n-hexane gradient (the column was packed in hexane and the desired compound started eluting from 2% EtOAC/n-hexane). Fractions containing the desired compounds were combined to afford 138 g the pure desired compound (yield: 61%).

Synthesis of (Z)-3-(3-(3,5-bis(trifluoromethyl)phenyl)-1H-1,2,4-triazol-1-yl)acrylic acid

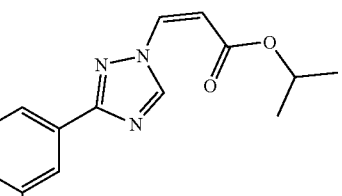

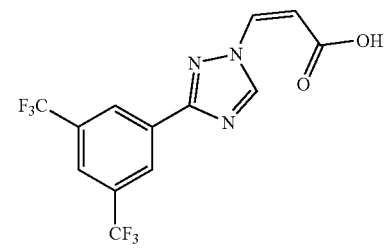

In a 5-L, 3-necked, round-bottomed flask, (Z)-isopropyl 3-(3-(3,5-bis(trifluoromethyl)phenyl)-1H-1,2,4-triazol-1-yl) acrylate (130 g, 1.0 eq.) was dissolved in THF (1.3 L). A solution of LiOH (69.3 g, 5.0 eq.) in water (1.3 L) was added dropwise to the solution and the reaction mixture was stirred at room temperature for 4 h before being quenched with 400 mL ice-water slurry and made acidic (pH=2-3) with dilute aqueous HCl. The mixture was extracted with EtOAc (3×1 L) and the combined organic layers were washed with brine, dried over anhydrous $Na_2SO_4$ and concentrated under reduced pressure to afford 110 g of desired carboxylic acid (yield: 94%) (cis content=90.0%, trans content=8.2% by LCMS).

Example 2: Synthesis of (Z)-3-(3-(3,5-bis(trifluoromethyl)phenyl)-1H-1,2,4-triazol-1-yl)-N'-(pyrazin-2-yl)acrylohydrazide (I-3)

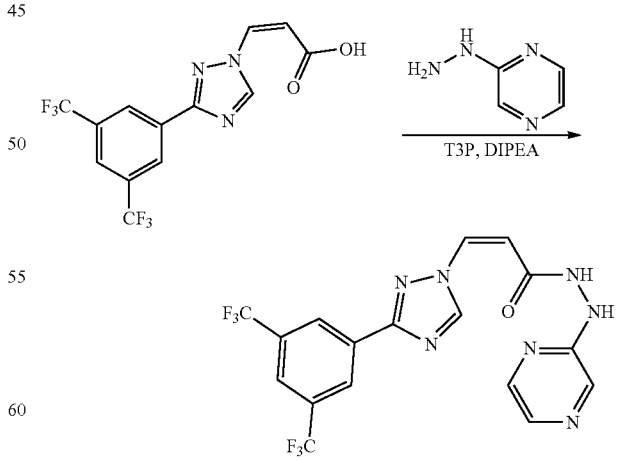

A 50-mL, 3-necked, round-bottomed flask was charged with a suspension of (Z)-3-(3-(3,5-bis(trifluoromethyl)phenyl)-1H-1,2,4-triazol-1-yl)acrylic acid (0.200 g) in 1:1 $CH_2Cl_2$: AcOEt (25 mL). 2-Hydrazinopyrazine (0.062 g)

was added at −40° C. followed by T3P (50%) (0.432 g) and DIPEA (0.147 g). The reaction mixture was stirred for 30 min at −40° C. before being concentrated under reduced pressure (35° C., 20 mmHg). The crude oil was purified by preparative TLC using 5% MeOH in $CH_2Cl_2$ as mobile phase (under ammonia atmosphere) to afford 40 mg (yield: 16%) of (Z)-3-(3-(3,5-bis(trifluoromethyl)phenyl)-1H-1,2,4-triazol-1-yl)-N'-(pyrazin-2-yl)acrylohydrazide. $^1$H NMR (400 MHz, DMSO-d6) δ, 10.53 (s, 1H), 9.59 (s, 1H), 9.14 (s, 1H), 8.53 (s, 2H), 8.29 (s, 1H), 8.13 (s, 1H), 8.06-8.07 (m, 1H), 7.92-7.93 (d, J=2.8 Hz, 1H), 7.51-7.53 (d, J=10.4 Hz, 1H), 6.07-6.10 (d, J=10.4 Hz, 1H); LCMS for $C_{17}H_{12}F_6N_7O$ [M+H]$^+$ predicted: 444.31, found: 444.49 (RT 2.70 min, purity: 95.78%).

Example 3: Synthesis of (Z)-3-(3-(3,5-bis(trifluoromethyl)phenyl)-1H-1,2,4-triazol-1-yl)-N'-(pyridin-2-yl)acrylohydrazide hydrochloride (I-4)

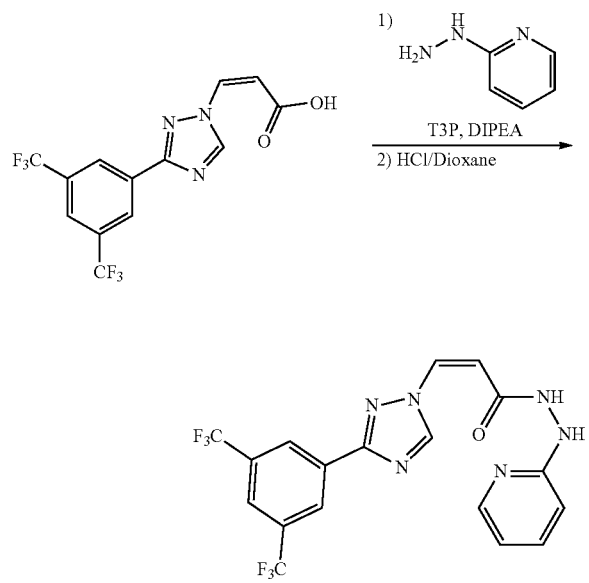

A 500-mL, 3-necked, round-bottomed flask was charged with a suspension of (Z)-3-(3-(3,5-bis(trifluoromethyl)phenyl)-1H-1,2,4-triazol-1-yl)acrylic acid (10 g, 1.0 eq.) in 1:1 CH2Cl2:AcOEt (200 mL). 2-Hydrazinopyridine (3.11 g) was added at −40° C. T3P (50% in ethylacetate) (21.75 g) was added dropwise followed by DIPEA (7.36 g) and the reaction mixture was stirred for 30 min at −40° C. before being concentrated under reduced pressure (35° C., 20 mm Hg) to afford a crude brown oil that was purified by column chromatography (the compound eluted with 1.3% MeOH in $CH_2Cl_2$). Fractions containing desired compound were combined to afford 6.0 g (yield: 48%) (Z)-3-(3-(3,5-bis-(trifluoromethyl)phenyl)-1H-1,2,4-triazol-1-yl)-N'-(pyridin-2-yl) acrylohydrazide. $^1$H NMR (400 MHz, DMSO-d6) δ, 10.41 (s, 1H), 9.66 (s, 1H), 8.59 (s, 1H), 8.53 (s, 2H), 8.28 (s, 1H), 8.06-8.08 (d, J=5.2 Hz, 1H), 7.48-7.53 (m, 1H), 7.49-7.52 (d, J=10.4, 1H), 6.71-6.75 (m, 1H), 6.66-6.68 (d, J=8.4 Hz, 1H), 6.07-6.09 (d, J=10.4, 1H). LCMS for $C_{18}H_{12}F_6N_6O$ [M+H]$^+$ predicted: 443.33, found: 443.44 (RT 2.45 min, purity: 100%).

Synthesis of (Z)-3-(3-(3,5-bis(trifluoromethyl)phenyl)-1H-1,2,4-triazol-1-yl)-N'-(pyridin-2-yl)acrylohydrazide hydrochloride

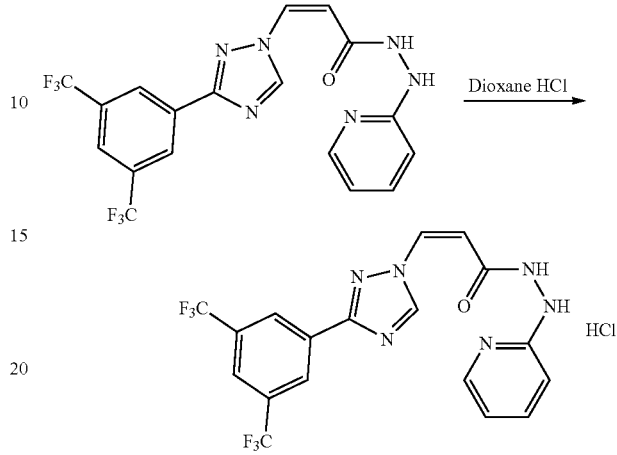

A 500-mL, 3-necked, round-bottomed flask was charged with a solution of (Z)-3-(3-(3,5-bis(trifluoromethyl)phenyl)-1H-1,2,4-triazol-1-yl)-N'-(pyridin-2-yl)acrylohydrazide (5.5 g) in Et20 (250 mL). The solution was cooled to 5° C., treated with HCl in 1,4-dioxane, allowed to warm to RT and stirred until completion, as shown by TLC analysis (about 1 h). The solids were filtered on a Buchner funnel, washed with Et20 and dried under vacuum to afford 5.5 g (yield: 92%) (Z)-3-(3-(3,5-bis(trifluoromethyl)phenyl)-1H-1,2,4-triazol-1-yl)-N'-(pyridin-2-yl)acrylohydrazide hydrochloride. $^1$H NMR (400 MHz, DMSO-d6) δ, 11.26 (s, 1H), 10.89 (s, 1H), 9.55 (s, 1H), 8.52 (s, 2H), 8.28 (s, 1H), 8.03-8.07 (m, 2H), 7.62-7.59 (d, J=10.4 Hz, 1H), 7.21-7.24 (m, 1H), 7.05-7.09 (m, 1H), 6.16-6.19 (d, J=10.4 Hz, 1H), LCMS for $C_{18}H_{13}F_6N_6O$ [M+H]$^+$ 443.33; found 443.44 (RT 3.54 min, purity: 99.0%).

Example 4: Synthesis of (Z)-3-(3-(3,5-bis(trifluoromethyl)phenyl)-1H-1,2,4-triazol-1-yl)-1-(4-hydroxypiperidin-1-yl)prop-2-en-1-one (I-5)

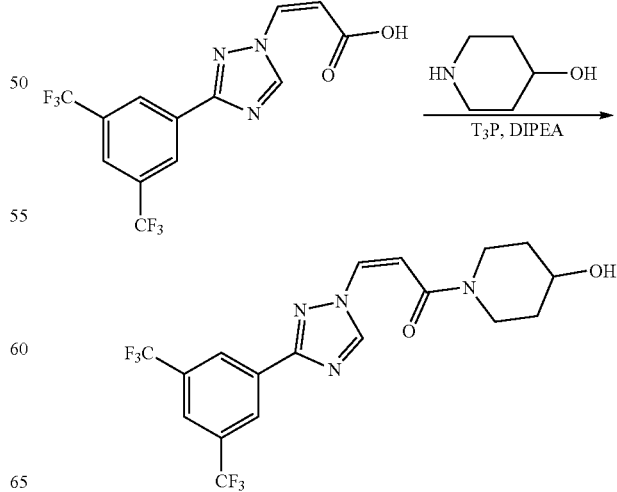

A 50-mL, 3-necked, round-bottomed flask was charged with a solution of (Z)-3-(3-(3,5-bis(trifluoromethyl)phenyl)-1H-1,2,4-triazol-1-yl)acrylic acid (0.20 g) in CH$_2$Cl$_2$ (10 mL). Piperidin-4-ol (0.07 g, 1.2 eq.) was added and the solution was cooled to −60° C. for the addition of T3P (propyl phosphonic anhydride) (0.40 mL, 1.2 eq.) and DIPEA (0.19 mL, 2.0 eq.). The reaction mixture was stirred for 30 min before being poured into water (50 mL) and extracted with CH$_2$Cl$_2$ (2×50 mL). The combined organic layers were washed with aqueous saturated brine (50 mL), dried over anhydrous MgSO$_4$, filtered, and concentrated under reduced pressure (25° C., 20 mmHg). Purification by column chromatography using silica 60/120 and MeOH:CH$_2$Cl$_2$ as mobile phase. (desired compound started eluting using 3.0% MeOH/CH$_2$Cl$_2$) afforded 0.025 g (yield: 10%) of (Z)-3-(3-(3,5-bis(trifluoromethyl)phenyl)-1H-1,2,4-triazol-1-yl)-1-(4-hydroxypiperidin-1-yl)prop-2-en-1-one. $^1$H NMR (400 MHz, CDCl$_3$) δ, 8.75 (s, 1H), 8.58 (s, 2H), 7.93 (s, 1H), 7.08-7.11 (d, J=10.4 Hz, 1H), 6.01-6.04 (d, J=10.4 Hz, 1H), 4.02-4.14 (m, 1H), 3.98-4.01 (m, 1H), 3.78-3.85 (m, 1H), 3.47-3.52 (s, 1H), 3.32-3.38 (s, 1H), 1.96 (s, 1H), 1.83 (s, 1H), 1.27 (s, 1H), 0.90 (s, 1H); LCMS for Chemical Formula: C$_{18}$H$_{17}$F$_6$N$_4$O$_2$ [M+H]$^+$ 435.34; found 435.24 (RT 2.408 min, purity: 89.6%).

Example 5: Synthesis of (Z)-3-(3-(3,5-bis(trifluoromethyl)phenyl)-1H-1,2,4-triazol-1-yl)-N-(pyrrolidin-1-yl)acrylamide (I-6)

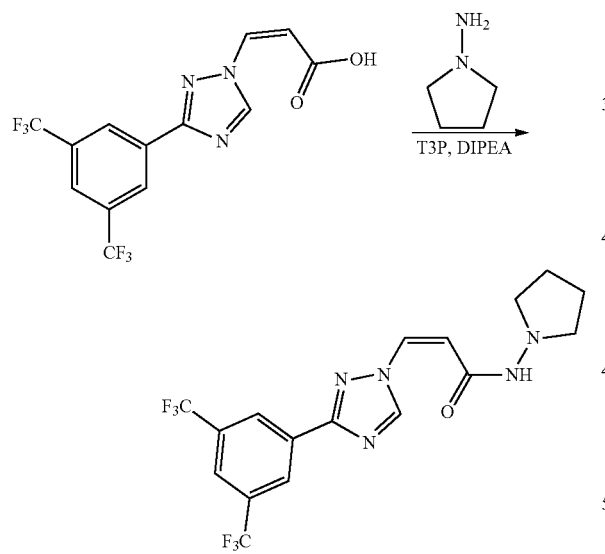

A cold (−40° C.) solution of (Z)-3-(3-(3,5-bis(trifluoromethyl)phenyl)-1H-1,2,4-triazol-1-yl)acrylic acid (0.35 g) in 1:1 CH$_2$Cl$_2$:EtOAc (200 mL) was treated with 1-aminopyrrolidine HCl (0.134 g). The mixture was then treated with T3P (50% in EtOAc; 0.77 ml, 1.3 eq.) followed by the slow addition of DIPEA (0.51 ml, 3.0 eq.). The reaction mixture was stirred for 30 min at −40° C. before being quenched with ice-water, and extracted with EtOAc (3×20 mL). The combined organic layers were washed with aqueous saturated brine, dried with anhydrous Na$_2$SO$_4$ and concentrated under reduced pressure (35° C., 20 mmHg) to afford 0.275 g of crude solid. Purification by column chromatography on silica gel (60-120 mesh size) using MeOH in CH$_2$Cl$_2$ as mobile phase afforded the pure desired (Z)-3-(3-(3,5-bis(trifluoromethyl)phenyl)-1H-1,2,4-triazol-1-yl)-N-(pyrrolidin-1-yl)acrylamide (7.0 mg yield: 1.7%): $^1$H NMR (400 MHz, DMSO-d6) δ, 9.49 (s, 1H), 8.95 (s, 1H), 8.53 (s, 2H), 8.28 (s, 1H), 7.4-7.38 (d, J=7.6 Hz, 1H), 5.87-5.84 (d, J=10.4 Hz, 1H), 2.86-2.81 (m, 4H), 1.74-1.73 (m, 4H); LCMS for C$_{17}$H$_{16}$F$_6$N$_5$O [M+H]$^+$ 420.33; found 420.13 (RT 7.76 min, purity: 92.4%).

Example 6: Synthesis of (Z)-3-(3-(3,5-bis(trifluoromethyl)phenyl)-1H-1,2,4-triazol-1-yl)-N'-methyl-N'-(pyridin-2-yl)acrylohydrazide (I-7)

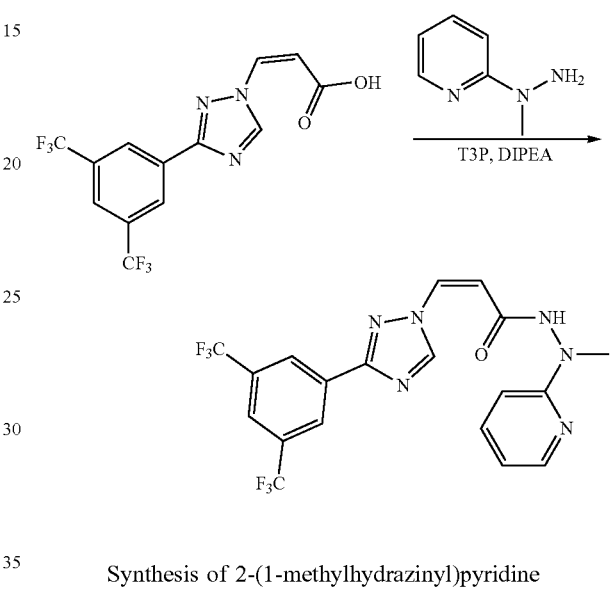

Synthesis of 2-(1-methylhydrazinyl)pyridine

A 25-mL, 3-necked, round-bottomed flask was charged with 2-bromopyridine (0.31 g) and methyl hydrazine (5.09 g, 34.2 eq.) under nitrogen atmosphere and the mixture was stirred and heated to reflux temperature at 80-85° C. for 1 hr. The reaction mixture was concentrated under reduced pressure (40° C., 20 mmHg) to afford a yellow oil that was treated with 10% w/v aqueous Na$_2$CO$_3$ and extracted with EtOAc. The organic layer was washed with aqueous saturated brine, dried over anhydrous Na$_2$SO$_4$, filtered and concentrated under reduced pressure (40° C., 20 mmHg) to afford a yellow oil (0.40 g), which was used as such in the following step.

A 50-mL, 3-necked, round-bottomed flask was charged with (Z)-3-(3-(3,5-bis(trifluoromethyl)phenyl)-1H-1,2,4-triazol-1-yl)acrylic acid (0.43 g), 2-(1-methylhydrazinyl)pyridine (0.15 g, 1.0 eq.) in EtOAc (10 mL). T3P (50% in EtOAc; 1.1 g, 1.5 eq.) and DIPEA (0.40 g, 2.5 eq.) were added under nitrogen atmosphere at −60° C. and the progress of the reaction was monitored by TLC (using 10% MeOH:CH$_2$Cl$_2$ as mobile phase and visualization with UV light). The reaction mixture was concentrated under reduced pressure (25° C., 20 mmHg) to afford 0.65 g of crude solid.

Purification was performed on Combi-Flash Column chromatography in CH$_2$Cl$_2$ and MeOH (desired compound started eluting at 3.3% MeOH in CH$_2$Cl$_2$). The fractions containing the desired compound were combined and concentrated under reduced pressure (35° C., 20 mm Hg) to afford 90.0 mg (yield: 18%) (Z)-3-(3-(3,5-bis(trifluoromethyl)phenyl)-1H-1,2,4-triazol-1-yl)-N'-methyl-N'-(pyridin-2-yl)acrylohydrazide. $^1$H NMR (400 MHz, DMSO-d6) δ 9.89 (s, 1H), 9.79 (brs, 1H), 8.57-8.62 (d, 2H), 7.92-7.94 (d, J=11.2 Hz, 1H), 7.59-7.64 (m, 1H), 7.19-7.25 (q, 1H), 6.75-6.89 (m, 2H), 5.85-5.88 (d, J=10.8 Hz, 1H), 3.46 (d, 3H); LCMS for C$_{19}$H$_{15}$F$_6$N$_6$O [M+H]$^+$ 457.35; found 456.26 (RT 2.52 min, purity: 100.0%).

Example 7: Synthesis of (Z)-3-(3-(3,5-bis(trifluoromethyl)phenyl)-1H-1,2,4-triazol-1-yl)-N'-methyl-N'-(pyrazin-2-yl)acrylohydrazide (I-8)

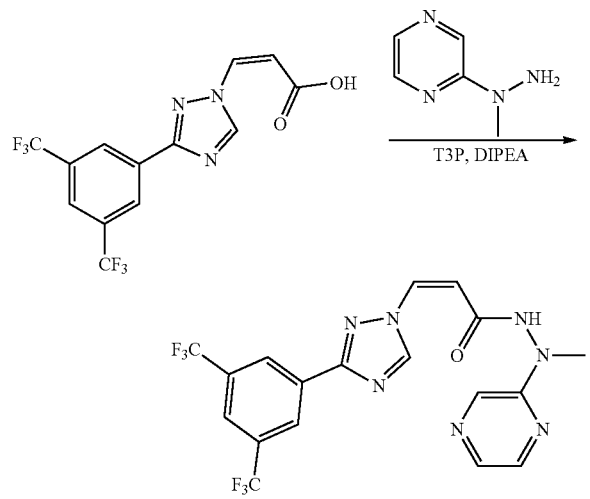

Synthesis of 2-(1-methylhydrazinyl)pyrazine

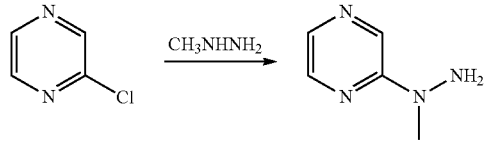

In a 25-mL, 3-necked, round-bottomed flask, 2-chloropyrazine (0.5 g) was dissolved in methyl hydrazine (0.5 g, 1.5 eq.) under nitrogen atmosphere at room temperature. Solid K$_2$CO$_3$ (0.9 g, 1.5 eq.) was added and the reaction mixture was stirred and heated to reflux at 80-85° C. for 1.0 h. The reaction mixture was then allowed to cool to RT and was concentrated under reduced pressure (40° C., 20 mmHg) to afford a yellow oily residue that was treated with 10% w/v aqueous Na$_2$CO$_3$ and extracted with EtOAc. The organic extract was washed with brine, dried over anhydrous Na$_2$SO$_4$, filtered and concentrated under reduced pressure (40° C., 20 mmHg) to afford yellow 0.43 g of a yellow oil that was used as such in the following step.

A 50-mL, 3-necked, round-bottomed flask was charged with (Z)-3-(3-(3,5-bis(trifluoromethyl)phenyl)-1H-1,2,4-triazol-1-yl)acrylic acid (0.3 g), 2-(1-methylhydrazinyl)pyrazine (0.12 g, 1.1 eq.) and CH$_2$Cl$_2$ (10 mL). T3P (50% in EtOAc; 0.38 g, 1.5 eq.) and DIPEA (0.50 g, 3.5 eq.) were added under nitrogen atmosphere at −60° C. monitoring the progress of the reaction by TLC (using 10% MeOH:CH$_2$Cl$_2$ as mobile phase and visualizing under UV light). The reaction mixture was concentrated under reduced pressure (25° C., 20 mmHg) to afford 0.265 g of solid crude. Purification using Combi-Flash Column chromatography using CH$_2$Cl$_2$:MeOH as eluent (desired compound started eluting at 1.5% MeOH in CH$_2$Cl$_2$) afforded 75.0 mg of pure compound (yield 23%); (Z)-3-(3-(3,5-bis(trifluoromethyl)phenyl)-1H-1,2,4-triazol-1-yl)-N'-methyl-N'-(pyrazin-2-yl)acrylohydrazide: $^1$H NMR (400 MHz, DMSO-d6) δ 10.77 (s, 1H), 9.40-9.36 (br s, 1H), 8.52 (s, 2H), 8.29-8.27 (d, 2H), 8.15 (s, 1H), 7.925-7.92 (d, 1H), 7.56-7.54 (d, J=10.4 Hz, 1H), 6.13-6.10 (d, J=10.4 Hz, 1H), 3.43 (d, 3H); LCMS for C$_{18}$H$_{14}$F$_6$N$_7$O [M+H]$^+$ 458.34; found 458.24 (RT 2.83 min; purity: 96.31%).

Example 8: Synthesis (Z)-3-(3-(3,5-bis(trifluoromethyl)phenyl)-1H-1,2,4-triazol-1-yl)-N'-methyl-N'-(3-methylpyridin-2-yl)acrylohydrazide (I-9)

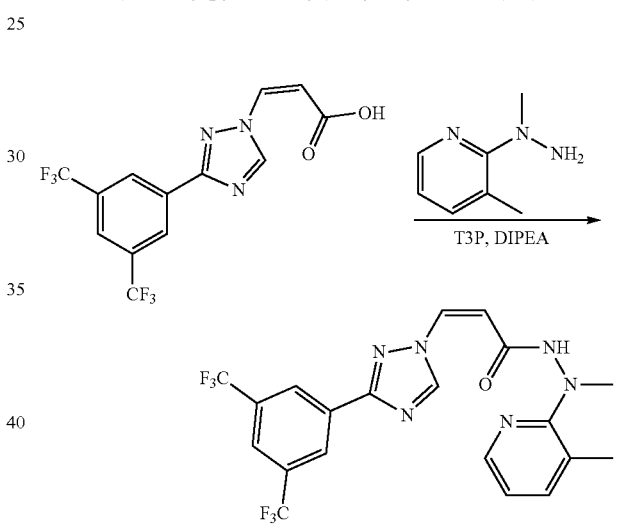

A 50-mL, 3-necked, round-bottomed flask was charged with a solution of (Z)-3-(3-(3,5-bis(trifluoromethyl)phenyl)-1H-1,2,4-triazol-1-yl)acrylic acid (0.25 g) in EtOAc (20 mL). The solution was cooled to −70° C. and was treated consecutively with 3-methyl-2-(1-methylhydrazinyl)pyridine (0.135 g, 1.0 eq.), T3P (50% in EtOAc; 1.4 mL, 4 eq.) and DIPEA (0.6 mL, 6 eq.). The clear reaction mixture was stirred at −60° C. for 4 hr. The progress of the reaction was followed by TLC analysis using 2.5% MeOH in CH$_2$Cl$_2$ as mobile phase and visualizing under UV. The reaction mixture was concentrated under reduced pressure (25° C., 20 mm Hg) to afford a crude compound that was purified by column chromatography (60/120 mesh SiO2 and eluting with a MeOH:CH$_2$Cl$_2$ gradient). The desired compound started eluting with 0.3-0.4% MeOH in dichloromethane. Fractions containing the desired material were combined to obtain 0.21 g (yield: 40%) (Z)-3-(3-(3,5-bis(trifluoromethyl)phenyl)-1H-1,2,4-triazol-1-yl)-N'-methyl-N'-(3-methylpyridin-2-yl)acrylohydrazide. $^1$H NMR (400 MHz, DMSO-d6) δ=10.73 (s, 1H), 9.32 (s, 1H), 8.52 (s, 2H), 8.45-8.46 (d, J=4.4 Hz, 1H), 8.29 (s, 1H), 7.97-7.99 (d, J=8 Hz, 1H), 7.48-7.50 (d, J=10 Hz, 1H), 7.01-7.05 (m, 1H), 5.86-5.88 (d, J=10 Hz, 1H), 3.26 (s, 3H); LCMS for $C_{20}H_{14}F_9N_6O$ [M+H]$^+$ 525.35; found 525.19 (RT 3.31 min, purity 99.40%).

Example 9: Synthesis of (Z)-3-(3-(3,5-bis(trifluoromethyl)phenyl)-1H-1,2,4-triazol-1-yl)-N'-(5-methylpyridin-2-yl)acrylohydrazide (I-10)

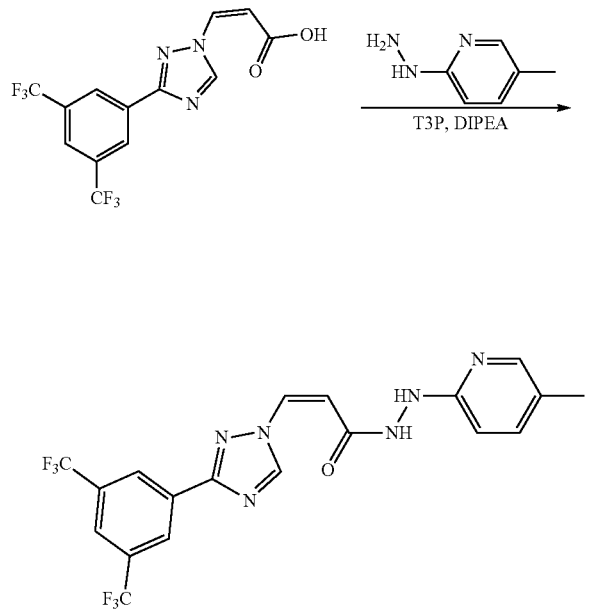

A 50-mL, 3-necked, round bottom flask, charged with a solution of (Z)-3-(3-(3,5-bis(trifluoromethyl)phenyl)-1H-1, 2,4-triazol-1-yl)acrylic acid (0.25 g) in EtOAc (10 mL) was treated with 2-hydrazinyl-5-methylpyridine (0.97 g, 1.1 eq.). The mixture was cooled to −60° C. and treated with T3P (propyl phosphonic anhydride; 0.85 mL, 2.0 eq.) and DIPEA (0.5 mL, 4.0 eq.). The mixture was stirred for 30 min then poured into water (50 mL) and extracted with $CH_2Cl_2$ (2×50 mL). The combined organic layers were washed with brine (50 mL), dried over anhydrous $MgSO_4$, filtered, and concentrated under reduced pressure (25° C., 20 mmHg) to afford a crude compound that was purified by column chromatography ($SiO_2$, 60/120 mesh, $MeOH:CH_2Cl_2$ as mobile phase). The desired compound started eluting with 2.5% $MeOH:CH_2Cl_2$. Fractions containing the desired compound were combined and concentrated under reduced pressure to afford 0.130 g (yield: 40%) (Z)-3-(3-(3,5-bis(trifluoromethyl)phenyl)-1H-1,2,4-triazol-1-yl)-N'-(5-methylpyridin-2-yl)acrylohydrazide. $^1$H NMR (400 MHz, CDCl$_3$) δ, 10.38 (s, exchangeable, 1H), 9.65 (s, 1H), 8.54 (s, 2H), 8.40 (s, exchangeable, 1H), 8.29 (s, 1H), 7.90 (s, 1H), 7.48-7.51 (d, J=10.4 Hz, 1H), 7.33-7.36 (dd, J=2 Hz, J=6 Hz, 1H), 6.61-6.63 (d, J=8.4 Hz, 1H), 6.20-6.23 (d, J=10.4 Hz, 1H), 2.15 (s, 3H); LCMS for $C_{19}H_{15}F_6N_6O$ [M+H]$^+$ 457.35; found 457.24 (RT 2.61 min, purity: 99.13%).

Example 10: Synthesis of (Z)-3-(3-(3,5-bis(trifluoromethyl)phenyl)-1H-1,2,4-triazol-1-yl)-N'-methyl-N'-(pyridin-3-yl)acrylohydrazide (I-11)

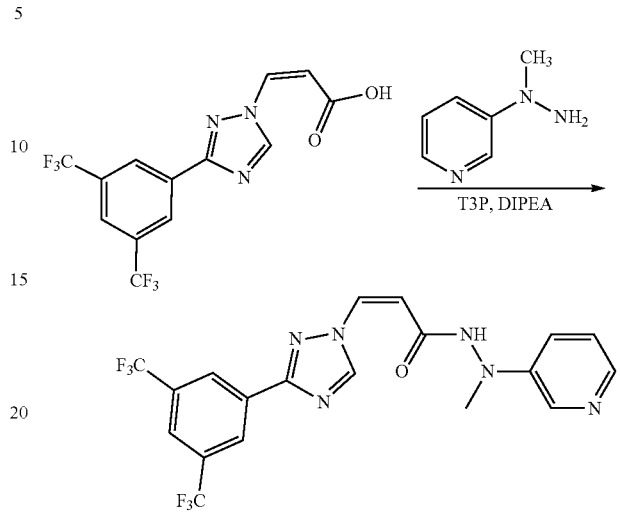

A 50-mL, 3-necked, round bottom flask charged with a solution of (Z)-3-(3-(3,5-bis(trifluoromethyl)phenyl)-1H-1, 2,4-triazol-1-yl)acrylic acid (0.25) in $CH_2Cl_2$ (12 mL) was treated with 3-(1-methylhydrazinyl)pyridine (0.105 g, 1.2 eq.). The mixture was cooled to −60° C. and treated with T3P (propyl phosphonic anhydride; 0.50 mL, 1.2 eq.) and DIPEA (0.24 mL, 2.0 eq.) and stirred for 1 h. The progress of the reaction was followed by TLC analysis using 10% $MeOH:CH_2Cl_2$ as mobile phase and visualizing under UV light. The reaction mixture was then poured into water (50 mL) and extracted with $CH_2Cl_2$ (2×50 mL). The combined organic layers were washed with brine (50 mL), dried over anhydrous $MgSO_4$, filtered, and concentrated under reduced pressure (25° C., 20 mmHg) to afford crude compound which was purified by column chromatography ($SiO_2$, 60/120 mesh, $MeOH:CH_2Cl_2$ as mobile phase). The desired compound started eluting in 3.0% $MeOH:CH_2Cl_2$. The fractions containing the compound were collected and concentrated under reduced pressure to afford 140 mg (yield: 43%) (Z)-3-(3-(3,5-bis (trifluoromethyl)phenyl)-1H-1,2,4-triazol-1-yl)-N'-methyl-N'-(pyridin-3-yl)acrylohydrazide.
$^1$H NMR (400 MHz, DMSO-d6) δ, 10.55 (s, 1H), 9.41 (s, 1H), 9.15 (s, 2H), 8.58 (s, 1H), 8.53 (s, 1H), 8.29 (s, 1H), 7.51-7.54 (d, J=10.4 Hz, 1H), 7.18-7.22 (m, 2H), 6.05-6.07 (d, J=10.4 Hz, 1H), 3.20 (s, 3H); LCMS for $C_{19}H_{15}F_6N_6O$ [M+H]$^+$ 457.35; found 457.19 (RT 2.43 min, purity: 83.48%).

Example 11: Synthesis of (Z)-3-(3-(3,5-bis(trifluoromethyl)phenyl)-1H-1,2,4-triazol-1-yl)-N'-(6-chloropyrimidin-4-yl)acrylohydrazide (I-12)

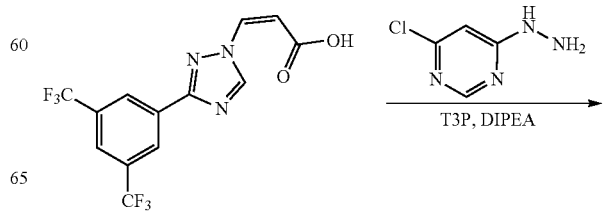

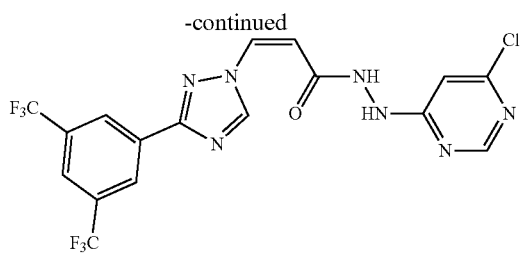

A 25-mL, 3-necked, round-bottomed flask was charged with a solution of (Z)-3-(3-(3,5-bis(trifluoromethyl)phenyl)-1H-1,2,4-triazol-1-yl)acrylic acid (0.5 g) and 4-chloro-6-hydrazinopyrimidine (0.20 g, 1.0 eq.) in EtOAc (5.0 mL). The mixture was cooled at −40° C. and treated with T3P (2.3 mL, 2.5 eq.) and DIPEA (0.98 mL, 4.0 eq.). TLC analysis (using 5% MeOH—CH$_2$Cl$_2$ as eluent) showed that the starting material was consumed after 30 min. The reaction mixture was then diluted with CH$_2$Cl$_2$, washed with water, dried over anhydrous Na$_2$SO$_4$, filtered and concentrated under reduced pressure (25° C., 20 mmHg) to afford crude material that was subjected to preparative TLC purification using 5% MeOH—CH$_2$Cl$_2$ with as the mobile phase. This afforded 250 mg (yield: 36.74%) (Z)-3-(3-(3,5-bis(trifluoromethyl)phenyl)-1H-1,2,4-triazol-1-yl)-N'-(6-chloropyrimidin-4-yl-)acrylohydrazide. $^1$H NMR (400 MHz, DMSO-d6), δ=10.59 (br s, exchangeable, 1H), 9.85 (br s, exchangeable, 1H), 9.52 (s, 1H), 8.50 (s, 2H), 8.38 (s, 1H), 8.27 (s, 1H), 7.52-7.55 (d, 1H, J=10.4 Hz), 6.69 (s, 1H), 6.05-6.08 (d, 1H, J=10.4 Hz); LCMS: Calculated for C$_{17}$H$_{11}$ClF$_6$N$_7$O (M+H)$^+$ 478.76; found: 478.09 (RT 2.79 min, purity: 97.51%).

Example 12: Synthesis of (Z)-3-(3-(3,5-bis(trifluoromethyl)phenyl)-1H-1,2,4-triazol-1-yl)-N'-(pyridin-3-yl)acrylohydrazide (I-13)

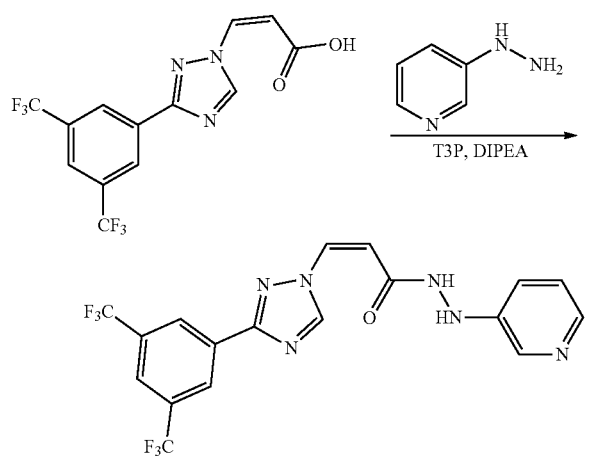

A 50-mL, 3-necked, round-bottomed flask was charged with (Z)-3-(3-(3,5-bis(trifluoromethyl)phenyl)-1H-1,2,4-triazol-1-yl)acrylic acid (0.25 g) and 3-hydrazinopyridine (0.077 g, 1.0 eq.) in EtOAc (10 mL). T3P (50% in EtOAc; 0.52 g, 1.2 eq.) and DIPEA (0.27 g, 2.0 eq.) were added under nitrogen atmosphere at −55 to −60° C. The progress of the reaction was followed by TLC analysis using 10% MeOH:CH$_2$Cl$_2$ as mobile phase and visualization under UV light. The reaction mixture was concentrated under reduced pressure (25° C., 20 mmHg) to afford 0.475 g of a crude solid. Purification was performed using Combi-Flash Column chromatography (with MeOH:CH$_2$Cl$_2$). The desired compound started eluting at 2.3% MeOH in CH$_2$Cl$_2$. The fractions containing the compound were combined and concentrated under reduced pressure (35° C., 20 mmHg) to afford 20.0 mg (yield: 6%) (Z)-3-(3-(3,5-bis(trifluoromethyl)phenyl)-1H-1,2,4-triazol-1-yl)-N'-(pyridin-3-yl)acrylohydrazide. $^1$H NMR (400 MHz, DMSO-d6) δ 10.35 (s, 1H), 9.66 (s, 1H), 8.53 (s, 2H), 8.28 (s, 1H), 8.24 (s, 1H), 8.13 (s, 1H), 7.93-7.95 (m, 1H), 7.52-7.54 (d, J=10.4 Hz, 1H), 7.09-7.15 (m, 2H), 6.04-6.07 (d, J=10.4 Hz, 1H), LCMS for C$_{18}$H$_{13}$F$_6$N$_6$O [M+H]$^+$ 443.33 found 443.19 (RT 2.19 min, purity: 99.60%).

Example 13: Synthesis of (Z)-3-(3-(3,5-bis(trifluoromethyl)phenyl)-1H-1,2,4-triazol-1-yl)-N'-(quinoxalin-2-yl)acrylohydrazide (I-14)

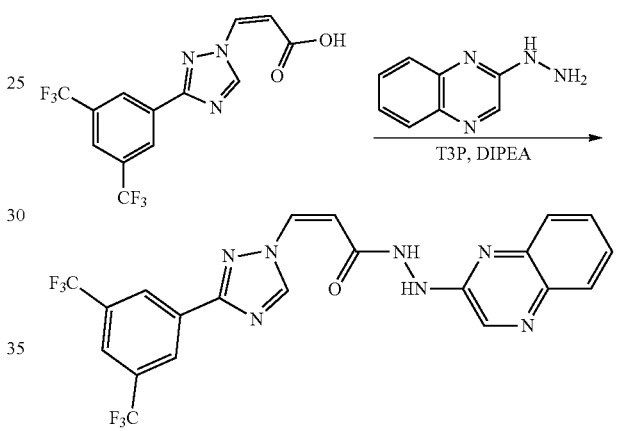

Synthesis of 2-hydrazinylquinoxaline

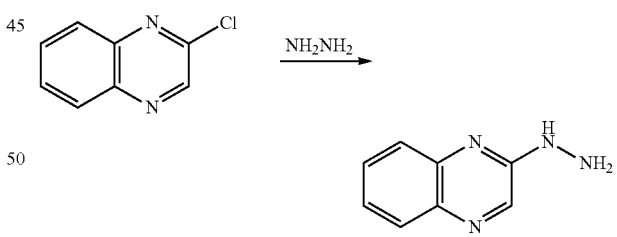

In a 30-mL sealed tube, 2-chloroquinoxaline (1.0 g) was dissolved in ethanol (8 mL) and hydrazine hydrate (8 mL) was added under nitrogen atmosphere at room temperature. The mixture was stirred and heated to reflux temperature (80° C.) for 1 hr. The progress of the reaction was followed by TLC analysis using 10% MeOH:CH$_2$Cl$_2$ as mobile phase and visualization under UV light and/or with ninhydrin. The reaction mixture was concentrated under reduced pressure (40° C., 20 mmHg) to afford 240 mg of a white solid, which was used as such in the following step.

A 50-mL, 3-necked, round-bottomed flask was charged with a solution of (Z)-3-(3-(3,5-bis(trifluoromethyl)phenyl)-1H-1,2,4-triazol-1-yl)acrylic acid (0.25 g) and 2-hydrazinylquinoxaline (0.14 g, 1.2 eq.) in EtOAc. T3P (50% in EtOAc; 0.83 mL, 2.0 eq.) and DIPEA (0.5 mL, 4.0 eq.) were added under nitrogen atmosphere at −55 to −60° C. and the reaction mixture was stirred for 2 hr before being concentrated under reduced pressure (25° C., 20 mmHg) to afford 0.150 g of crude solid. Purification using Combi-Flash column chromatography (eluting with MeOH:CH$_2$Cl$_2$; desired compound started eluting at 5% MeOH in CH$_2$Cl$_2$) afforded 60 mg (yield: 20%) (Z)-3-(3-(3,5-bis(trifluoromethyl)phenyl)-1H-1,2,4-triazol-1-yl)-N'-(quinoxalin-2-yl)acrylohydrazide. $^1$H NMR (400 MHz, DMSO-d6) δ=10.851 (s, 1H), 9.89-9.87 (s, 1H), 9.67 (s, 1H), 8.49-8.54 (m, 3H), 8.26 (s, 1H), 8.28 (s, 1H), 7.86-7.88 (d, J=8 Hz, 1H), 7.45-7.66 (m, 4H), 6.17-6.20 (d, J=10.4 Hz, 1H); LCMS for C$_{21}$H$_{14}$F$_6$N$_7$O [M+H]$^+$ 494.37; found 494.19 (RT 2.88 min, purity: 100%).

Example 14: Synthesis of (Z)-3-(3-(3,5-bis(trifluoromethyl)phenyl)-1H-1,2,4-triazol-1-yl)-N'-(1,1-dioxotetrahydrothiophen-3yl)acrylohydrazide (I-15)

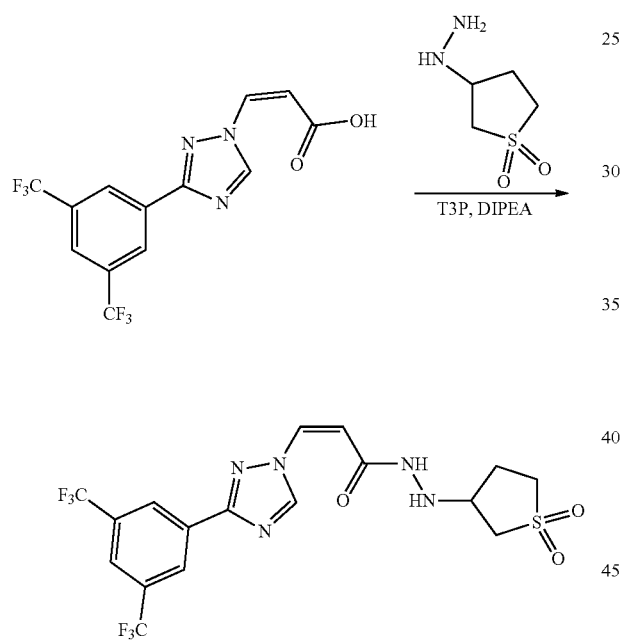

A 50-mL, 3-necked, round-bottomed flask charged with a solution of (Z)-3-(3-(3,5-bis(trifluoromethyl)phenyl)-1H-1,2,4-triazol-1-yl)acrylic acid (0.5 g) in EtOAc (20.0 mL) was treated with 2-(1,1-dioxotetrahydrothiophen-3-yl)hydrazine (0.3 g, 1.2 eq.). The mixture was cooled to −60° C. and treated simultaneously with T3P (50% in EtOAc; 2.0 mL, 2 eq.) and DIPEA (1 mL, 4 eq.). The reaction mixture was stirred for 30 min at −60° C. before being concentrated under reduced pressure (35° C., 20 mmHg) to afford 0.60 g of a solid residue. Purification by column chromatography (SiO2; elution with MeOH:CH$_2$Cl$_2$; desired compound eluted at 5% MeOH in CH$_2$Cl$_2$) afforded 100 mg (yield=15%) (Z)-3-(3-(3,5-bis(trifluoromethyl)phenyl)-1H-1,2,4-triazol-1-yl)-N'-(tetrahydrothiophen-1-1-dioxide-3-yl)acrylohydrazide. $^1$H NMR (400 MHz, CD3OD) δ=9.57 (s, 1H), 8.64 (s, 2H), 8.10 (s, 1H), 7.34-7.36 (d, J=10.4 Hz, 1H), 5.89-5.92 (d, J=10.8 Hz, 1H), 4.01 (m, 1H), 3.04-3.26 (m, 4H), 2.27-2.34 (m, 2H). LCMS for C$_{17}$H$_{15}$F$_6$N$_5$O$_3$S [M+H]$^+$ 484.40; found 483.39 (RT 2.63 min, purity: 66.39%).

Example 15: Synthesis of (Z)—N-(azepan-1-yl)-3-(3-(3,5-bis(trifluoromethyl)phenyl)-1H-1,2,4-triazol-1-yl)acrylamide (I-16)

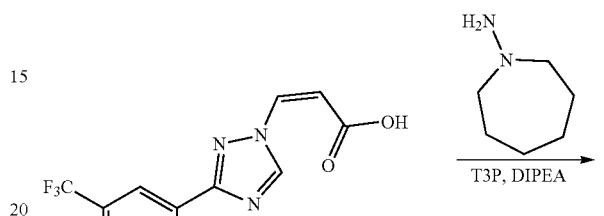

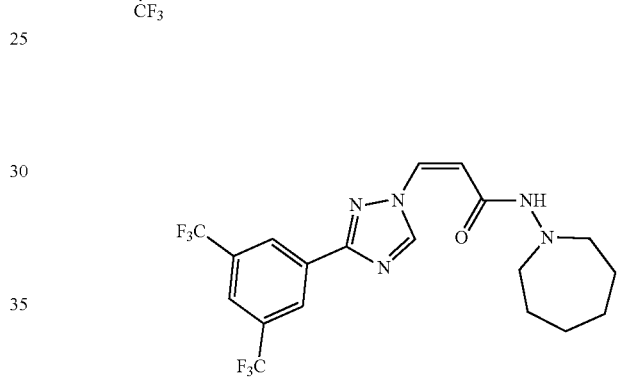

A 500-mL, 3-necked, round-bottomed flask was charged with a solution of (Z)-3-(3-(3,5-bis(trifluoromethyl)phenyl)-1H-1,2,4-triazol-1-yl)acrylic acid (0.3 g) in CH2Cl2:EtOAc (1:1, 200 mL) and the solution was treated with azepan-1-amine (0.137 g) at room temperature. The mixture was cooled to −60° C. and treated first with T3P (50% in EtOAc, 0.78 ml) and then with DIPEA (0.58 mL). The reaction mixture was stirred for 30 min at −60° C. before being quenched with ice-cold water and extracted with EtOAc (3×20 mL). The combined organic extracts were washed with brine, dried over anhydrous Na2SO4, filtered and concentrated under reduced pressure (35° C., 20 mmHg) to afford 0.57 g of solid. Purification by column chromatography (SiO2, MeOH:CH$_2$Cl$_2$ as mobile phase; compound started eluting with 0.1% MeOH in CH$_2$Cl$_2$) afforded 90 mg (yield: 24%) (Z)—N-(azepan-1-yl)-3-(3-(3,5-bis(trifluoromethyl)phenyl)-1H-1,2,4-triazol-1-yl)acrylamide. $^1$H NMR (400 MHz, DMSO-d6) δ, 9.61 (s, 1H), 9.49 (s, 1H), 9.14 (s, 1H), 8.52 (s, 2H), 8.28 (s, 1H), 7.39-7.97 (d, J=10 Hz, 1H), 6.52-6.49 (d, J=10.4 Hz, 1H), 5.86-5.83 (d, J=10.4 Hz, 1H), 3.00-2.97 (m, 4H), 1.58-1.54 (m, 8H) LCMS for C$_{19}$H$_{19}$F$_6$N$_5$O [M+H]$^+$ 448.39; found 448.30 at RT 3.22 min purity (96.48%).

Example 16: Synthesis of (Z)-3-(3-(3,5-bis(trifluoromethyl)phenyl)-1H-1,2,4-triazol-1-yl)-N'-(2,6-dimethylpyrimidin-4-yl)acrylohydrazide (I-17)

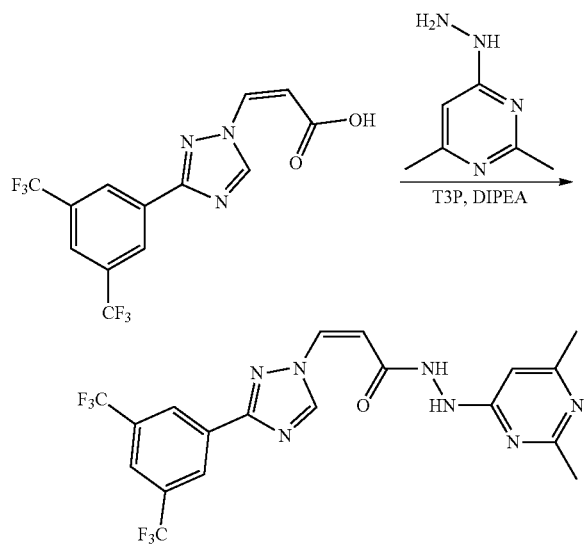

A 50-mL, 3-necked, round-bottomed flask was charged with a solution of (Z)-3-(3-(3,5-bis(trifluoromethyl)phenyl)-1H-1,2,4-triazol-1-yl)acrylic acid (0.20 g.) dissolved in ethyl acetate (15 mL). The solution was cooled to −40° C. and treated with 4-hydrazinyl-2,6-dimethylpyrimidine (0.078 g, 1 eq.). T3P (50% in EtOAc; 0.7 g, 3.0 eq.) and DIPEA (0.367 g, 4.0 eq.) were then added simultaneously and the reaction mixture was stirred for 30 min at −40° C. The reaction mixture was then allowed to warm to room temperature and was concentrated under reduced pressure (35° C., 20 mmHg) to afford 0.340 g of oily crude compound that was purified by combi-flash using MeOH:CH$_2$Cl$_2$ as mobile phase (the desired compound was eluted with 7-8% MeOH in CH$_2$Cl$_2$) to afford 50 mg (yield: 18%) (Z)-3-(3-(3,5-bis(trifluoromethyl)phenyl)-1H-1,2,4-triazol-1-yl)-N'-(2,6-dimethylpyrimidin-4-yl)acrylohydrazide. $^1$H NMR (400 MHz, DMSO-d6) δ, 10.54 (s, 1H), 9.19 (b, 1H), 8.54 (s, 2H), 8.30 (s, 1H), 7.52-7.55 (d, J=10.4, 1H), 6.29 (s, 1H), 6.06-6.08 (d, J=10.4, 1H), 2.33 (s, 3H), 2.13 (s, 3H), LCMS for C$_{19}$H$_{15}$F$_6$N$_7$O [M+H]$^+$ 472.37; found 472.24 (RT 2.88 min, purity: 99.59%).

Example 17: Synthesis of (E)-3-(3-(3,5-bis(trifluoromethyl)phenyl)-1H-1,2,4-triazol-1-yl)-N'-(pyrazin-2-yl)acrylohydrazide

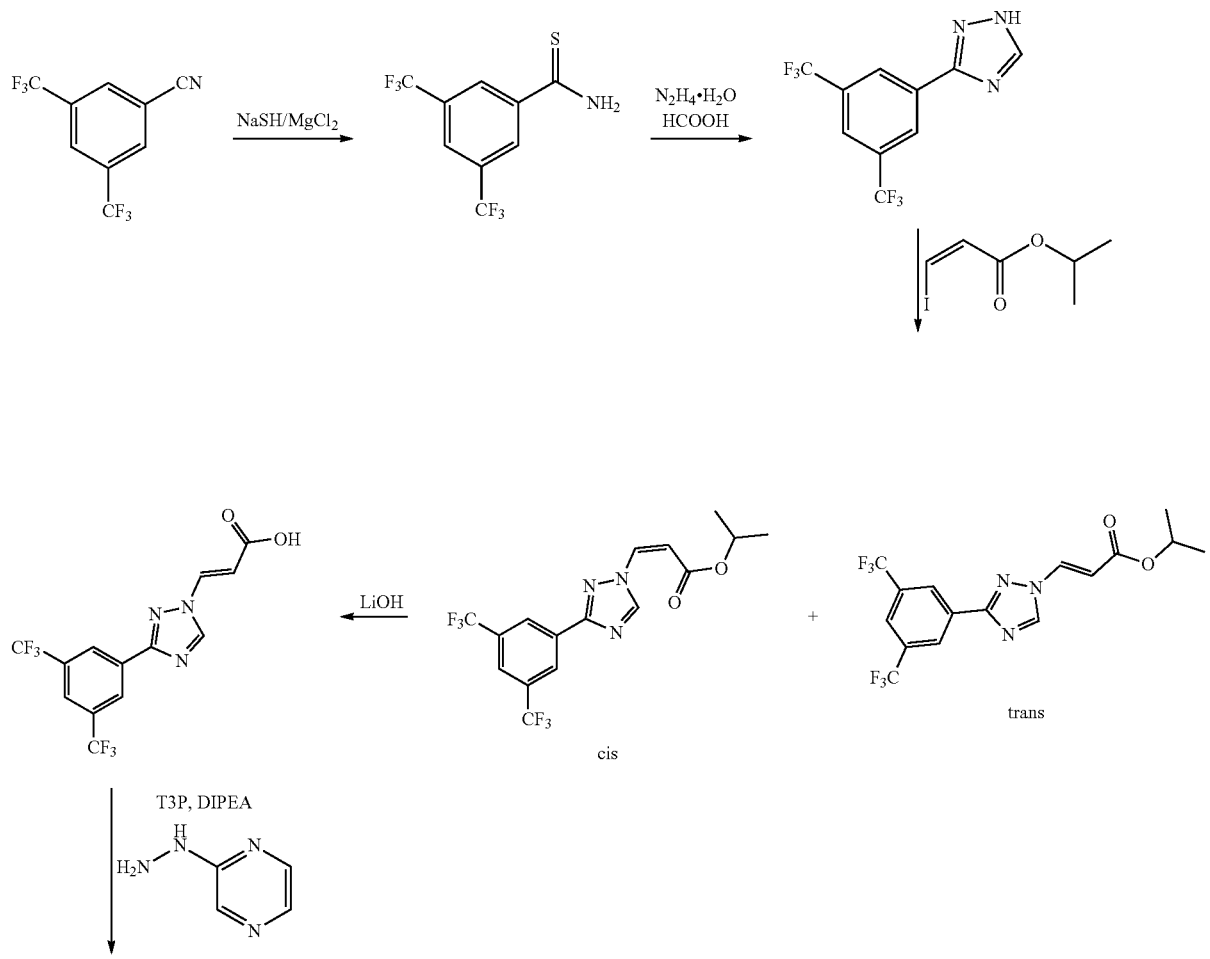

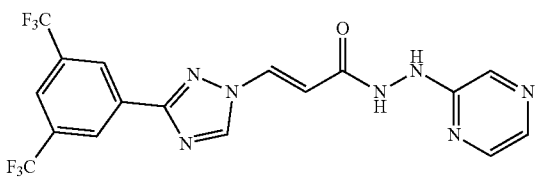

Synthesis of 3,5-bis(trifluoromethyl)benzothioamide

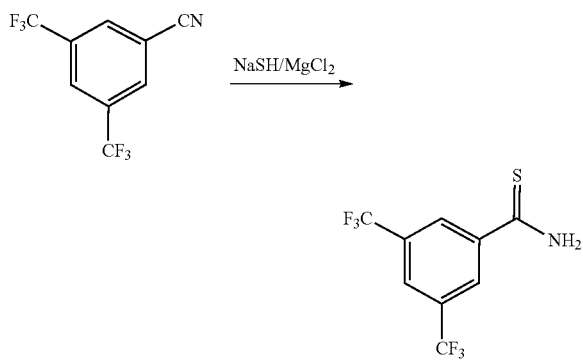

A 2-L, 3-necked, round-bottomed flask, charged with a solution of 3,5-bis(trifluoromethyl)benzonitrile (200 g) in DMF (1 L), was treated with NaSH (123.7 g, 2.0 eq.) and MgCl₂ (186.7 g, 1 eq.). The reaction mixture was stirred at RT for 3 h before being poured into an ice-water slurry (10 L) and was extracted with EtOAc (3×1 L). The combined organic extracts were washed with brine (3×100 mL), dried over anhydrous Na₂SO₄, filtered, and concentrated under reduced pressure (25° C., 20 mmHg) to afford 205 g of crude compound (yield: 90%), which was used in the following step without further purification.

Synthesis of 3-(3,5-bis(trifluoromethyl)phenyl)-1H-1,2,4-triazole

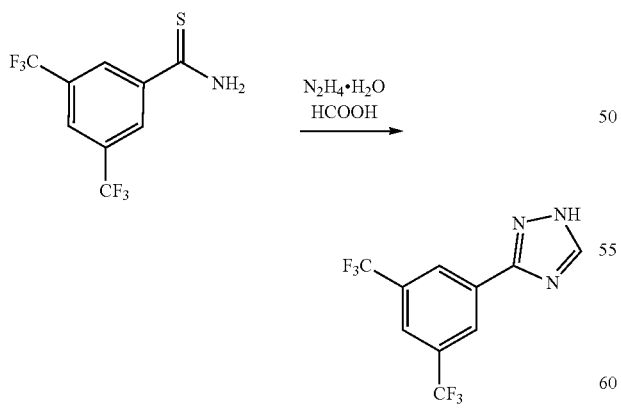

A 5-L, 3-necked, round-bottomed flask, charged with a solution of 3,5-bis(trifluoromethyl)benzothioamide (205.65 g) in DMF (1.03 L) was treated with hydrazine hydrate (73.16 mL, 2.0 eq.) added dropwise. The reaction mixture was stirred at room temperature for 1 h before being treated with HCOOH (1.028 L) added dropwise. The reaction mixture was refluxed at 90° C. for 3 h then cooled to room temperature and poured into saturated aqueous NaHCO₃ solution (7 L) and extracted with EtOAc (3×1 L). The combined organic layers were washed with brine (3×500 mL), dried over anhydrous Na₂SO₄, filtered, and concentrated under reduced pressure (35° C., 20 mmHg) to afford 180 g of a solid. The solid was suspended in petroleum ether and the suspension was stirred, filtered and dried to afford the desired triazole as a pale yellow solid (160 g, yield: 75%).

Synthesis of (Z)-isopropyl 3-(3-(3,5-bis(trifluoromethyl)phenyl)-1H-1,2,4-triazol-1-yl)acrylate and (E)-isopropyl 3-(3-(3,5-bis(trifluoromethyl)phenyl)-1H-1,2,4-triazol-1-yl)acrylate

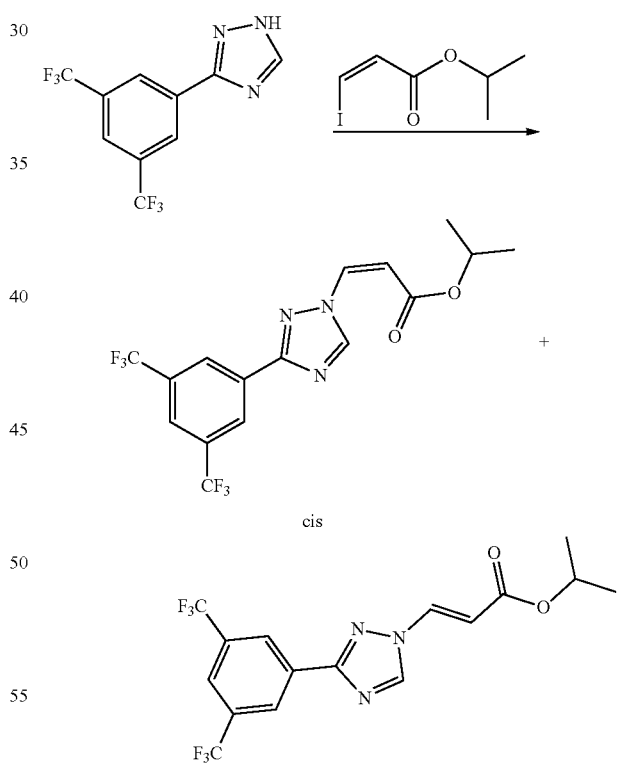

A 2-L, 3-necked, round-bottomed flask, charged with a solution of 3-(3,5-bis(trifluoromethyl)phenyl)-1H-1,2,4-triazole (160 g,) in DMF (0.96 L, 6V), was treated with DABCO (127.74 g, 2 eq.) and stirred for 30 min. (Z)-isopropyl 3-iodoacrylate (150.32 g, 1.1 eq.) was added dropwise to the above reaction mixture and stirred for 1 h before being poured into an ice-water slurry (5 L) and extracted with EtOAc (3×1 L). The combined organic extracts were washed with brine (3×100 mL), dried over anhydrous Na₂SO₄, filtered, and concentrated under reduced pressure (35° C., 20 mmHg) to afford 250 g of crude compound. Purification by column chromatography (SiO2, 60/120 mesh, elution with EtOAc:hexanes gradient; the desired compounds started eluting in 2-2.5% EtOAc in hexanes) afforded pure cis ester (138 g, yield: 61.6%) and pure trans ester (11.6 g, yield: 5.2%).

Synthesis of (E)-3-(3-(3,5-bis(trifluoromethyl)phenyl)-1H-1,2,4-triazol-1-yl)acrylic acid

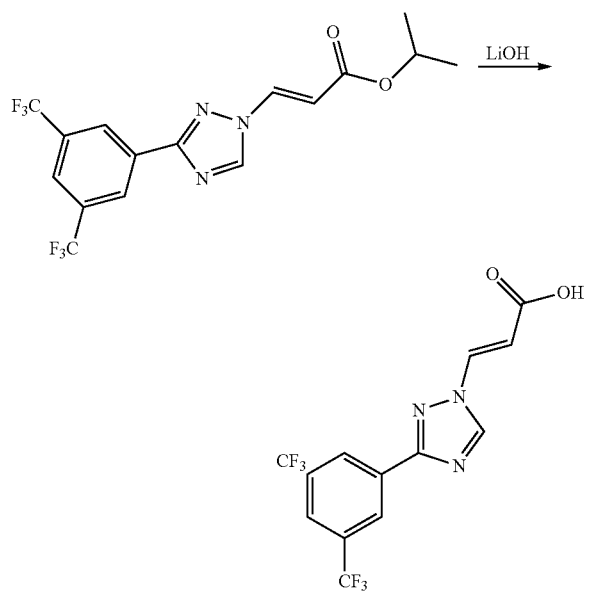

A 500-mL, 3-necked, round-bottomed flask was charged with a solution of (E)-isopropyl 3-(3-(3,5-bis(trifluoromethyl)phenyl)-1H-1,2,4-triazol-1-yl)acrylate (5.0 g) in THF (50 mL). The solution was treated with a solution of LiOH (2.66 g, 5.0 eq.) in water (50 mL) and the reaction mixture was stirred at room temperature for 4 h. before being diluted with 40 mL water, acidified (pH=2-3) with dilute aqueous HCl and extracted with EtOAc (3×100 mL). The organic extract was washed with brine, dried over anhydrous Na₂SO₄, filtered and concentrated under reduced pressure to afford 2.75 g of the desired unsaturated carboxylic acid (yield: 61.6%, purity: 99.0% by LCMS).

Synthesis of (E)-3-(3-(3,5-bis(trifluoromethyl)phenyl)-1H-1,2,4-triazol-1-yl)-N'-(pyrazin-2-yl)acrylohydrazide

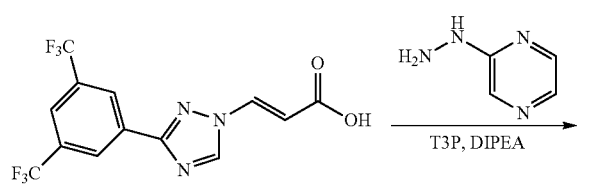

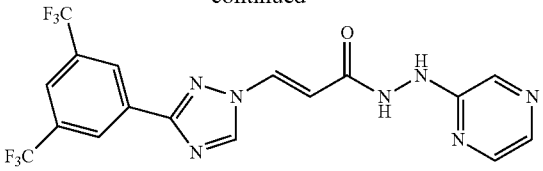

To a solution of (E)-3-(3-(3,5-bis(trifluoromethyl)phenyl)-1H-1,2,4-triazol-1-yl)acrylic acid (0.75 g,) in EtOAc (25 mL) and THF (12.5 mL) was added a solution of 2-hydrazinopyrazine (0.23 g) in 12 mL THF at room temperature. T3P (50% in ethyl acetate, 1.52 mL) and DIPEA (1.46 mL) were added dropwise and simultaneously and the reaction mixture was stirred for 30 min at room temperature before being quenched with ice-cold water and extracted with EtOAc (3×25 mL). The combined organic layers were washed with brine, dried over anhydrous Na₂SO₄ and concentrated under reduced pressure (35° C., 20 mmHg), affording 0.698 g of a crude solid. Trituration first with petroleum ether then with Et20 afforded 275 mg (yield: 29%) (E)-3-(3-(3,5-bis(trifluoromethyl) phenyl)-1H-1,2,4-triazol-1-yl)-N'-(pyrazin-2-yl)acrylohydrazide. ¹H NMR (400 MHz, DMSO-d6) δ, 10.3 (s, 1H), 9.15 (s, 2H), 8.59 (s, 2H), 8.30-8.26 (d, J=14.8 Hz, 1H), 8.13 (s, 1H), 8.06-8.07 (m, 1H), 6.98-6.95 (d, J=13.4 Hz, 1H); LCMS for $C_{17}H_{12}F_6N_7O$ [M+H]⁺ 443.31; found 444.19 (RT 2.625 min, purity: 99.06%).

Example 18: Synthesis of (Z)-3-(3-(3,5-bis(trifluoromethyl)phenyl)-1H-1,2,4-triazol-1-yl)-N'-(pyridin-4-yl)acrylohydrazide hydrochloride (I-19)

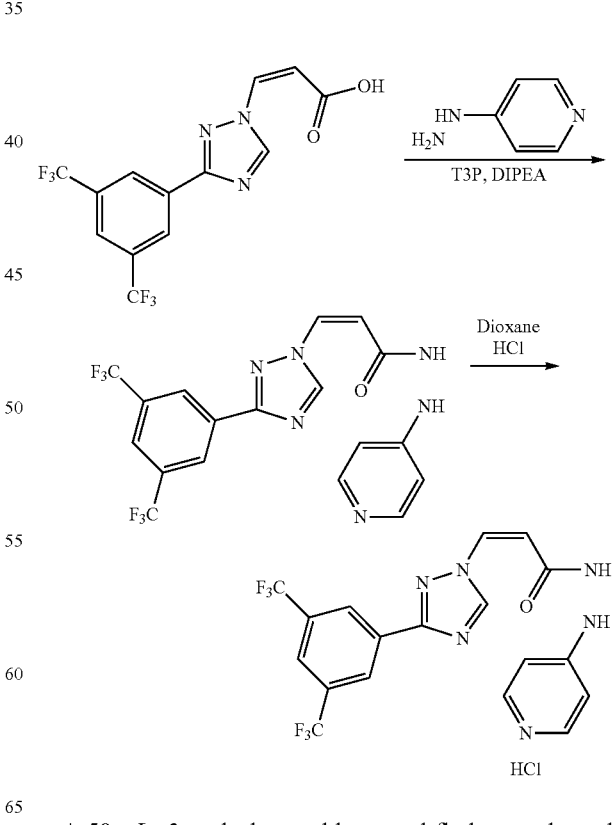

A 50-mL, 3-necked, round-bottomed flask was charged with (Z)-3-(3-(3,5-bis(trifluoromethyl)phenyl)-1H-1,2,4-triazol-1-yl)acrylic acid (0.25 g) and EtOAc (10.0 mL). 4-Hydrazinylpyridine hydrochloride (0.16 g, 1.2 eq.) was added at −40° C. followed by the simultaneous addition of T3P (50% in EtOAc, 0.85 mL, 2.0 eq.) and DIPEA (0.49 mL, 4.0 eq.). The reaction mixture was stirred for 30 min at −40° C. before being concentrated under reduced pressure (35° C., 20 mmHg) to afford 0.35 g of crude material. Purification by column chromatography using MeOH:CH$_2$Cl$_2$ as a mobile phase (compound was eluted with 4% MeOH in CH$_2$Cl$_2$) afforded 80 mg (yield: 29.85%) (Z)-3-(3-(3,5-bis(trifluoromethyl)phenyl)-1H-1,2,4-triazol-1-yl)-N'-(pyridin-4-yl) acrylohydrazide. $^1$H NMR (400 MHz, DMSO-d6) δ, 10.53 (br s, NH exchangeable, 1H), 9.58 (s, 1H), 8.88 (br s, NH exchangeable, 1H), 8.84 (s, 2H), 8.29 (s, 1H), 8.09-8.11 (d, 2H), 7.52-7.54 (d, J=10.4 Hz, 1H), 6.66-6.69 (m, 2H), 6.06-6.10 (d, J=14.4 Hz, H); LCMS for C$_{15}$H$_{13}$F$_6$N$_6$O [M+H]$^+$ 443.33; found 443.24 (RT 2.241 min, purity: 90.17%).

A 25-mL, 3-necked, round-bottomed flask was charged with a cold (0° C.) solution of (Z)-3-(3-(3,5-bis(trifluoromethyl)phenyl)-1H-1,2,4-triazol-1-yl)-N'-(pyridin-4-yl)acrylohydrazide (0.08 g) in CH$_2$Cl$_2$ (5.0 mL) and treated with 4N HCl in dioxane (0.5 mL). The reaction mixture was allowed to warm to room temperature and stirred for 4 h before being concentrated under reduced pressure (35° C., 20 mmHg) to afford 0.05 g (yield: 40.81%) (Z)-3-(3-(3,5-bis(trifluoromethyl)phenyl)-1H-1,2,4-triazol-1-yl)-N'-(pyridin-4-yl)acrylohydrazide-HCl salt. $^1$H NMR (400 MHz, DMSO-d6) δ 13.67 (br s, exchangeable, 1H), 10.67 (s, exchangeable, 1H), 9.43 (s, 1H), 8.58 (s, 2H), 8.35-8.38 (m, 4H), 7.60-7.62 (d, J=10.4 Hz, 1H), 6.92-6.96 (m, 2H), 611-6.13 (d, J=10.4 Hz, 1H); LCMS for C$_{18}$H$_{13}$F$_6$N$_6$O [M+H]$^+$ 443.33; found 443.24 (RT 3.00 min, purity: 90.97%).

Example 19: Synthesis of (Z)—N-(4-benzylpiperazin-1-yl)-3-(3-(3,5-bis(trifluoromethyl)phenyl)-1H-1,2,4-triazol-1-yl)acrylamide (I-20)

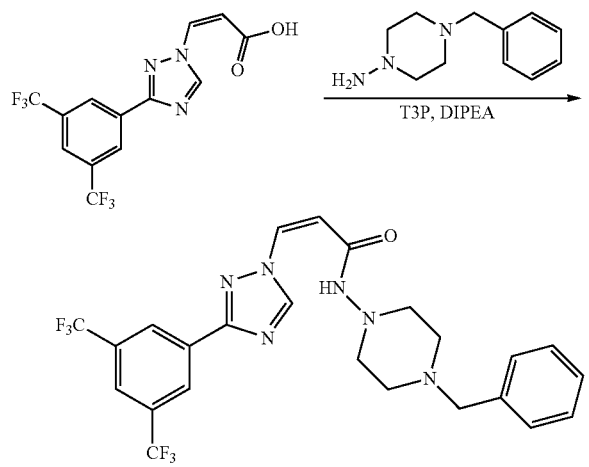

Synthesis of 4-benzylpiperazin-1-amine

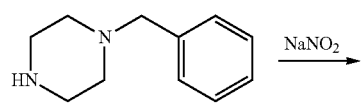

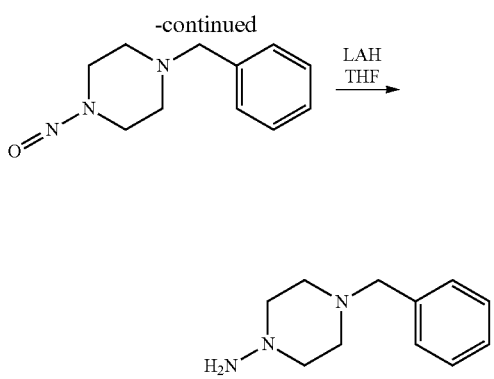

A 50-mL, 3-necked, round-bottomed flask was charged with conc. HCl and water, and the solution was cooled at 0-5° C. for the addition of NaNO$_2$ and benzyl piperazine (5.0 g) under a nitrogen atmosphere. The reaction mixture was stirred for 2.5 h at 0-5° C. before being diluted with water and extracted with EtOAc (3×100 mL). The combined organic extracts were dried over anhydrous Na$_2$SO$_4$, filtered and concentrated under reduced pressure (40° C., 20 mmHg) to afford 4.40 g a colorless solid. Purification using combi-flash chromatography (elution with 25.5% EtOAc:hexane) afforded 2.0 g of desired compound (yield: 34.3%).

A cold (−70° C.) solution of 1-benzyl-4-nitroso-4-piperizine (0.8 g) in THF was treated with excess LAH under a nitrogen atmosphere. The reaction mixture was allowed to warm up to ambient temperature and stirred 1.0 h before being quenched with water and extracted with EtOAc (3×10 mL). The combined organic extracts were dried over anhydrous Na$_2$SO$_4$, filtered and concentrated under reduced pressure (40° C., 20 mmHg) to afford 0.70 g 4-benzylpiperazin-1-amine as a colorless solid.

Synthesis of (Z)—N-(4-benzylpiperazin-1-yl)-3-(3-(3,5-bis(trifluoromethyl)phenyl)-1H-1,2,4-triazol-1-yl)acrylamide A 50-mL, 3-necked, round-bottomed flask was charged with (Z)-3-(3-(3,5-bis(trifluoromethyl)phenyl)-1H-1,2,4-triazol-1-yl)acrylic acid (0.220 g, 1.2 eq.), 4-benzylpiperazin-1-amine (0.10 g, 1.0 eq.) and EtOAc (15 ml). T3P (50% in EtOAc 0.99 g, 3.0 eq.) and DIPEA (0.27 mg, 4.0 eq.) were added under nitrogen atmosphere to the cold (−60° C.) solution. The progress of the reaction was followed by TLC analysis (SiO$_2$, 15% MeOH:CH$_2$Cl$_2$ as mobile phase, visualization under UV light). The reaction mixture was quenched in water and extracted with ethyl acetate (3×15 mL). The combined organic extracts were dried over anhydrous Na$_2$SO$_4$, filtered and concentrated under reduced pressure (25° C., 20 mmHg) to afford 0.35 g of crude solid. Purification on Combi-flash (eluting with 10% MeOH/CH$_2$Cl$_2$) afforded 20 mg (yield: 6%) (Z)—N-(4-benzylpiperazin-1-yl)-3-(3-(3,5-bis(trifluoromethyl)phenyl)-1H-1,2,4-triazol-1-yl)acrylamide. $^1$H NMR (400 MHz, DMSO-d6) δ 9.44-9.48 (t, 3H), 9.10 (s, 1H), 8.51 (s, 2H), 7.23-7.41 (m, 6H), 6.46-6.49 (d, J=10.4 Hz, 1H), 5.83-5.86 (d, J=10.4 Hz, 1H), 3.47 (s, 2H), 2.81 (s, 4H), 2.23-2.33 (d, 2H) LCMS for C$_{24}$H$_{23}$F$_6$N$_6$O [M+H]$^+$ 525.47; found 525.20 (RT 9.87 min, purity: 100%).

Example 20: Synthesis of (Z)-3-(3-(3,5-bis(trifluoromethyl)phenyl)-1H-1,2,4-triazol-1-yl)-N-(4-ethylpiperazin-1-yl)acrylamide (I-21)

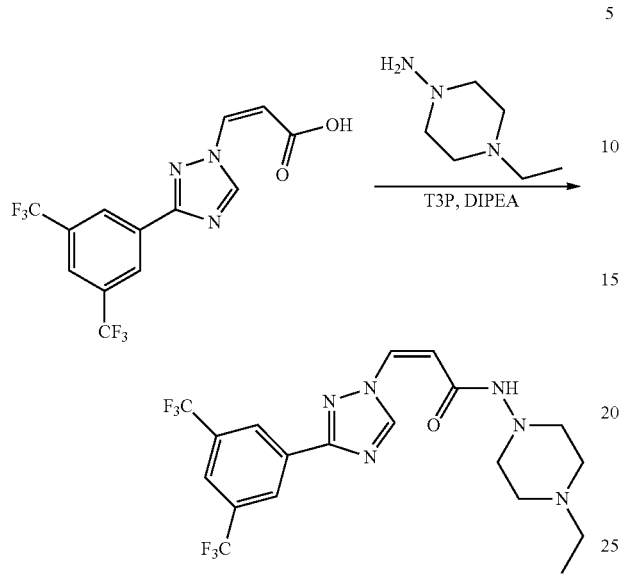

A cold (−40° C.) solution of (Z)-3-(3-(3,5-bis(trifluoromethyl)phenyl)-1H-1,2,4-triazol-1-yl)acrylic acid (0.25 g) in EtOAc (20 mL) was treated with 4-ethylpiperazin-1-amine (0.12 g). T3P (50% in EtOAc, 0.84 mL) and DIPEA (0.24 mL) were added simultaneously and the reaction mixture was stirred for 30 min at −40° C. before being quenched with ice-cold water and extracted with EtOAc (3×20 mL). The combined organic extracts were washed with brine, dried over anhydrous Na$_2$SO$_4$ and concentrated under reduced pressure (35° C., 20 mmHg) to afford 0.280 g of crude compound. Purification by combi-flash chromatography (eluting with 2% MeOH in CH$_2$Cl$_2$) followed by purification on a preparative TLC plate (eluting with 10% MeOH in CH$_2$Cl$_2$) afforded 60 mg (Z)-3-(3-(3,5-bis(trifluoromethyl)phenyl)-1H-1,2,4-triazol-1-yl)-N-(4-ethylpiperazin-1-yl)acrylamide. $^1$H NMR (400 MHz, CF$_3$COOD) δ: 10.75 (s, 1H), 8.31-8.29 (d, J=10.2H), 7.98 (s, 1H), 7.21-7.23 (d, 1H), 6.08-6.10 (d, 1H), 3.52-3.54 (m, 3H), 3.36 (s, 1H), 3.11 (m, 8H), 1.19-1.22 (m, 3H); LCMS for C$_{19}$H$_{21}$F$_6$N$_6$O [M+H]$^+$ 463.40; found 463.23 (RT 2.43 min, purity: 98.63%).

Example 21: Synthesis of (Z)-3-(3-(3,5-bis(trifluoromethyl)phenyl)-1H-1,2,4-triazol-1-yl)-N-morpholinoacrylamide (I-22)

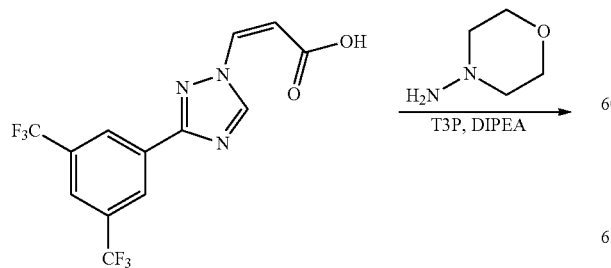

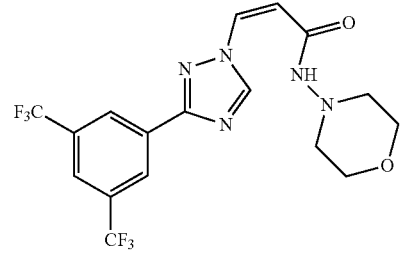

A 50-mL, 3-necked, round-bottomed flask was charged with (Z)-3-(3-(3,5-bis(trifluoromethyl)phenyl)-1H-1,2,4-triazol-1-yl)acrylic acid (0.250 g), morpholin-4-amine (0.072 g, 1.0 eq.) and EtOAc (10 mL). The solution was cooled to −60° C. and treated with T3P (50% in EtOAc; 0.63 mL, 1.5 eq.) and DIPEA (0.24 mL, 2.0 eq.) under a nitrogen atmosphere. The progress of the reaction was followed by TLC analysis using 10% MeOH:CH$_2$Cl$_2$ as mobile phase and visualization under UV light. Upon completion, the reaction mixture was quenched with water and extracted with EtOAc (3×15 mL). The combined organic extracts were dried over anhydrous Na$_2$SO$_4$, filtered and concentrated under reduced pressure (25° C., 20 mmHg) to afford 0.35 g of a crude solid. Purification (Combi-flash, elution with 3% MeOH:CH$_2$Cl$_2$) afforded 100 mg (yield: 33%) (Z)-3-(3-(3,5-bis(trifluoromethyl)phenyl)-1H-1,2,4-triazol-1-yl)-N-morpholinoacrylamide. $^1$H NMR (400 MHz, DMSO-d6) δ=9.52 (s, NH exchange, 1H), 8.51 (s, 2H), 8.28 (s, 1H), 7.38-7.42 (m, 1H), 6.50-6.53 (d, J=10.4 Hz, 1H), 5.84-5.86 (d, J=10.4 Hz, 1H), 3.63 (s, 4H), 2.87 (s, 4H); LCMS for C$_{17}$H$_{16}$F$_6$N$_5$O$_2$ [M+H]$^+$ 436.33; found 436.18 (RT 2.64 min, purity: 100%).

Example 22: Synthesis of (Z)-3-(3-(3,5-bis(trifluoromethyl)phenyl)-1H-1,2,4-triazol-1-yl)-N'-(pyrimidin-4-yl)acrylohydrazide (I-23)

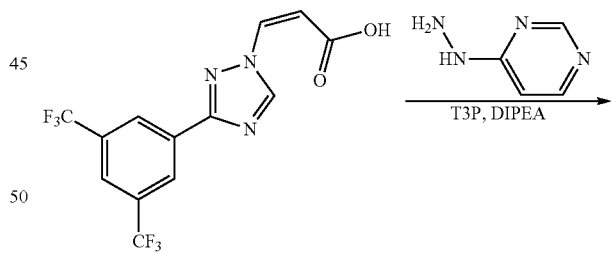

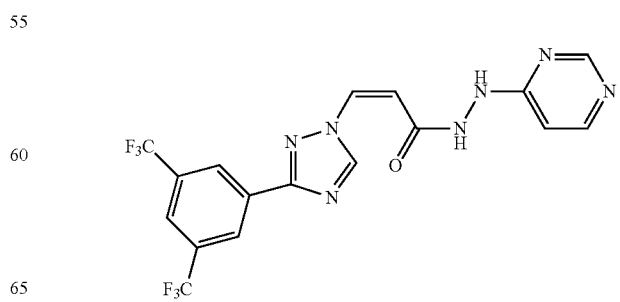

79
Synthesis of 4-hydrazinylpyrimidine

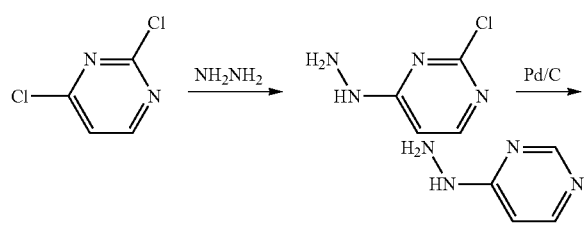

A solution of 2,4-dichloropyrimidine (2.0 g) in EtOH (25 mL) was cooled to 0-20° C. and treated with hydrazine (2.8 mL). The progress of the reaction was followed by TLC using 10% MeOH:CH2Cl2 as mobile phase and visualizing under UV light. The mixture was concentrated under reduced pressure to afford 3.1 g of crude 2-chloro-4-hydrazinyl-pyrimidine (yield=94.8%).

To a solution of 2-chloro-4-hydrazinyl-pyrimidine (200 mg) dissolved in MeOH (10 mL) was added 10% Pd/C (200 mg) and the suspension was stirred under a hydrogen atmosphere until shown to be complete by TLC analysis (using 10% MeOH:CH$_2$Cl$_2$ as mobile phase and visualizing under UV light). The mixture was filtered through Celite® and concentrated under reduced pressure to afford 250 mg of 4-hydrazinylpyrimidine.

80
Synthesis of (Z)-3-(3-(3,5-bis(trifluoromethyl)phenyl)-1H-1,2,4-triazol-1-yl)-N'-(pyrimidin-4-yl)acrylohydrazide A 50-mL, 3-necked, round-bottomed flask was charged with (Z)-3-(3-(3,5-bis(trifluoromethyl)phenyl)-1H-1,2,4-triazol-1-yl)acrylic acid (250 mg, 1.0 eq.) and EtOAc (20.0 mL). 4-Hydrazinylpyrimidine (231 mg, 3 eq.) was added at −60° C. followed by the simultaneous addition of T3P (50% in EtOAc; 0.84 mL, 2.0 eq.) and DIPEA (0.24 mL, 2.0 eq.). The reaction mixture was stirred for 30 min at −60° C. before being concentrated under reduced pressure (35° C., 20 mm Hg) to afford 0.20 g of a solid. Purification by column chromatography (eluting with 5% MeOH in CH$_2$Cl$_2$) afforded 75 mg of material that was purified by preparative TLC (using MeOH:CH$_2$Cl$_2$ as mobile phase) to provide 13 mg (yield=5%) (Z)-3-(3-(3,5-bis(trifluoromethyl)phenyl)-1H-1,2,4-triazol-1-yl)-N'-(pyrimidin-4-yl)acrylohydrazide. $^1$H NMR (400 MHz, DMSO-d6) δ=10.59 (s, 1H), 9.68 (s, NH exchange, 1H), 9.47 (s, NH exchange, 1H), 8.53-8.59 (t, 2H), 8.30 (s, 1H), 8.19-8.20 (d, 1H), 7.53-7.56 (d, J=11.2 Hz, 1H), 6.66-6.67 (d, 1H), 6.06-6.09 (d, J=10.4 Hz, 1H); LCMS for C$_{17}$H$_{12}$F$_6$N$_7$O [M+H]$^+$ 444.31; found 444.19 (RT 2.39 min, purity: 94.97%).

Example 23: Synthesis of (Z)-3-(3-(4-chloro-3,5-bis(trifluoromethyl)phenyl)-1H-1,2,4-triazol-1-yl)-N'-(pyrazin-2-yl)acrylohydrazide (I-24)

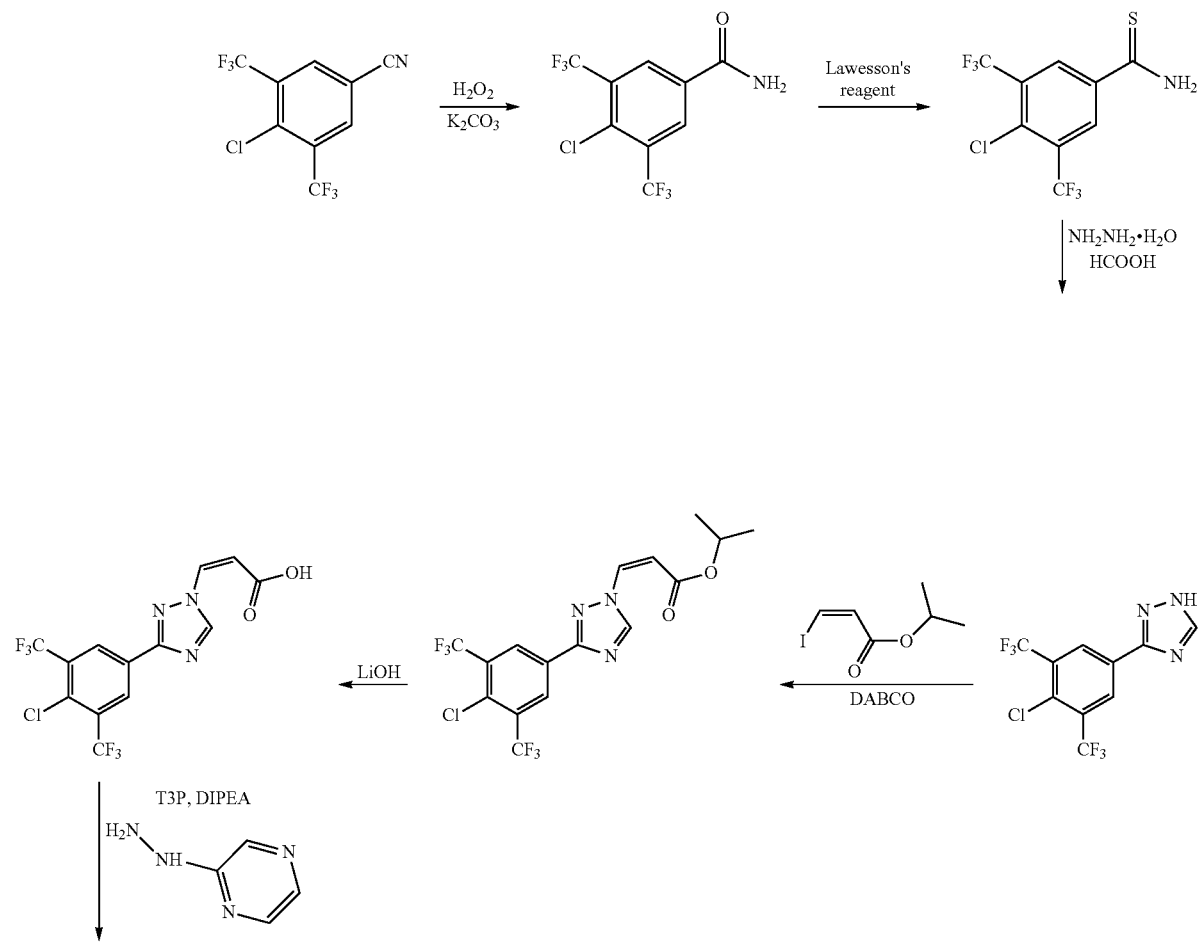

-continued

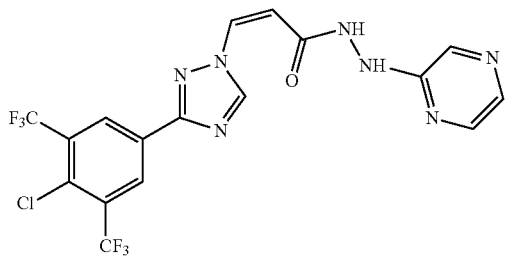

Synthesis of 4-chloro-3,5-bis(trifluoromethyl)benzamide

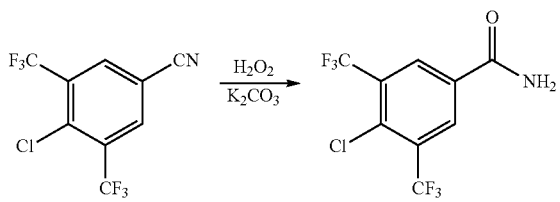

A solution 4-chloro-3,5-bis(trifluoromethyl)benzonitrile (1.0 g) in DMSO (10 mL) was treated with solid K₂CO₃ (0.55 g, 1.1 eq.) and H₂O₂ (30% v/v, 1.0 mL). The reaction mixture was stirred at room temperature for 3 h before being poured into ice-cold water (20 mL). The precipitate was filtered and washed with petroleum ether to afford 1.0 g of crude desired primary amide (yield: 90%).

Synthesis of 4-chloro-3,5-bis(trifluoromethyl)benzothioamide

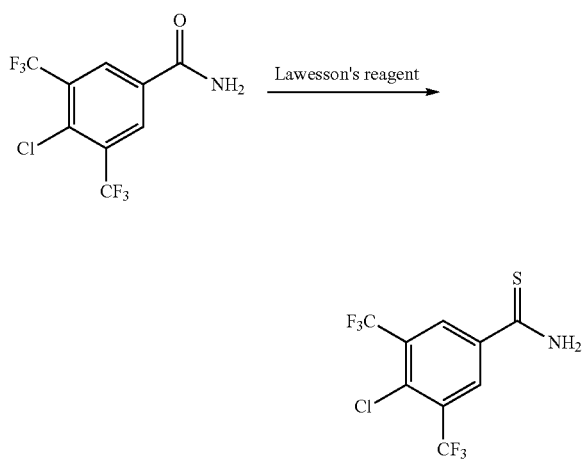

To a solution of 4-chloro-3,5-bis(trifluoromethyl)benzamide (1.2 g) in toluene (20 mL) was added Lawesson's reagent (3.32 g, 2.0 eq.). The reaction mixture was stirred at 90° C. for 8 h before being cooled to room temperature and filtered. The filtrate was poured into water and extracted with EtOAc (3×100 mL). The combined organic extracts were washed with brine (3×50 mL), dried over anhydrous Na₂SO₄, filtered, and concentrated under reduced pressure (25° C., 20 mmHg) to afford 2 g of crude compound. The crude compound was purified by combi-flash chromatography (eluting with 7% EtOAc:hexane) to afford 1.0 g of desired compound (yield: 79%).

Synthesis of 3-(4-chloro-3,5-bis(trifluoromethyl) phenyl)-1H-1,2,4-triazole

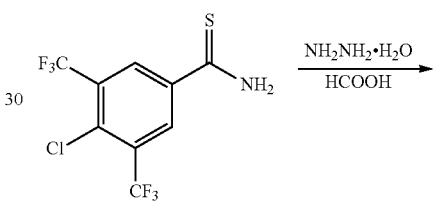

A solution of 4-chloro-3,5-bis(trifluoromethyl)benzothioamide (1 g) in DMF (10 mL) was treated with hydrazine hydrate (0.32 g, 2.0 eq.) and the reaction mixture was stirred at room temperature for 1 h before adding formic acid (3 mL). The reaction mixture was refluxed at 90° C. for 3 h then cooled to room temperature, poured into aqueous saturated NaHCO₃ (slowly, maintaining temperature 25-30° C.) and extracted with EtOAc (3×100 mL). The combined organic extracts were washed with brine (3×50 mL), dried over anhydrous Na₂SO₄, filtered, and concentrated under reduced pressure (25° C., 20 mmHg) to afford 1.5 g of crude compound. Purification by column chromatography (eluting with 40% EtOAc in hexane) afforded 0.50 g of desired compound (yield: 36%).

83

Synthesis of (Z)-isopropyl 3-(3-(4-chloro-3,5-bis(trifluoromethyl)phenyl)-1H-1,2,4-triazol-1-yl)acrylate

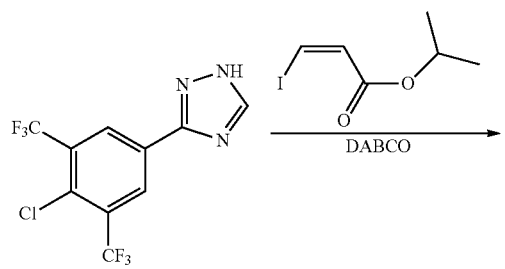

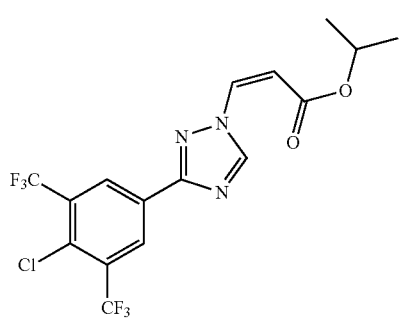

A solution of 3-(4-chloro-3,5-bis(trifluoromethyl)phenyl)-1H-1,2,4-triazole (2.1 g) in DMF (20 mL) was treated with DABCO (1.5 g, 2 eq.) and the mixture was stirred for 30 min before adding (Z)-isopropyl 3-iodoacrylate (1.76 g, 1.1 eq.). The reaction mixture was stirred at room temperature for 5 h then poured into ice-cold water (50 mL) and extracted with EtOAc (3×15 mL). The combined organic extracts were washed with brine (3×10 mL), dried over anhydrous $Na_2SO_4$, filtered, and concentrated under reduced pressure (25° C., 20 mmHg) to afford 3.0 g of crude compound. Purification by column chromatography using (60/120 mesh $SiO_2$, elution with 1-1.2% MeOH in $CH_2Cl_2$) afforded desired unsaturated ester (1.33 g, yield: 52%).

Synthesis of (Z)-3-(3-(4-chloro-3,5-bis(trifluoromethyl)phenyl)-1H-1,2,4-triazol-1-yl)acrylic acid

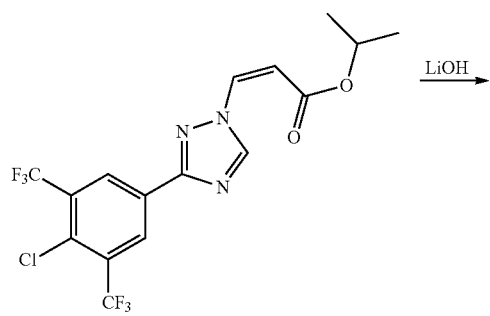

84

-continued

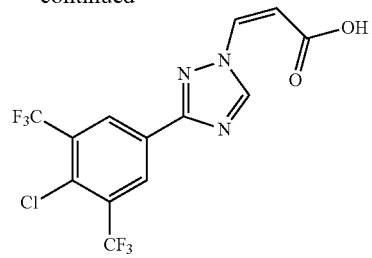

A 25-mL, 3-necked, round-bottomed flask was charged with a solution of (Z)-isopropyl 3-(3-(4-chloro-3,5-bis(trifluoromethyl)phenyl)-1H-1,2,4-triazol-1-yl)acrylate (1.33 g) in 1:1 THF:water (26 mL). The solution was treated with solid LiOH (0.53 g, 4 eq.) and stirred at room temperature for 4 h before being diluted with 400 ml water, acidified to pH=2-3 with dilute aqueous HCl, and extracted with EtOAc (3×100 mL). The combined organic extracts were washed with brine, dried over anhydrous $Na_2SO_4$, filtered and concentrated under reduced pressure to afford 0.8 g of crude compound (yield: 66%).

Synthesis of (Z)-3-(3-(4-chloro-3,5-bis(trifluoromethyl)phenyl)-1H-1,2,4-triazol-1-yl)-N'-(pyrazin-2-yl)acrylohydrazide

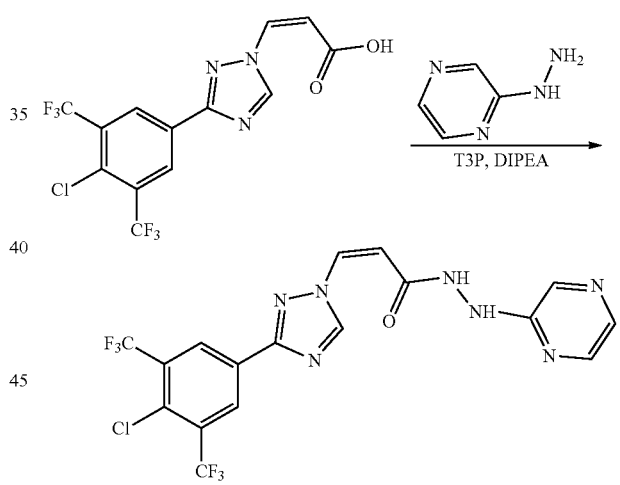

In a 50-mL, 3-necked, round-bottomed flask charged with a solution of (Z)-3-(3-(4-chloro-3,5-bis(trifluoromethyl)phenyl)-1H-1,2,4-triazol-1-yl)acrylic acid (0.8 g) in 1:1 EtOAc:THF (20 mL). The solution was cooled to −70° C. and treated sequentially with 2-hydrazinopyrazine (0.275 g, 1.2 eq.), T3P (50% in EtOAc; 2.5 mL, 2.0 eq.) and DIPEA (1.44 mL, 4.0 eq.), added dropwise. The clear reaction mixture was stirred at −60° C. for 1 h before being concentrated under reduced pressure (25° C., 20 mm Hg) to afford crude compound. Purification by column chromatography using (60/120 mesh $SiO_2$, elution with 34% MeOH in $CH_2Cl_2$) afforded 0.30 g (yield: 30%) (Z)-3-(3-(4-chloro-3,5-bis(trifluoromethyl)phenyl)-1H-1,2,4-triazol-1-yl)-N'-(pyrazin-2-yl)acrylohydrazide. $^1$H NMR (400 MHz, DMSO-d6) δ=10.53 (s, 1H), 9.58 (s, 1H), 9.11 (s, 1H), 8.47 (s, 1H), 8.32 (s, 1H), 8.13 (s, 1H), 8.06 (s, 1H), 7.97 (s, 1H), 7.52-7.55 (d, J=10.4 Hz, 1H), 6.08-6.11 (d, J=10.4 Hz, 1H);

LCMS for $C_{17}H_{11}ClF_6N_7O$ [M+H]$^+$ 478.76 found 478.1 (RT 2.64 min, purity: 100%).

Example 24: Synthesis of (Z)-3-(3-(3,5-bis(trifluoromethyl)phenyl)-1H-1,2,4-triazol-1-yl)-N'-cyclopropylacrylohydrazide (I-25)

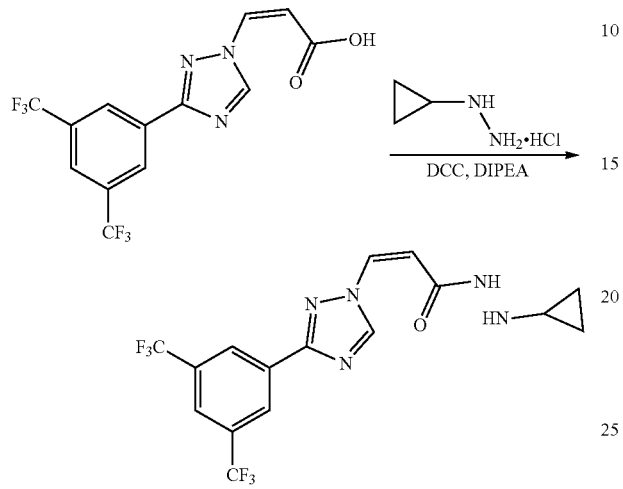

A 100-mL, 3-necked, round-bottomed flask was charged with (Z)-3-(3-(3,5-bis(trifluoromethyl)phenyl)-1H-1,2,4-triazol-1-yl)acrylic acid (0.50 g.) and $CH_2Cl_2$ (25 mL). DCC (0.29 g, 1.0 eq.) was added and the mixture was cooled to 0° C. for the sequential addition of cyclopropylhydrazine hydrochloride (0.15 g, 1.0 eq.) and DIPEA (0.24 mL, 1.0 eq.). The reaction mixture was stirred for 1 h before being poured into water (50 mL) and extracted with $CH_2Cl_2$ (2×50 mL). The combined organic extracts were washed with brine (50 mL), dried over anhydrous $MgSO_4$, filtered, and concentrated under reduced pressure (25° C., 20 mmHg) to afford crude compound. Purification by combi-flash chromatography (elution with 1.5-2.5% MeOH in $CH_2Cl_2$) followed by further purification on a preparative TLC plate (eluting with 70% EtOAc in hexane) afforded 15 mg (yield: 2.6%) (Z)-3-(3-(3,5-bis(trifluoromethyl)phenyl)-1H-1,2,4-triazol-1-yl)-N'-cyclopropylacrylohydrazide. $^1$H NMR (400 MHz, DMSO-d6) δ, 9.16 (s, 1H), 8.52 (s, 1H), 8.28 (s, 1H), 7.23-7.26 (d, J=10.4 Hz, 1H), 6.40-6.43 (d, J=10.4 Hz, 1H), 4.97 (s, 1H), 4.63 (s, 1H), 3.18-3.20 (m, 1H), 0.83-0.87 (m, 2H), 0.65-0.69 (m, 2H); LCMS for Chemical Formula: $C_{16}H_{14}F_6N_5O$ [M+H]$^+$ 406.31 found 406.19 (RT 2.74 min, purity: 98.85%).

Example 25: Synthesis of (Z)-3-(3-(3,5-bis(trifluoromethyl)phenyl)-1H-1,2,4-triazol-1-yl)-N-(3-hydroxyazetidin-1-yl)acrylamide (I-26)

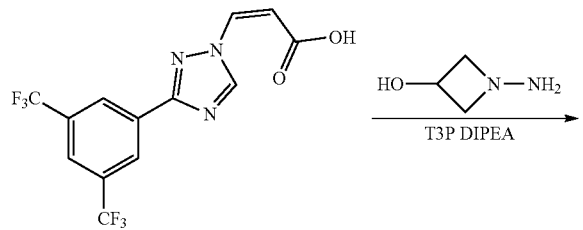

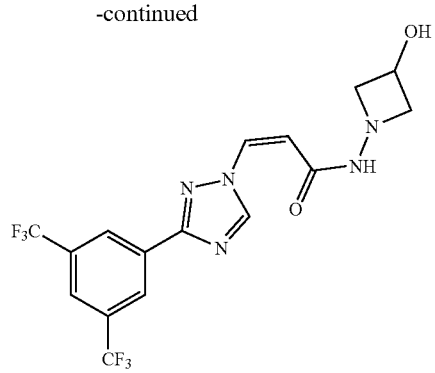

Synthesis of 1-aminoazetidin-3-ol

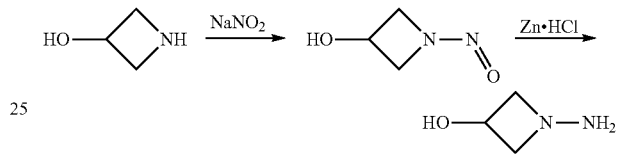

A cooled (15-20° C.) solution of azetidin-3-ol hydrochloride (2.0 g) in water (20 ml) was treated with NaOH (0.8 g in 10 mL water) and the mixture was stirred at 15-20° C. for 1 h. The reaction mixture was then cooled to 0° C. and treated sequentially with a $NaNO_2$ solution (1.89 g in 10 mL water) and acetic acid (1.3 mL). After being stirred for 2 h at 0-5° C., the reaction mixture was poured into water (20 mL), acidified to pH=2-3 with dilute aqueous HCl and extracted with EtOAc (3×25 mL). The combined organic extracts were washed with brine (20 mL), dried over anhydrous $Na_2SO_4$ and concentrated under reduced pressure to afford 0.26 g desired compound, which was used as such in the following step (LCMS purity: 59.84%).

A solution of 1-nitrosoazetidin-3-ol (0.25 g) in MeOH (15 mL) was cooled to −75° C. and treated with dilute aqueous HCl (1.5 mL). Zinc powder (1.35 g) was then added portionwise and the reaction mixture was stirred at ca. −70° C. for 3 h before being filtered through Celite® and concentrated under reduced pressure to afford 90 mg 1-aminoazetidin-3-ol, which was used as such in the following step.

Synthesis of (Z)-3-(3-(3,5-bis(trifluoromethyl)phenyl)-1H-1,2,4-triazol-1-yl)-N-(3-hydroxyazetidin-1-yl)acrylamide A 50-mL, 3-necked, round-bottomed flask was charged with (Z)-3-(3-(3,5-bis(trifluoromethyl)phenyl)-1H-1,2,4-triazol-1-yl)acrylic acid (200 mg) and THF (20.0 mL). The solution was cooled to −60° C. and treated with a solution of 1-aminoazetidin-3-ol (65 mg, 1.3 eq.) in THF. T3P (50% in EtOAc; 0.67 mL, 2.0 eq.) and DIPEA (0.51 mL, 2.0 eq.) were added simultaneously and the reaction mixture was stirred for 30 min at −60° C. before being allowed to warm to room temperature. The reaction mixture was then concentrated under reduced pressure (35° C., 20 mmHg), affording 100 mg of solid. Purification by column chromatography (elution with 3% MeOH in $CH_2Cl_2$) afforded 20 mg (Z)-3-(3-(3,5-bis(trifluoromethyl)phenyl)-1H-1,2,4-triazol-1-yl)-N-(3-hydroxyazetidin-1-yl)acrylamide.

$^1$H NMR (400 MHz, DMSO-d6) δ 9.60 (s, 1H), 6.38 (s, 1H), 8.52 (s, 2H), 8.26 (s, 1H), 7.32-7.35 (d, J=10.8 Hz, 1H), 6.40 (d, exchangeable, 1H), 5.78-5.81 (d, J=10.8 Hz, 1H), 4.14-4.15 (d, 1H), 3.82 (m, 2H), 3.71 (m, 2H); LCMS for Chemical Formula $C_{16}H_4F_6N_5O_2$ [M+H]$^+$ 422.31 found; 422.19 (RT 2.46 min, purity: 91.49%).

Examples 26-31

Examples 26-31 describe novel synthetic methods useful in preparation of compounds of the invention (e.g., as precursors to compounds of the invention, such a compounds described by Formula Z above).

Example 26

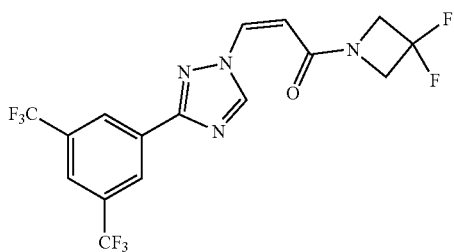 [SMILES: O=C(/C=C\n1cnc(-c2cc(C(F)(F)F)cc(C(F)(F)F)c2)n1)N1CC(F)(F)C1]

Synthesis of Isopropyl Propiolate

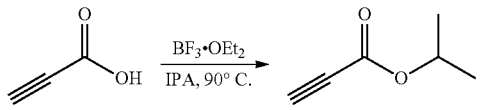

A 20-L, four-necked, round-bottomed flask, equipped with addition funnel, thermometer socket and a mechanical stirrer was charged with propiolic acid (1000 g, 1 equiv.) and IPA (8 L, 8 Vol.). BF$_3$-etherate (4.54 kg, 2.0 equiv.) was added slowly from an addition funnel at 25° C. over a period of 30 minutes. The temperature of the reaction mixture was gradually increased up to 90° C. and the reaction mass was maintained at that temperature for 3 hrs. GC monitoring after 3 hrs showed the completion of the reaction. The reaction mixture was cooled to room temperature, quenched with 20 L of ice cold DM water and stirred for 30 minutes. 10 L of dichloromethane was added to the reaction mixture and the reaction mass was stirred for another 30 minutes. The organic layer was separated and the aqueous layer was reextracted with 5 L of dichloromethane. The combined organic layers was washed with 10 L of saturated brine, dried over anhydrous sodium sulphate, and concentrated under vacuum at 35° C. to 40° C. (product is volatile) to yield the product as a brown liquid (1.32 kg, 81.25%). Purity 89.67% (GC); $^1$H NMR (300 MHz, CDCl$_3$) δ: 1.22 (d, 6H, J=6.6 Hz), 2.85 (s, 1H), 4.98-5.05 (m, 1H).

Synthesis of (Z)-isopropyl 3-iodoacrylate

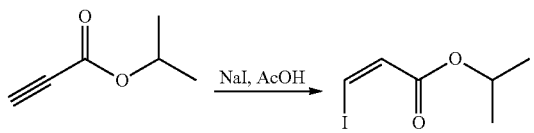

A 20-L, four-necked, round-bottomed flask equipped with addition funnel thermometer socket and mechanical stirrer was charged with isopropyl propiolic ester (1000 g, 1 equiv.) and acetic acid (3.7 L, 3.7 Vol.) at 25° C. and the reaction mass was stirred for 10 minutes. Sodium iodide (2.138 Kg, 1.6 Vol.) was added and the reaction mixture was stirred (a dark brown colour was observed). The temperature was increased to 110° C. and the reaction was maintained at that temperature for 1.5 hrs. GC monitoring showed the completion of the reaction after 1.5 hrs. The reaction mixture was cooled to room temperature, quenched with ice cold DM water (18.75 L, 18.75 V) and stirred for 30 mins. MTBE (5 L) was added to the reaction mass and stirred for another 30 minutes. The organic layer was separated and the aqueous layer was reextracted with MTBE (5 L). The combined organic layer was washed with NaHCO$_3$ (2×10 L), NaHSO$_3$ (2×5 L), saturated brine solution (5.2 L, 5.2 V), dried over sodium sulphate and concentrated under vacuum at 35° C. to yield (Z)-isopropyl 3-iodoacrylate as a brown liquid (1.49 kg, 70%). Purity 87.34% (GC); $^1$H NMR (300 MHz, CDCl$_3$) δ:1.28 (d, 6H, J=6.3 Hz), 5.08-5.131 (m, 1H), 6.83 (d, 1H, J=8.7 Hz), 7.38 (d, 1H, J=8.7 Hz).

Synthesis of 3,5-bis(trifluoromethyl)benzothioamide

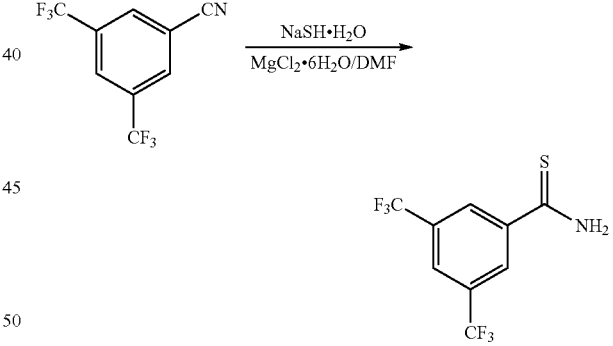

A 20-L, multi-necked flask equipped with an over-head stirrer, and thermometer socket was charged with bis(trifluoromethyl)benzonitrile (1.25 kg, 1.0 equiv.) and DMF (6.25 L, 5V), and the resulting mixture was stirred under nitrogen at room temperature (28° C.). The reaction mixture was cooled to 10° C. and 0.775 g NaSH.H$_2$O (2 equiv.) was added over a period of 10 mins. After stirring for 15 minutes, MgCl$_2$.6H$_2$O (1.169 kg, 1.1 equiv.) was added portionwise over a period of 15 minutes and the reaction was stirred for another 35 minutes. The progress of the reaction (green-colored solution) was monitored by HPLC which showed 99.6% product and 0.03% benzonitrile. The reaction mixture was cooled to 0-5° C. and 30% dil. HCl (3.75 L) was added dropwise to adjust the pH to 2-3. The resulting mass was extracted with MTBE (5 L×1). The layers were separated and 1 L of DM water was added to the aqueous layer, which was re-extracted with MTBE (2.5 L×1). The combined organic layers were washed with brine (4.5 L×3), dried and concentrated under vacuum. Hexane was added to the solid obtained, chased and the product was isolated as yellow solid (1.400 Kg, 98.0%). Purity: 99.28% (HPLC). $^1$H NMR (300 MHz, CDCl3) δ: 8.27 (s, 1H), 8.53 (s, 2H), 10.0 (s, 1H), 10.38 (s, 1H).

Synthesis of 3-(3,5-bis(trifluoromethyl)phenyl)-1H-1,2,4-triazole

Synthesis of (Z)-isopropyl 3-(3-(3,5-bis(trifluoromethyl)phenyl)-1H-1,2,4-triazol-1-yl)acrylate

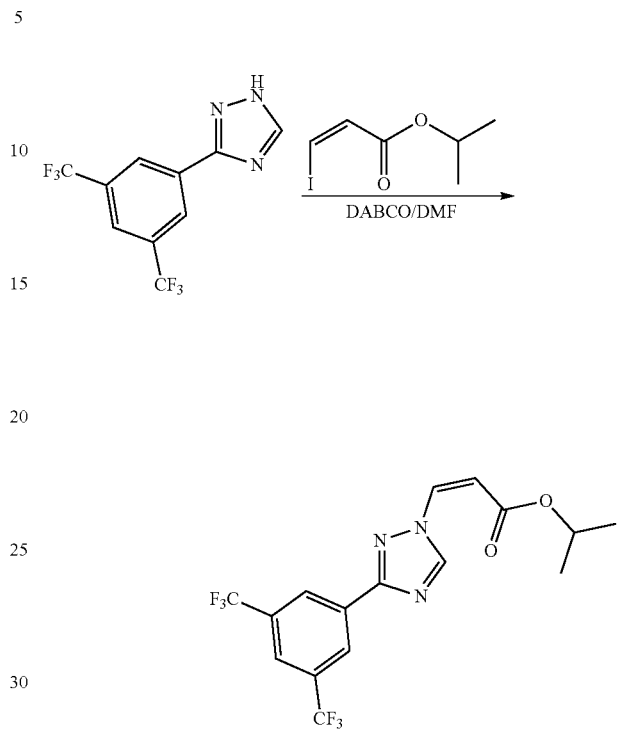

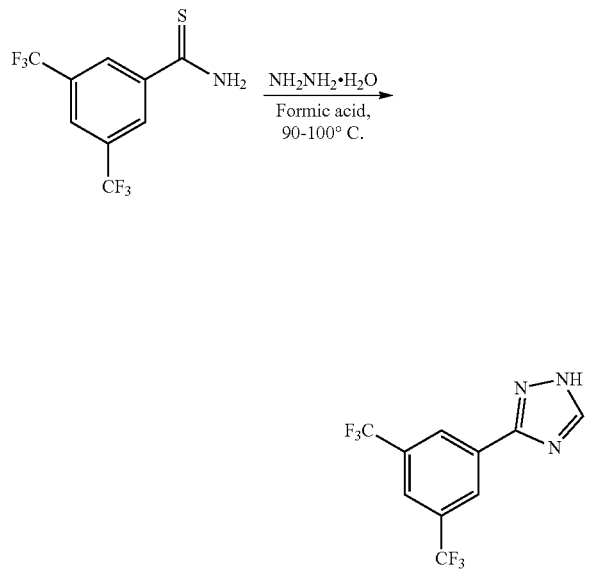

A 20-L, multi-necked flask equipped with an over-head stirrer and thermometer socket was charged with thioamide (1378 g, 1 equiv.) and DMF (6.89 L, 5V), and the mixture was stirred under nitrogen at room temperature (28° C.). The reaction mass was cooled to 10° C. and hydrazine hydrate (505.4 g, 2.0 equiv.) was added dropwise over 2 hours with stirring. The reaction mass was cooled to 0° C. to 5° C. and formic acid was added over a period of 1 hour (6.89 L, 5V) (exotherm was observed and the temperature increased to 20° C.). The reaction mixture was then heated at 95 to 100° C. for another 12 hrs. The progress of the reaction was monitored by HPLC which showed the formation of 99.5% product. The reaction mass was cooled to 35 to 40° C., added to 20.6 L of pre-cooled DM water (10 to 15° C.) and stirred for 30 minutes. The reaction mass was extracted with MTBE (8.26 L). The aqueous layer was again extracted with MTBE (5.512 L) and the combined organic layers were washed with 10% sodium bicarbonate (6.89 L, 2V), brine (6.89 L×3), dried with sodium sulfate and concentrated under vacuum. Dichloromethane (2V) was added to the yellow solid obtained and stirred at 0 to 5° C. for 1 hour, which, on filtration, gave the product as a yellow solid (1156 g, 82.2%). Purity: 99.7% (HPLC); $^1$H NMR (300 MHz, DMSO) δ: 8.15 (s, 1H), 8.55 (s, 2H), 8.79 (s, 1H), 14.5 (s, 1H, NH).

A 10-L, four-necked, round-bottomed flask, equipped with addition funnel, thermometer socket, mechanical stirrer, and stopper was charged with 3-(3,5-bis(trifluoromethyl)phenyl)-1H-1,2,4-triazole (600 g, 1.0 eq.), DABCO (480 g, 2.0 eq) and DMF (3.0 L). The reaction mixture was stirred for 30 minutes. After 30 minutes, a solution of iodo ester (1024.8 g, 2.0 eq) in DMF (1200 mL) was added dropwise over a period of 1 hour. The progress of the reaction was monitored by HPLC and showed (Z)-isopropyl 3-(3-(3,5-bis(trifluoromethyl)phenyl)-1H-1,2,4-triazol-1-yl) acrylate: 62.36% and 3-(3,5-bis(trifluoromethyl)phenyl)-1H-1,2,4-triazole: 15.1%. After 1 hour further, one equivalent of DABCO (258 g) was added and the reaction was maintained for another hour. HPLC analysis showed the conversion as 75.63% (Z)-isopropyl 3-(3-(3,5-bis(trifluoromethyl)phenyl)-1H-1,2,4-triazol-1-yl)acrylate and 2% 3-(3,5-bis(trifluoromethyl)phenyl)-1H-1,2,4-triazole. The reaction mixture was quenched with cold DM water (12 L), stirred for 15 minutes, and extracted with ethyl acetate (2×6 L). The combined organic layers were washed with saturated brine solution (30%, 2×3 L), dried over anhydrous sodium sulfate (100 g) and concentrated. The crude mass (840 g) was taken in a 10 L round bottomed flask and methanol (1200 mL) was added. The solution was maintained at 0-5° C. and stirred for 30 minutes. The obtained solid was filtered and washed with methanol (200 mL), which yielded the product as a white solid (550 g, 65.0%). Purity: 87.34% (HPLC); $^1$H NMR (300 MHz, CDCl$_3$) δ: 1.30 (d, 6H, J=6.0 Hz), 5.12 (m, 1H), 5.73 (d, 1H, J=10.8 Hz), 7.24 (d, 1H, J=10.8 Hz), 7.91 (s, 1H), 8.58 (s, 2H), 9.70 (s, 1H). Cis-isomer: Trans-isomer ratio is 83:8.

Synthesis of (Z)-3-(3-(3,5-bis(trifluoromethyl)phenyl)-1H-1,2,4-triazol-1-yl)acrylic acid

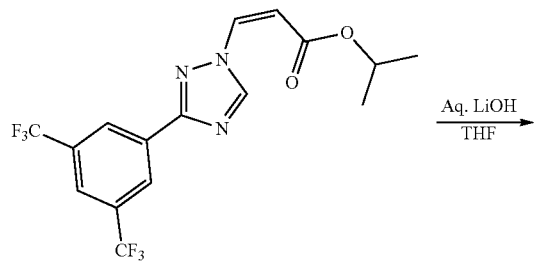

Synthesis of (Z)-3-(3-(3,5-bis(trifluoromethyl)phenyl)-1H-1,2,4-triazol-1-yl)-1-(3,3-difluoroazetidin-1-yl)prop-2-en-1-one

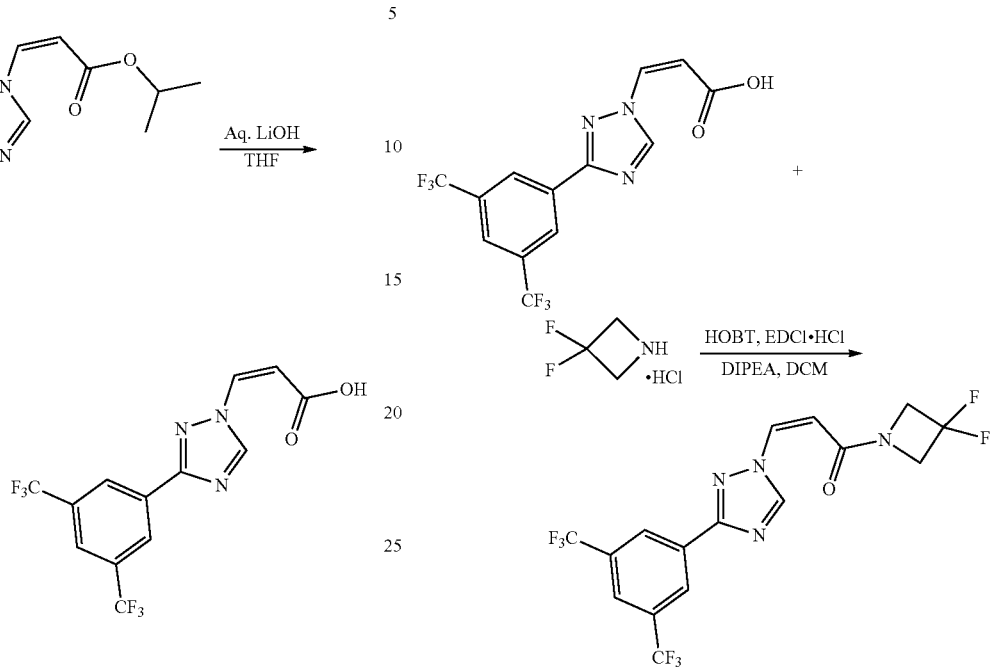

A 5-L, four-necked, round-bottomed flask equipped with addition funnel, thermometer socket, mechanical stirrer and stopper was charged with THF (1.25 L) and (Z)-isopropyl 3-(3-(3,5-bis(trifluoromethyl)phenyl)-1H-1,2,4-triazol-1-yl)acrylate (125 g, 1 eq.) at room temperature. The reaction mixture was cooled to 0° C. To the stirring solution was added ice cold lithium hydroxide solution (66.58 g in 1.25 L water) over a period of 30 minutes through an addition funnel. The reaction temperature was slowly raised to 25° C. and the reaction mass was maintained at that temperature for 2 hours. HPLC monitoring showed the following status: (Z)-3-(3-(3,5-bis(trifluoromethyl)phenyl)-1H-1,2,4-triazol-1-yl)acrylic acid: 87.66%; (E)-3-(3-(3,5-bis(trifluoromethyl)phenyl)-1H-1,2,4-triazol-1-yl)acrylic acid: 9.91%, (Z)-isopropyl 3-(3-(3,5-bis(trifluoromethyl)phenyl)-1H-1,2,4-triazol-1-yl)acrylate 2%. The reaction was continued for another 30 minutes and submitted for HPLC monitoring ((Z)-3-(3-(3,5-bis(trifluoromethyl)phenyl)-1H-1,2,4-triazol-1-yl)acrylic acid: 88.20%; (E)-3-(3-(3,5-bis(trifluoromethyl)phenyl)-1H-1,2,4-triazol-1-yl)acrylic acid: 11.03%. After completion of the reaction, the reaction mixture was quenched with ice cold water (385 mL) and stirred for 30 minutes. The pH was adjusted to 1-2 with dilute hydrochloric acid (30%, 400 mL) and the reaction mass was extracted with ethyl acetate (3×625 mL). The combined organic layers were washed with saturated brine solution (30%, 650 mL), dried over anhydrous sodium sulfate (12.5 g) and concentrated under reduced pressure at 30-35° C. Hexane was added to the crude material and stirred for 30 minutes. The obtained solids were filtered through a Buchner funnel and washed with hexane (250 mL). The solid obtained was dried for 30 minutes under vacuum and at room temperature for 3-4 hours. The product was isolated as a white powder (92.8 g, 84.36%). Purity: 93% (HPLC); $^1$H NMR (300 MHz, DMSO-d6) δ: 5.98 (d, 1H, J=10.2 Hz), 7.48 (d, 1H, J=10.2 Hz), 8.2 (s, 1H), 8.50-8.54 (m, 2H), 9.39 (s, 1H).

To a 3-L, four-necked, round-bottomed flask equipped with nitrogen inlet, addition funnel, thermometer socket, mechanical stirrer was added (Z)-3-(3-(3,5-bis(trifluoromethyl)phenyl)-1H-1,2,4-triazol-1-yl)acrylic acid (100 g, 1.0 eq.) in DCM (1.8 L, 18 V). The reaction mixture was cooled to −0° C. To the cooled solution, were added HOBT (4.4 g, 0.1 eq.), EDC-HCl (80.6 g, 1.5 eq.) and 3,3-difluoroazetidine hydrochloride (44 g, 1.2 eq.). To the resulting mixture at −10° C., was added DIPEA (72 mL, 1.5 eq) dropwise over a period of 1.5 hours. The progress of the reaction was monitored by HPLC analysis which showed the completion of the reaction at the end of DIPEA addition. The reaction temperature was slowly raised to 15° C. to 20° C. (~2 h). The reaction mixture was quenched with 1 L ice-water slurry. The organic layer was separated and the aqueous layer was extracted with DCM (400 mL×2). The organic layer was washed with saturated brine solution (2×500 ml), dried over anhydrous Na$_2$SO$_4$ (10 g) and concentrated under reduced pressure (~35° C.) to afford crude compound. The crude compound thus obtained was dissolved in 5 vol. of DIPE and stirred at rt for 30 min. and then filtered. Crude weight was 100 g (yield=82.39%) [Cis-85.07% by HPLC, Trans-14.36% by HPLC].

The crude compound thus obtained was further purified by recrystallisation with ethyl acetate according to the following procedure. To a 500-mL, four-necked, round-bottomed flask equipped with mechanical stirrer, thermometer socket and stopper was added 100 g of (Z)-3-(3-(3,5-bis(trifluoromethyl)phenyl)-1H-1,2,4-triazol-1-yl)-1-(3,3-difluoroazetidin-1-yl)prop-2-en-1-one. To this compound at rt was added ethyl acetate (7 volumes) under stirring. However, compound was not completely soluble. Hence, the resulting solution was heated to 60° C. to obtain a clear solution and was then slowly cooled to −30° C. At −30° C., solution was stirred for 20 min. and filtered under suction. The compound obtained was dried under vacuum at 40-45°

C. for 3 h-4 hrs to yield the product as a white solid. (Cis-98.9% by HPLC); (Z)-3-(3-(3,5-bis(trifluoromethyl)phenyl)-1H-1,2,4-triazol-1-yl)-1-(3,3-difluoroazetidin-1-yl)prop-2-en-1-one. $^1$H NMR (300 MHz, CDCl$_3$) δ 9.57 (s, 1H), 8.56 (s, 2H), 7.90 (s, 1H), 7.18-7.21 (d, J=10.8 Hz, 1H), 5.61-5.65 (d, J=10.8 Hz, 1H), 4.39-4.45 (m, 4H).

Example 27

Synthesis of (Z)-3-iodoacrylic acid

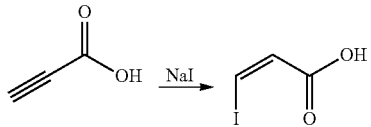

A 250-mL, three-necked, round-bottomed flask equipped with nitrogen inlet was added propiolic acid (7.0 g, 1.0 eq) dissolved in acetic acid (70 mL, 10V) and sodium iodide (29.96 g, 2.0 eq). The reaction mixture was refluxed at 1000 C for 2-3 h. The progress of the reaction was followed by TLC analysis on silica gel with 10% MeOH:DCM as mobile phase. SM Rf=0.3 and Product Rf=0.5. Reaction mixture was poured into ice water (700 mL) and neutralized with saturated sodium bicarbonate solution. The reaction mixture was extracted with EtOAc (3×100 mL). The combined organic layers were washed with brine solution (3×100 mL), dried over MgSO4, filtered, and concentrated by rotary evaporation (25° C., 20 mmHg) to afford 12.0 g of crude compound which was purified by column chromatography using silica 60/120 using MeOH:DCM as mobile phase. The column (5×10 cm) was packed in DCM and started eluting in MeOH in gradient manner starting with fraction collection (50-mL fractions) from 2% to 5% MeOH in DCM. Compound started eluting with 2% MeOH in DCM. Fractions containing such TLC profile were combined to obtain 8.0 gm of desired compound (yield 40.44%).

Synthesis of (Z)-1-(3,3-difluoroazetidin-1-yl)-3-iodoprop-2-en-1-one

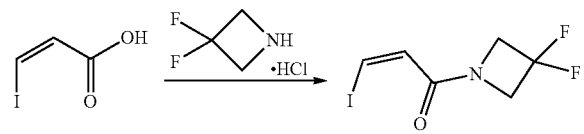

In a 25-mL, three-necked, round-bottomed flask equipped with nitrogen inlet and a rubber septum, (Z)-3-iodoacrylic acid (0.250 g, 1.0 eq.) was dissolved in DCM (10 mL, 40 V). The reaction mixture was cooled to 0° C., and DIPEA (0.168 g, 1.1 eq), HATU (0.494 g, 1.1 eq) and 3,3-difluoroazetidine hydrochloride (0.179 g, 1.1) were added. The reaction mixture was stirred at 0° C. for 2-3 hr. The progress of the reaction was followed by TLC analysis on silica gel with 40% ethyl acetate in hexane. The reaction mixture was filtered and concentrated by rotary evaporation (25° C., 20 mmHg) to afford 0.3 g of crude compound which was purified by column chromatography using silica 60/120 using 40% ethyl acetate in hexane as mobile phase. The column (5×10 cm) was packed in 5% ethyl acetate in hexane and started eluting in ethyl acetate in gradient manner starting with fraction collection (50-mL fractions) from 20% to 30% ethyl acetate in hexane. Compound started eluting with 20% ethyl acetate in hexane. Fractions containing such TLC profile were combined to obtain 0.18 g of desired compound (yield 52.33%). Mass: [M+H]$^+$:273.8.

Synthesis of (Z)-3-(3-(3,5-bis(trifluoromethyl)phenyl)-1H-1,2,4-triazol-1-yl)-1-(3,3-difluoroazetidin-1-yl)prop-2-en-1-one

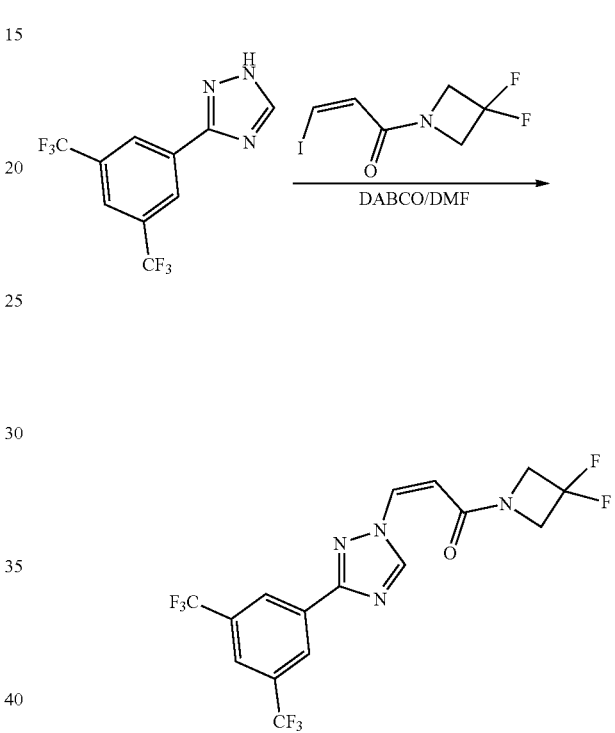

In a 25-mL, three-necked, round-bottomed flask equipped with nitrogen inlet, 3-(3,5-bis(trifluoromethyl)phenyl)-1H-1,2,4-triazole (0.18 g, 1.0 eq.) was dissolved in DMF (5.0 mL, 27.0 V), and DABCO (0.143 g, 2.0 eq) and (Z)-1-(3,3-difluoroazetidin-1-yl)-3-iodoprop-2-en-1-one (0.192 g, 1.1 eq) were added. The reaction mixture was stirred at RT for 2-3 hr. The progress of the reaction was followed by TLC analysis on silica gel with 80% ethyl acetate-hexane as mobile phase, SM Rf=0.60 and Product Rf=0.4. Reaction mixture was poured in to ice water (50 mL) and extracted with EtOAc (3×25 mL). The combined organic layers were washed with brine solution (3×25 mL), dried over MgSO$_4$, filtered, and concentrated by rotary evaporation (25° C., 20 mmHg) to afford 0.3 g of crude compound which was purified by column chromatography using silica 60/120 using ethyl acetate:hexane as mobile phase. The column (5×10 cm) was packed in hexane and started eluting in ethyl acetate in gradient manner starting with fraction collection (50-mL fractions) from 40% to 45% ethyl acetate in hexane. Compound started eluting with 40% ethyl acetate in hexane. Fractions containing such TLC profile were combined to obtain 70 mg of desired compound (yield 25.64%).

Example 28. Synthesis of (Z)-isopropyl 3-(3-(3-isopropoxy-5-(trifluoromethyl)phenyl)-1H-1,2,4-triazol-1-yl)acrylate

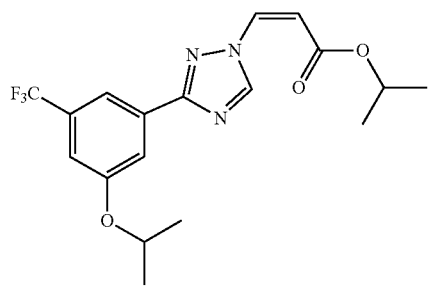 [SMILES: CC(C)OC(=O)/C=C\n1cnc(-c2cc(OC(C)C)cc(C(F)(F)F)c2)n1]

Synthesis of isopropyl propiolate. To a mixture of propiolic acid (500 g, 7.1 moles) in isopropanol (4000 mL) was added BF3 etherate (2015 g, 14.2 moles) at 10° C. After stirring for 10 minutes, the reaction mixture was heated to 90° C. and stirred for 2 hours. The completion of the reaction was monitored by TLC. The reaction mixture was brought down to 25 to 30° C. and quenched with crushed ice followed by extraction with dichloromethane. The organic layer was washed with water and then with brine solution. Organic layer was dried over sodium sulfate and concentrated under vacuum to give the isopropyl propiolate (440 g; 55%). Product was confirmed by $^1$H NMR.

Synthesis of (Z)-isopropyl 3-iodoacrylate

To a mixture of isopropyl propiolate (350 g, 3.1 moles) in AcOH (1300 mL) was added NaI (930 g, 6.2 moles) at 25° C. The reaction mixture was heated to 115° C. and stirred for 1.5 hrs. The reaction mixture was cooled to 25 to 30° C. and quenched with water followed by extraction with MTBE. The organic layer was washed with saturated bicarbonate, bisulfite and brine solution. The organic layer was dried over sodium sulfate and concentrated under vacuum to give the product (Z)-isopropyl 3-iodoacrylate (626 g; 83.5%). Product was confirmed by $^1$H NMR.

Synthesis of 3-isopropoxy-5-(trifluoromethyl)benzonitrile

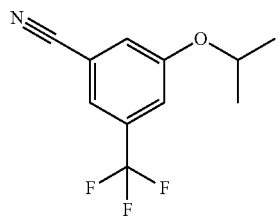 [SMILES: CC(C)Oc1cc(C#N)cc(C(F)(F)F)c1]

To a mixture of propan-2-ol (102.96 g 1.76 moles) in DMF (3200 mL, 8 V) at 5° C. was added NaH (122 g, 5.08 moles). The mixture was stirred for 2 hours. To this mixture 3-fluoro-5-(trifluoromethyl)benzonitrile (400, 2.1 moles) was added dropwise. The temperature of the mass was increased to 25 to 30° C. and maintained at same temperature for 1 hour.

Reaction was monitored by HPLC. After completion, the reaction mixture was quenched with ice cold water and extracted with ethyl acetate. The ethyl acetate layer was washed with brine, dried over sodium sulfate and then concentrated under vacuum to give 530 g (2.31 moles; 110%) of 3-isopropoxy-5-(trifluoromethyl)benzonitrile, which was taken as such to next step with no further purification. HPLC purity—96.5% by area (a/a).

Synthesis of 3-isopropoxy-5-(trifluoromethyl)benzothioamide

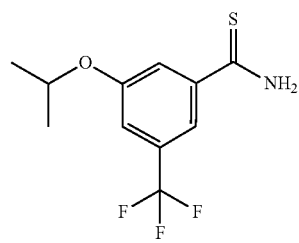 [SMILES: CC(C)Oc1cc(C(N)=S)cc(C(F)(F)F)c1]

3-Isopropoxy-5-(trifluoromethyl)benzonitrile (1000 g, 4.3 moles) was dissolved in DMF (4000 mL) and sodium hydrogensulfide hydrate (636 g; 8.6 moles) was added followed by magnesium chloride hexahydrate (960.2 g, 4.7 moles). The reaction mixture was stirred for 1 hr at 25 to 30° C. Reaction completion was monitored by TLC using ethyl acetate:hexane (2:8) as the mobile phase. The reaction mixture was quenched in an ice-water slurry (250 mL) and the pH was adjusted to 5 by addition of 10% aqueous HCl. The reaction mixture was extracted with MTBE and was washed with 20% brine solution. The organic layer was concentrated under vacuum to give 1136 g (4.3 moles; 100%) of the title compound, which was taken as such to next step. HPLC purity—97.37% a/a.

Synthesis of 3-(3-isopropoxy-5-(trifluoromethyl)phenyl)-1H-1,2,4-triazole

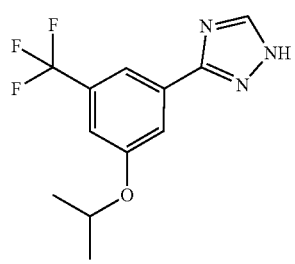 [SMILES: CC(C)Oc1cc(-c2nc[nH]n2)cc(C(F)(F)F)c1]

3-Isopropoxy-5-(trifluoromethyl)benzothioamide (646 g; 2.74 moles) was combined with hydrazine hydrate (140 g; 4.4 moles) and DMF (3200 mL; 5V). The mixture was stirred for 30 minutes and cooled to 10° C. To this reaction mixture was added formic acid (3200 mL) dropwise. Reaction mixture was heated to 90 to 100° C. and maintained for 12 hrs. After reaction completion by HPLC, reaction mass was cooled to 25 to 30° C. and quenched with ice-cold water. The mixture was extracted in MTBE. The organic layer was washed with brine followed by aqueous sodium bicarbonate, and concentrated under vacuum. The residue was chased off using hexane, the resulting residue was slurried at 10° C. for 1 hour. The solid obtained was filtered and dried for 12 hours at 25 to 30° C. to yield 550 g (2.26 moles: 82%) of the product 3-(3-methoxy-5-(trifluoromethyl)phenyl)-1H-1,2,4-triazole. HPLC purity-95.24% a/a.

Synthesis of (Z)-isopropyl 3-(3-(3-isopropoxy-5-(trifluoromethyl)phenyl)-1H-1,2,4-triazol-1-yl)acrylate

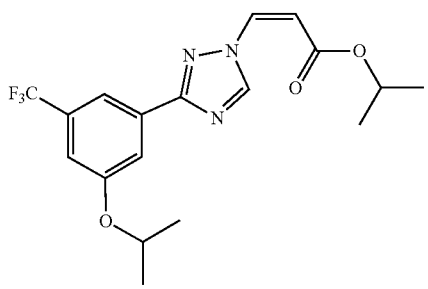 [SMILES: CC(C)OC(=O)/C=C\n1cnc(-c2cc(OC(C)C)cc(C(F)(F)F)c2)n1]

A mixture of 3-(3-methoxy-5-(trifluoromethyl)phenyl)-1H-1,2,4-triazole (500 g, 1.8 moles) and DABCO (417.6 g; 3.6 moles) in DMF (1200 mL) was stirred for 30 minutes. To this mixture was added (Z)-isopropyl 3-iodoacrylate (864 g; 3.6 moles) in DMF (1200 mL) slowly at 25 to 30° C. and the reaction mixture was stirred for 1 hour. After 1 hour, DABCO (208 g; 1 eq) was added and the reaction mixture was stirred for 1 hour. HPLC analysis showed 3-(3-methoxy-5-(trifluoromethyl)phenyl)-1H-1,2,4-triazole 9.59%, (Z)-isopropyl 3-(3-(3-isopropoxy-5-(trifluoromethyl)phenyl)-1H-1,2,4-triazol-1-yl)acrylate: 73.76%, (E)-isopropyl 3-(3-(3-isopropoxy-5-(trifluoromethyl)phenyl)-1H-1,2,4-triazol-1-yl)acrylate: 6.66%. The reaction mass was quenched with water, extracted with dichloromethane and concentrated under vacuum to give the crude product. The crude product was chromatographed using ethyl acetate-hexane system in 60-120 silica gel to give 310 g (0.8 moles; 44%). HPLC purity—99% a/a.

Example 29. Synthesis of (Z)-isopropyl 3-(3-(3-methoxy-5-(trifluoromethyl)phenyl)-1H-1,2,4-triazol-1-yl)acrylate

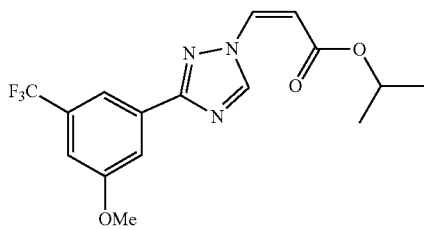 [SMILES: COc1cc(-c2ncn(/C=C\C(=O)OC(C)C)n2)cc(C(F)(F)F)c1]

To a solution of 3-(3-methoxy-5-(trifluoromethyl)phenyl)-1H-1,2,4-triazole (0.50 g) (prepared according to Example 3) in DMF (1.5 mL) was added DABCO (2 equiv). The resulting reaction mixture was stirred for 30 min at room temperature then (Z)-isopropyl 3-iodoacrylate (2.0 equiv; prepared according to Example 3) was added. The resulting mixture was stirred at rt for 3 hrs. The reaction mixture was quenched with ice-cold water, and extracted with ethyl acetate (3 times). Organic layers were separated and the combined organic layer was dried over anhydrous sodium sulfate. LC-MS and HPLC analysis revealed 62% cis-isomer and 36% trans-isomer. $^1$H NMR (400 MHz, CDCl$_3$) δ: 9.72 (s, 1H), 8.02 (s, 1H), 7.86 (s, 1H), 7.30 (s, 1H), 7.28 (d, J=8.8 Hz, 1H), 5.71-5.73 (d, J=10.8 Hz, 1H), 5.12-5.18 (m, 1H), 3.94 (s, 3H), 1.34 (d, 6H): LCMS for C$_{16}$H$_{16}$F$_3$N$_3$O$_3$ [M+1]$^+$ 355.31 found 355.92 at 4.317 min (LCMS 99.82%).

Example 30. Synthesis of (Z)-isopropyl 3-(3-(2-chloro-6-isopropoxypyridin-4-yl)-1H-1,2,4-triazol-1-yl)acrylate

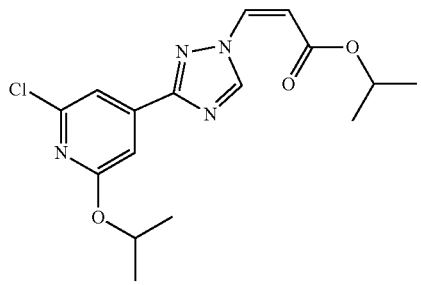 [SMILES: CC(C)OC(=O)/C=C\n1cnc(-c2cc(Cl)nc(OC(C)C)c2)n1]

To 2-chloro-6-isopropoxy-4-(1H-1,2,4-triazol-3-yl)pyridine (0.5 g) (prepared as in Example 3) in 3 mL of DMF, was added DABCO (0.467 g, 2 equiv) and the resulting mixture was stirred for 30 min. A solution of (Z)-isopropyl 3-iodoacrylate (0.990 g, 2 equiv) (prepared as in Example 3) was added to the reaction mixture, and the resulting mixture was stirred for 3 h at room temperature. Reaction mixture was worked up as in Example 3, to obtain 53% cis-isomer and 34% trans isomer 34%.

Example 31. Synthesis of (Z)-isopropyl 3-(3-(3-(cyclobutylamino)-5-(trifluoromethyl)phenyl)-1H-1,2,4-triazol-1-yl)acrylate

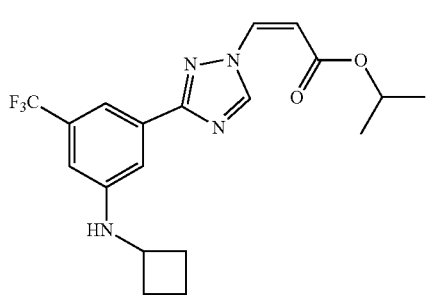 [SMILES: CC(C)OC(=O)/C=C\n1cnc(-c2cc(NC3CCC3)cc(C(F)(F)F)c2)n1]

To N-cyclobutyl-3-(1H-1,2,4-triazol-3-yl)-5-(trifluoromethyl)aniline (0.5 g) (prepared as in Example 3) in 1.5 mL of DMF, was added DABCO (0.188 g) and the resulting mixture was stirred for 30 min. A solution of (Z)-isopropyl 3-iodoacrylate (0.404 g) (prepared as in Example 3) was added to the reaction mixture, and the resulting mixture was stirred for 3 h at room temperature. Reaction mixture was worked up as in Example 3, to obtain 44% cis-isomer and 20% trans-isomer.

Example 32

Assays. Exemplary compounds of the invention were tested in parallel with Compounds X-1, X2 and X-3 (depicted in Table 2), in various assays. The results are set forth in Table 2 below.

Inhibition of Nuclear Export

The ability of exemplary compounds of the invention to inhibit CRM1-mediated nuclear export was assessed in a RevGFP assay. Rev is a protein from human immunodeficiency virus type 1 (HIV-1) and contains a nuclear export signal (NES) in its C-terminal domain and a nuclear localization signal (NLS) in its N-terminal domain. Nuclear export of Rev protein is dependent on the classical NES/CRM1 pathway (Neville et al. 1997). Nuclear accumulation of Rev can be observed in cells treated with specific inhibitors of CRM1, such as LMB (Kau et al. 2003).

In this assay, U2OS-RevGFP cells were seeded onto clear-bottomed, black, 384-well plates the day before the experiment. Compounds were serially diluted 1:2 in DMEM, starting from 40 µM in a separate, 384-well plate, and then transferred onto the cells. The cells were incubated with compound for about 1 hr before fixation with 3.7% formaldehyde and nuclei staining with Hoechst 33258. The amount of GFP in cell nuclei was measured and the $IC_{50}$ of each compound was determined (Kau et al. 2003). Compounds of the invention are considered active in the Rev-GFP assay outlined above if they have an $IC_{50}$ of less than about 10 M, with the most preferred compounds having an $IC_{50}$ of less than about 1 µM. The results of the RevGFP assay appear in Table 2.

Cell Proliferation Assay

The CellTiter 96® AQueous One Solution cell proliferation assay (Promega) was used on MM.1S multiple myeloma cell line to study the cytotoxic and cytostatic properties of the compounds. The assay is based on the cleavage of the tetrazolium salt, MTS, in the presence of an electron-coupling reagent PES (phenazine ethosulfate). The MTS tetrazolium compound is bioreduced by cells into a colored formazan product that is soluble in tissue culture medium. This conversion is presumably accomplished by NADPH or NADH produced by dehydrogenase enzymes in metabolically active cells. Assays are performed by adding a small amount of the CellTiter 96® AQueous One solution reagent directly to culture wells, incubating for 1-4 hours and then recording the absorbance at 490 nm with a 96-well plate reader. The absorbance revealed directly correlates to the cell number and their metabolic activity.

The cells were seeded at $5 \times 10^3$ to $1.5 \times 10^4$ cells in each well of a 96-well plate in 100 µL of fresh culture medium and adherent cells were allowed to attach overnight. The stock solutions of the compounds were diluted in cell culture medium to obtain eight concentrations of each drug, ranging from 1 nM to 30 µM and DMSO at less than 1% v/v was used as a negative control. The resulting drug solutions were transferred onto the cells. After 72 h of treatment, 20 µl of CellTiter 96® AQueous reagent was added into each well of the 96-well assay plates and the plate was incubated at 37° C. for 1-4 hours in a humidified, 5% $CO_2$ atmosphere. Then the absorbance of each well was recorded at 490 nm using a 96-well plate reader. In most cases, the assay was performed in triplicate and the results were presented as half maximal inhibitory concentration ($IC_{50}$). Optical density versus compound concentration was plotted and analyzed using non-linear regression equations (IDBS XLfit) and the $IC_{50}$ for each compound was calculated.

Pharmacokinetic (PK) Assay and Brain:Plasma Ratio Determination

AUC. Blood was collected from mice (N=3) to contribute to the total of 10 time points (pre-dose, 5 min, 15 min, 30 min, 1 hour, 2 hours, 4 hours, 8 hours, 12 hours and 24 hours post dose). Mice were bled on a rotating basis, each mouse contributing 3 time points to the blood collection. At the designated time points, animals were anaesthetized under isoflurane, and approximately 110 µL of blood per time point was collected via retro-orbital puncture into pre-cooled $K_2$EDTA (anti-coagulant) tubes. Blood samples were put on wet ice and centrifuged (2000 g, 5 min at 4° C.) to obtain plasma within 30 minutes of sample collection. All samples were stored frozen at approximately −80° C. until analysis. Prior to analysis, samples were mixed with internal standard (dexamethasone) in acetonitrile, vortexed, centrifuged, and supernatant was injected for analysis. Concentration of compounds in plasma was determined using LC-MS-MS instrumentation (API 4000, Triple Quadruple with electrospray ionization; Acuity Ultra Performance Liquid Chromatography column C18, with MeOH and formic acid as organic solvents). AUC values were calculated using WinNonlin Professional 6.2 software package, non-compartmental pharmacokinetic model NCA200.

Brain to Plasma (B:P) Ratio. A separate group of mice (N=3) were dosed (PO at 10 mg/kg) and then sacrificed at the time of maximal plasma concentration (estimated $T_{max}$ at 2 hours post-dose), at which time terminal plasma and brain tissue were collected. Following collection, brain tissue was rinsed with cold saline, dried on filter paper, weighed and snap-frozen by placing on dry ice. All samples were stored frozen at approximately −80° C. until analysis. At the time of analysis, brain tissue was homogenized (homogenizing solution PBS, pH 7.4), mixed with internal standard (dexamethasone) in acetonitrile, vortexed, centrifuged, and supernatant was injected for analysis of compound concentration using LC-MS-MS methodology (API 4000, Triple Quadruple with electrospray ionization; Acuity Ultra Performance Liquid Chromatography column C18, with MeOH and formic acid as organic solvents). Plasma samples were treated with the identical method (except homogenization step) and the concentration of compound in each matrix was calculated based on generated standard curves. The results of the PK assay and the BP ratio determination are presented in Table 2.

TABLE 2

Asay Results for Compounds of Formula I and Comparators Thereto (A = IC$_{50}$ value of <= 1 μM; B = IC$_{50}$ value from 1-10 μM; C = IC$_{50}$ value of >10 μM; NT = not tested).

| Cmpd. No. | Structure | Rev Export | Cytotoxicity Assay | AUC$_{Inf}$ (hr•ng/mL)* | B:P* |
|---|---|---|---|---|---|
| X-1** | 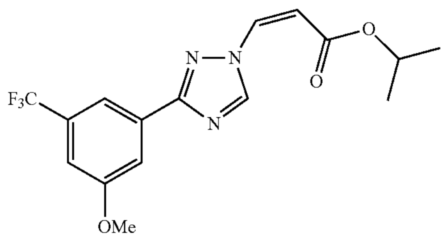 [SMILES: COc1cc(-c2ncn(/C=C\C(=O)OC(C)C)n2)cc(C(F)(F)F)c1] | A | A | 209‡ | NT |
| X-2*** | 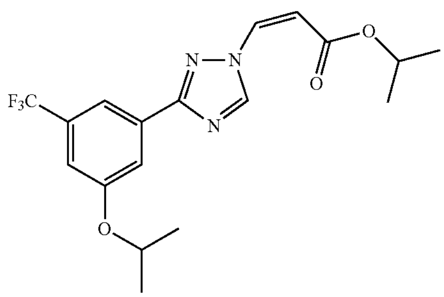 [SMILES: CC(C)OC(=O)/C=C\n1cnc(-c2cc(OC(C)C)cc(C(F)(F)F)c2)n1] | A | A | 68.3† | 1.27† |
| X-3 | 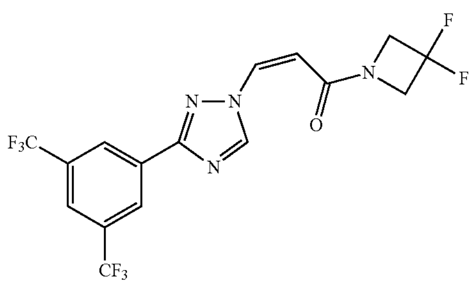 [SMILES: O=C(/C=C\n1cnc(-c2cc(C(F)(F)F)cc(C(F)(F)F)c2)n1)N1CC(F)(F)C1] | A | A | 12300 | 5.0 |
| I-3 | 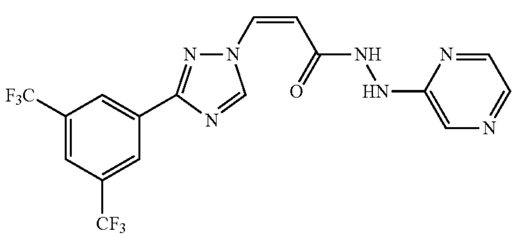 | A | A | 10100 | 0.71 |
| I-4 | 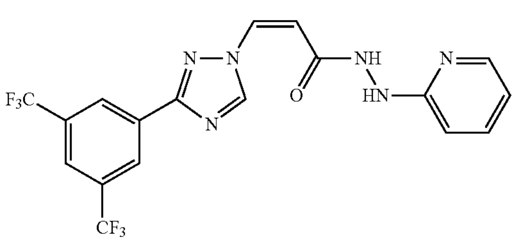 [SMILES: O=C(/C=C\n1cnc(-c2cc(C(F)(F)F)cc(C(F)(F)F)c2)n1)NNc1ccccn1] | A | A | 10800 | 1.8 |

TABLE 2-continued

Asay Results for Compounds of Formula I and Comparators Thereto (A = IC$_{50}$ value of <= 1 μM; B = IC$_{50}$ value from 1-10 μM; C = IC$_{50}$ value of >10 μM; NT = not tested).

| Cmpd. No. | Structure | Rev Export | Cytotoxicity Assay | AUC$_{Inf}$ (hr•ng/mL)* | B:P* |
|---|---|---|---|---|---|
| I-5 | 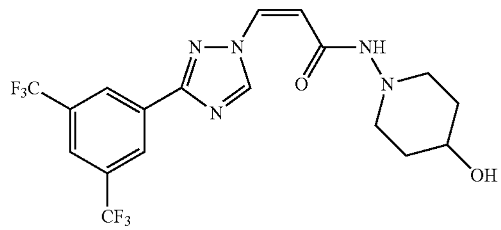 [SMILES: O=C(/C=C\n1cnc(-c2cc(C(F)(F)F)cc(C(F)(F)F)c2)n1)NN1CCC(O)CC1] | NT | A | 3850 | 1.4 |
| I-6 | 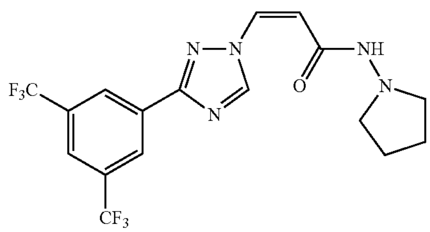 [SMILES: O=C(/C=C\n1cnc(-c2cc(C(F)(F)F)cc(C(F)(F)F)c2)n1)NN1CCCC1] | NT | A | NT | NT |
| I-7 | 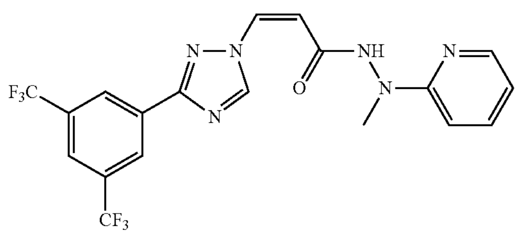 [SMILES: CN(NC(=O)/C=C\n1cnc(-c2cc(C(F)(F)F)cc(C(F)(F)F)c2)n1)c1ccccn1] | A | A | 12200 | 1.5 |
| I-8 | 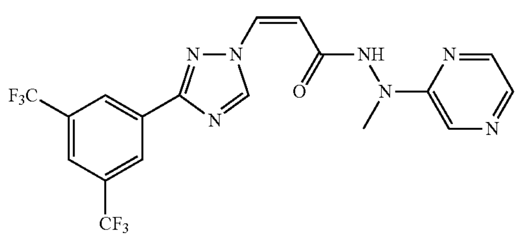 | A | A | 4600 | 2.1 |
| I-9 | 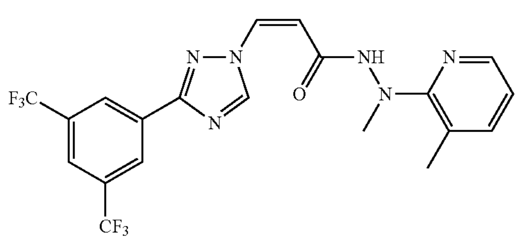 [SMILES: Cc1cccnc1N(C)NC(=O)/C=C\n1cnc(-c2cc(C(F)(F)F)cc(C(F)(F)F)c2)n1] | NT | A | NT | NT |
| I-10 | 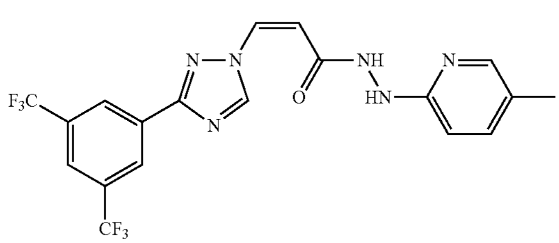 [SMILES: Cc1ccc(NNC(=O)/C=C\n2cnc(-c3cc(C(F)(F)F)cc(C(F)(F)F)c3)n2)nc1] | NT | A | 4170 | 0.77 |

TABLE 2-continued

Asay Results for Compounds of Formula I and Comparators Thereto (A = IC$_{50}$ value of <= 1 µM; B = IC$_{50}$ value from 1-10 µM; C = IC$_{50}$ value of >10 µM; NT = not tested).

| Cmpd. No. | Structure | Rev Export | Cytotoxicity Assay | AUC$_{Inf}$ (hr•ng/mL)* | B:P* |
|---|---|---|---|---|---|
| I-11 | 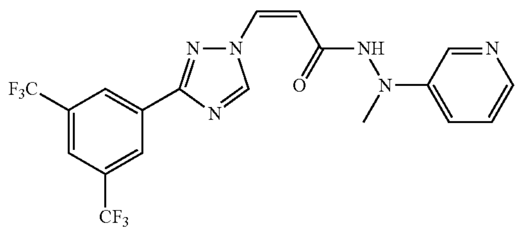 [SMILES: CN(NC(=O)/C=C\n1cnc(-c2cc(C(F)(F)F)cc(C(F)(F)F)c2)n1)c1cccnc1] | NT | A | NT | NT |
| I-12 | 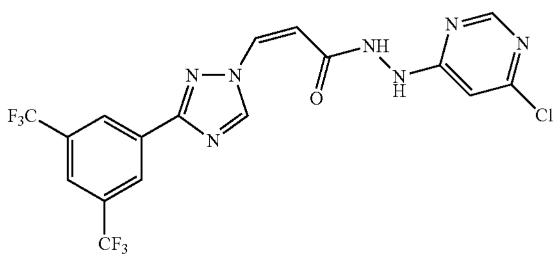 [SMILES: O=C(/C=C\n1cnc(-c2cc(C(F)(F)F)cc(C(F)(F)F)c2)n1)NNc1cc(Cl)ncn1] | A | A | 24900 | 0.13 |
| I-13 | 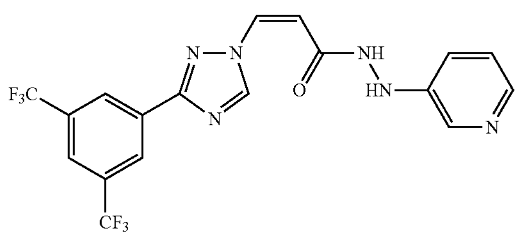 | NT | A | NT | NT |
| I-14 | 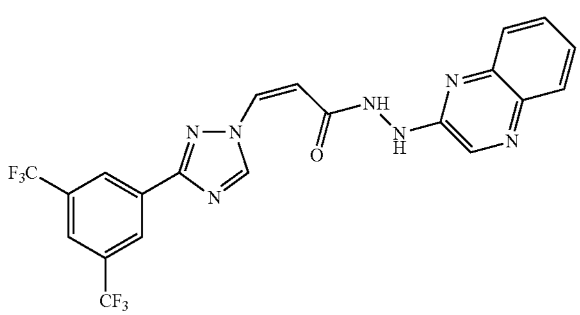 [SMILES: O=C(/C=C\n1cnc(-c2cc(C(F)(F)F)cc(C(F)(F)F)c2)n1)NNc1cnc2ccccc2n1] | NT | A | NT | NT |
| I-15 | 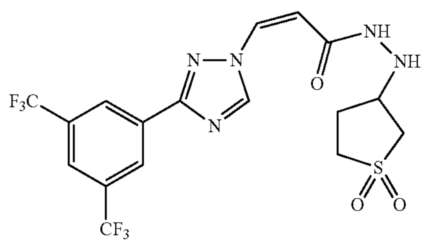 [SMILES: O=C(/C=C\n1cnc(-c2cc(C(F)(F)F)cc(C(F)(F)F)c2)n1)NNC1CCS(=O)(=O)C1] | NT | A | NT | NT |

TABLE 2-continued

Assay Results for Compounds of Formula I and Comparators Thereto (A = IC$_{50}$ value of <= 1 μM; B = IC$_{50}$ value from 1-10 μM; C = IC$_{50}$ value of >10 μM; NT = not tested).

| Cmpd. No. | Structure | Rev Export | Cytotoxicity Assay | AUC$_{Inf}$ (hr•ng/mL)* | B:P* |
|---|---|---|---|---|---|
| I-16 | 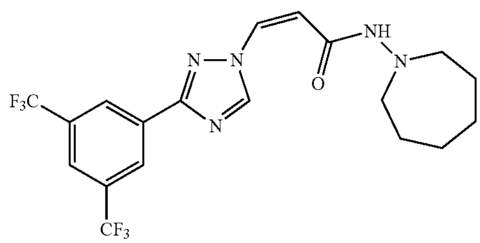 [SMILES: O=C(/C=C\n1cnc(-c2cc(C(F)(F)F)cc(C(F)(F)F)c2)n1)NN1CCCCCC1] | NT | A | NT | NT |
| I-17 | 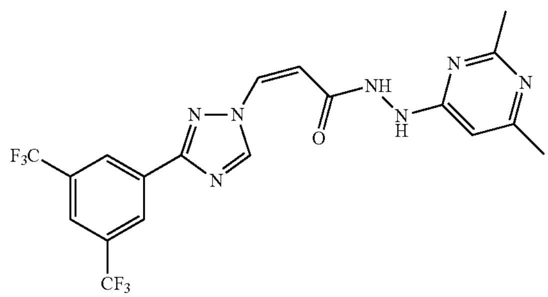 [SMILES: Cc1cc(NNC(=O)/C=C\n2cnc(-c3cc(C(F)(F)F)cc(C(F)(F)F)c3)n2)nc(C)n1] | NT | A | NT | NT |
| I-18 | 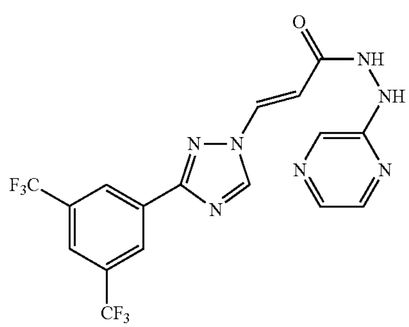 [SMILES: O=C(/C=C/n1cnc(-c2cc(C(F)(F)F)cc(C(F)(F)F)c2)n1)NNc1cnccn1] | NT | A | 7140 | 0.28 |
| I-19 | 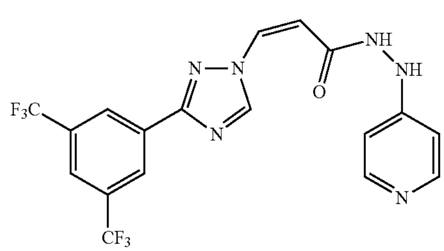 [SMILES: O=C(/C=C\n1cnc(-c2cc(C(F)(F)F)cc(C(F)(F)F)c2)n1)NNc1ccncc1] | NT | A | 4020 | 0.2 |
| I-20 | 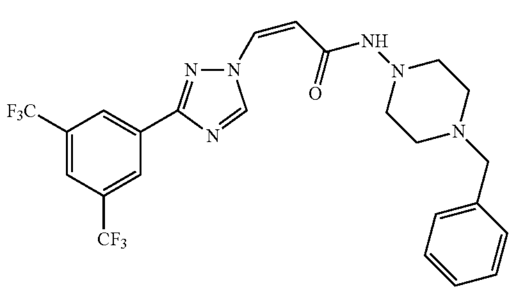 [SMILES: O=C(/C=C\n1cnc(-c2cc(C(F)(F)F)cc(C(F)(F)F)c2)n1)NN1CCN(Cc2ccccc2)CC1] | NT | A | NT | NT |

TABLE 2-continued

Asay Results for Compounds of Formula I and Comparators Thereto (A = $IC_{50}$ value of <= 1 μM; B = $IC_{50}$ value from 1-10 μM; C = $IC_{50}$ value of >10 μM; NT = not tested).

| Cmpd. No. | Structure | Rev Export | Cytotoxicity Assay | $AUC_{Inf}$ (hr•ng/mL)* | B:P* |
|---|---|---|---|---|---|
| I-21 | 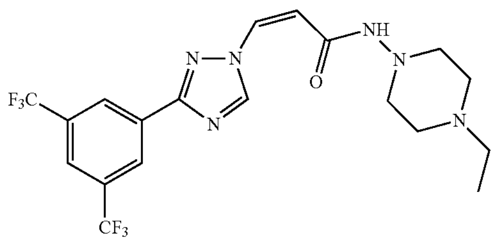 [SMILES: CCN1CCN(NC(=O)/C=C\n2cnc(-c3cc(C(F)(F)F)cc(C(F)(F)F)c3)n2)CC1] | NT | A | NT | NT |
| I-22 | 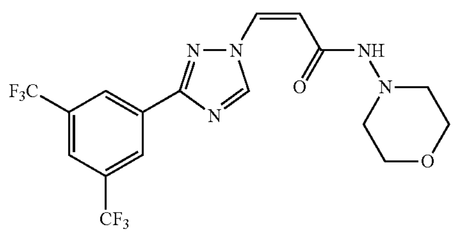 [SMILES: O=C(/C=C\n1cnc(-c2cc(C(F)(F)F)cc(C(F)(F)F)c2)n1)NN1CCOCC1] | NT | A | NT | NT |
| I-23 | 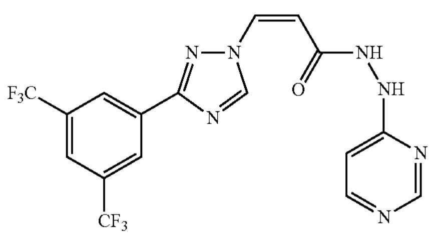 [SMILES: O=C(/C=C\n1cnc(-c2cc(C(F)(F)F)cc(C(F)(F)F)c2)n1)NNc1ccncn1] | NT | A | NT | NT |
| I-24 | 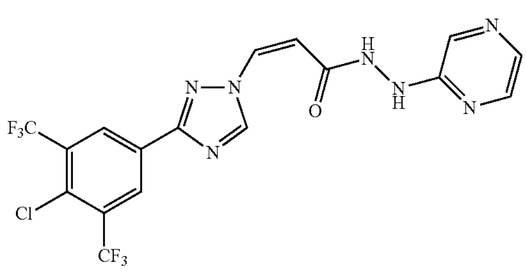 [SMILES: O=C(/C=C\n1cnc(-c2cc(C(F)(F)F)c(Cl)c(C(F)(F)F)c2)n1)NNc1cnccn1] | NT | A | 3350 | 0.7 |
| I-25 | 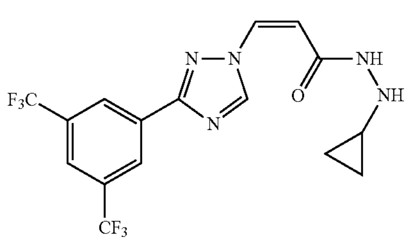 [SMILES: O=C(/C=C\n1cnc(-c2cc(C(F)(F)F)cc(C(F)(F)F)c2)n1)NNC1CC1] | NT | A | NT | NT |

TABLE 2-continued

Asay Results for Compounds of Formula I and Comparators Thereto (A = $IC_{50}$ value of <= 1 μM; B = $IC_{50}$ value from 1-10 μM; C = $IC_{50}$ value of >10 μM; NT = not tested).

| Cmpd. No. | Structure | Rev Export | Cytotoxicity Assay | $AUC_{Inf}$ (hr•ng/ mL)* | B:P* |
|---|---|---|---|---|---|
| I-26 | 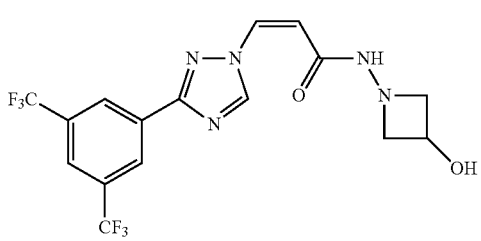 [SMILES: O=C(/C=C\n1cnc(-c2cc(C(F)(F)F)cc(C(F)(F)F)c2)n1)NN1CC(O)C1] | NT | A | NT | NT |

*Dosed in mice at 10 mg/kg po.
**Compound 26 from US 2009/0275607.
***Compound 44 from US 2009/0275607.
‡$AUC_{Inf}$ values for compound X-1 dosed in mice at 10 mg/kg po were below the limit of quantitation. Data reported for 5 mg/kg iv.
†Dosed in rats at 10 mg/kg po.

The $AUC_{Inf}$ for compound X-1 was below the limit of detection when dosed in mice at 10 mg/kg po. When dosed at 5 mg/kg iv, compound X-1 showed minimal exposure, as indicated by the low $AUC_{Inf}$ of 209 hr·ng/mL. The brain to plasma ratio for compound X-1 was not determined due to its negligible exposure levels when dosed po.

The $AUC_{Inf}$ for compound X-2 was calculated to be 68.3 hr·ng/mL when dosed in rats at 10 mg/kg po. Such exposure levels are exceedingly low when compared to compound X-3 and compounds of formula I of the present invention. However, compound X-2 exhibits a moderate brain to plasma ratio. The low $AUC_{Inf}$ coupled with a non-negligible brain to plasma ratio suggests that compound X-2 can cross the BBB despite the low exposure levels. It is believed that Compound X-2 would have a significantly higher brain to plasma ratio if its $AUC_{Inf}$ were increased.

The $AUC_{Inf}$ for compound X-3 was calculated to be 12300 hr·ng/mL when dosed in rats at 10 mg/kg po, indicating good exposure. However, compound X-3 demonstrated a high B:P ratio of 5.0.

The compounds of Formula I are characterized by $AUC_{Inf}$ of greater than about 3300 hr·ng/mL, in most instances greater than about 3500 hr·ng/mL, and a relatively low B:P ratio (<2.5). Generally, greater exposure levels of a therapeutic agent increase the likelihood of brain penetration. It is therefore surprising and unexpected that compounds of formula I exhibit high $AUC_{Inf}$ levels and relatively low brain to plasma ratios.

In Vivo and In Vitro Activity of Compounds of the Invention Against Breast Cancer Basal-like breast cancers (BLBC) compose up to 15% of breast cancer (BC) and are usually triple negative breast cancer (TNBC) and characterized by lack of ER, progesterone receptor PR, and HER-2 amplification. In addition, most BRCA1-associated BCs are BLBC and TNBC, expressing basal cytokeratins and EGFR. BLBC is characterized by an aggressive phenotype, high histological grade, and poor clinical outcomes with high recurrence and metastasis rates. Additional therapies are needed. The activity of the compounds of the invention, for example, Compound I-3 was assessed in various breast cancer cell lines both in vitro and in vivo.

Inhibition of TNBC (Triple Negative Breast Cancer) Xenograft In Vivo

MDA-MB-468 (ATCC #HTB-132) triple negative breast cancer cells were obtained from ATCC. These cells were grown in Leibovitz's L-15 medium supplemented with 10% fetal calf serum (FCS), 1% penicillin and streptomycin, and 2 mM L-glutamine. Cells were sub-cultured by dilution at a ratio of 1:3. Fifty (50) female SCID mice (Charles River Labs), aged 5 to 6 weeks, with a mean pre-treatment body weight of 19.2 grams were used. SCID mice were inoculated s.c. in the left flank with $5 \times 10^6$ MDA-MB-468 cells. When the tumors reached a mean size of between 100 and 200 $mm^3$, mice were randomly and prospectively divided into a vehicle control group of ten (10) mice and five treatment groups of eight (8) mice per group. The groups were as follows:

Vehicle (1% Pluronic, 1% PVP in distilled water)
5 FU 50 mg/kg
Compound I-3 5 mg/kg Monday (M), Wednesday (W), Friday (F)
Compound I-3 15 mg/kg, M, W, F
Compound 1-3 25 mg/kg M, W, F
Compound 1-3 25 mg/kg M, Thursday (Th).

All administrations were via the oral route. Animals were fed with sterile Labdiet© 5053 (pre-sterilized) rodent chow and sterile water was provided ad libitum. Tumors were measured once every two days with micro-calipers, and tumor volume was calculated as (length×width×width)/2. All animals were weighed every day in order to assess differences in weight among treatment groups and monitor wellness of animals. Any animals exhibiting a loss of greater than 20% of starting weight during the course of the study were euthanized. Any animals with a tumor over 1500 $mm^3$ in volume were also euthanized. Survival was recorded daily. Dosing solutions were prepared freshly each day. Compound 1-3 was supplied as a lyophilized powder containing 67.8% drug product with the balance made up of Pluronic F-68 and PVP K29/32. This was prepared by dissolving the lyophilized powder at a rate of 6.64 mg/90 μL in sterile water, and diluting as necessary in vehicle (1% Pluronic F-68 and 1% PVP K29/32) in sterile water. All dosing solutions of Compound I-3 were dosed at 0.1 mL/10 g. Statistical differences between treatment groups were determined using Mann-Whitney Rank Sum or ANOVA tests with a critical value of 0.05.

On day 33 post inoculation, the tumors were excised. FIG. 1 is a graph of tumor volume as a function of time and shows that Compound 1-3 displayed efficacy in a dose dependent manner, inhibiting from approximately 60% (5 mg/kg Monday, Wednesday, Friday) to nearly 100% of tumor growth (for 25 mg/kg Monday, Thursday regimen) compared with vehicle-treated animals. In addition, Compound 1-3 was well tolerated.

Upon excision, the tumors were also stained for the tumor suppressor proteins (TSPs) FOXO3a, IκB, and p27, and nuclear localization of the TSPs was confirmed by immunohistochemistry.

Inhibition of Proliferation and Cytotoxicity in TNBC and Luminal BC Cell Lines

The CellTiter 96® AQueous One Solution cell proliferation assay (Promega) was used to study the cytotoxic and cytostatic properties of Compound I-3 in various TNBC and luminal BC cell lines.

The cells were seeded at $5\times10^3$ to $1.5\times10^4$ cells (depending on cell type) in each well of a 96-well plate in 100 µL of fresh culture medium and adherent cells were allowed to attach overnight. The stock solutions of the compounds were diluted in cell culture medium to obtain eight concentrations of each drug, ranging from 1 nM to 30 µM and DMSO at less than 1% v/v was used as a negative control. The resulting drug solutions were transferred onto the cells. After 72 h of treatment, 20 µl of CellTiter 96® AQueous reagent was added into each well of the 96-well assay plates and the plate was incubated at 37° C. for 1-4 hours in a humidified, 5% $CO_2$ atmosphere. Then the absorbance of each well was recorded at 490 nm using a 96-well plate reader. In most cases, the assay was performed in triplicate and the results were presented as half maximal inhibitory concentration ($IC_{50}$). Optical density versus compound concentration was plotted and analyzed using non-linear regression equations (Excel Fit) and the $IC_{50}$ for each cell line against Compound 1-3 was calculated.

The results of the cell proliferation assay are shown in Table 3. The results demonstrate the potent cytotoxicity of Compound I-3 on nine of fifteen BC cell lines tested. The compound was considered potent in a cell line if it had an $IC_{50}$ value of less than about 1.0 µM. Cell lines in which Compound 1-3 had an $IC_{50}$ value of less than 1.0 µM were considered sensitive cell lines, while cell lines in which Compound 1-3 had an $IC_{50}$ value of greater than 1.0 µM were considered resistant cell lines. Seven of the nine sensitive cell lines were TNBC. Genomic analyses on all BC lines indicated that p53, PI3K/AKT and BRCA1 or 2 status did not affect cyotoxicity.

TABLE 3

$IC_{50}$ values for Compound I-3 in various breast cancer cell lines.

| Cell Line | Type | $IC_{50}$ (µM) |
| --- | --- | --- |
| MDA-MB-468 | BaB | 0.01 |
| MDA-MB-231 | BaB | 0.01 |
| DU4475 | Lu | 0.013 |
| BT-549 | BaB | 0.02 |
| MCF12A | BaB | 0.15 |
| MCF10A | BaB | 0.18 |
| UACC812 | Lu | 0.59 |
| HCC-1143 | BaA | 0.6 |
| HCC-1569 | BaA | 0.96 |
| MDA-MB-157 | BaB | 1.3 |

TABLE 3-continued $IC_{50}$ values for Compound I-3 in various breast cancer cell lines.

| Cell Line | Type | $IC_{50}$ (µM) |
| --- | --- | --- |
| HS578T | BaB | 1.5 |
| BT-20 | BaA | 1.5 |
| HCC-202 | Lu/HER+ | 5.2 |
| HCC-1428 | Lu | 10.4 |
| ZR7530 | Lu/HER+ | 19 |

Compound I-3 Induces Apoptosis and Inhibits Long-Term BC Growth

The ability of Compound 1-3 to induce apoptosis and to inhibit the long-term growth of selected BC cell lines was assessed.

MDA-MB-468 TNBC, DU4475 and HS578T TNBC cells were exposed to concentrations of Compound 1-3 ranging from 0 to 10 µM for 24 hours. After 24 hours, whole protein cell extracts were run on immunoblots and were exposed to antibodies against the proteins indicated in FIGS. 2A-2C.

FIGS. 2A-2C are images of immunoblots obtained from a few of the most resistant and most sensitive breast cancer cell lines described above, including MDA-MB-468 TNBC, DU4475 and HS578T TNBC. The study shows that Compound 1-3 induces apoptosis in the sensitive TNBC and luminal BC cell lines (MDA-MB-468 and DU4475, respectively) after 24 hours, as indicated by the decrease in PARP and caspase 3, two apoptosis markers, and the increase in cleaved PARP and cleaved caspase 3. In contrast, only a negligible increase in cleaved PARP and cleaved caspase 3 was observed when a resistant cell line, HS578T, was treated with Compound I-3.

Long-term growth assays were also conducted, in which MDA-MB-468, MDA-MB-231 and HS578T cells were treated with 1 µM Compound I-3 and incubated for 7 (HS578T) or 10 (MDA-MB-468 and MDA-MB-231) days. At the end of the assay, media was removed from the cells and the remaining cells were stained with crystal violet. The study showed that Compound I-3 inhibited the long-term growth of all three cell lines, including both sensitive (MDA-MB-468 and MDA-MB-231) and resistant (HS578T) BC cell lines.

Compound I-3 Increases Nuclear FOXO3a and IκB in TNBC Cell Lines

MDA-MB-468 TNBC Basal A and BT-20 TNBC Basal B cells were exposed to DMSO or 1 µM Compound 1-3 for 24 hours and then stained for FOXO3a or IκB with or without DAPI nuclear stain. The stained cells were examined for nuclear localization. Following treatment with Compound I-3, both FOXO3a and IκB were localized in the cell nucleus, while in DMSO-treated cells, both FOXO3a and IκB were localized in the cytoplasm.

Effect of Compound I-3 on Anti-Apoptosis and Cell Cycle Proteins in Two TNBC Lines The effect of increasing concentrations of Compound I-3 on MDA-MB-468 and HS578T cells was examined. MDA-MB-468 and HS578T cells were exposed to increasing concentrations of Compound I-3 for 24 hours and total cellular protein levels of various proteins was probed with antibodies against the proteins indicated in FIG. 3.

Figure 3:
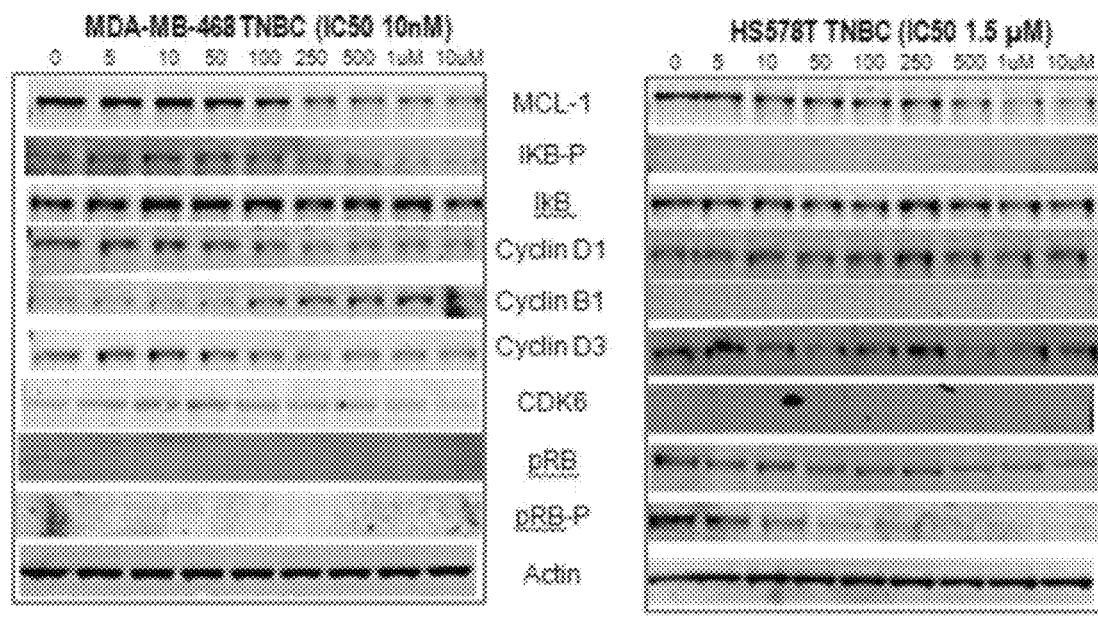
FIG. 3 is Western blot images showing the effect of increasing concentrations of Compound 1-3 on anti-apoptosis and cell cycle proteins in MDA-MB-468 and HS578T TNBC cell lines.

FIG. 3 shows that, despite the approximately 100-fold difference in the $IC_{50}$ of Compound 1-3 in the two cell lines after 72 hours (10 nM versus 1.5 µM), a reduction in MCL-1 is observed in both cell lines in response to increasing concentrations of Compound I-3.

The experiments described in Example 32 indicate that inhibition of CRM1-mediated nuclear export by the compounds of the invention, including Compound I-3, induces nuclear localization and activation of tumor suppressor gene proteins, resulting in selective apoptosis, cancer cell cytotoxicity and tumor growth inhibition.

Example 33: Monoclonal-Antibody Induced Arthritis (CAIA)

BalbC mice were randomly assigned to cages on arrival Day (−1) and each group (n=8) was assigned to the treatment groups shown below with the following regimen:
Vehicle: PO Day 4, 6, 8, 10
Dexamethasone: 1 mg/kg IP Days 4, 6, 8, 10
Compound I-4: 4 mg/kg PO, Day 4, 6, 8, 10
Compound I-4: 7.5 mg/kg PO, Day 4, 6, 8, 10
Compound I-4: 15 mg/kg PO, Day 4, 6, 8, 10

The health status of the animals was examined on arrival. Only animals in good health were acclimatized to laboratory conditions and were used in the study. Animals were provided ad libitum a commercial rodent diet and free access to drinking water, supplied to each cage via polyethylene bottles with stainless steel sipper tubes. Automatically controlled environmental conditions were set to maintain temperature at 20-24° C. with relative humidity (RH) of 30-70%, a 12:12 hour light:dark cycle and 10-30 air changes/hr in the study room Temperature, RH and light cycle were monitored daily by the control computer. Animals were given a unique animal identification number and on Day 0 of the study each animal received a tail vein injection of antibody cocktail (200 uL of 10 mg/mL). The antibody cocktail was supplied by MD Biosciences (Catalog #: CIA-MAB-50). On day 3, post the single mAb administration, all animals were subjected to LPS (200 uL of 0.5 mg/mL) administration by a single intraperitoneal (IP) injection. LPS was supplied by MD Biosciences (Catalog #: MDLPS.5). Mice were examined for signs of arthritogenic responses in peripheral joints on day 0. From disease onset, arthritogenic response will be examined on study days 3-8, 10, and 12. Arthritis reactions are reported for each paw according to a 0-4 scale in ascending order of severity.

| Arthritis Score | Grade |
| --- | --- |
| No reaction normal | 0 |
| Mild, but definite redness and swelling of the ankle/wrist or apparent redness and swelling limited to individual digits, regardless of the number of affected digit | 1 |
| Moderate to severe redness and swelling of the ankle/wrist | 2 |
| Redness and swelling of the entire paw including digits | 3 |
| Maximally inflamed limb with involvement of multiple joints | 4 |

Animals found in a moribund condition, animals with broken skin on an arthritic paw, or with a greater than a 20% decrease in body weight and animals showing severe pain and enduring signs of severe distress were humanely euthanized. Severe pain or distress was assessed on a case by case basis by experienced animal technicians. Briefly however, assessments looked for abnormal vocalizations, isolation from other animals, unwillingness to use limbs, abnormal response to handling, tremors and posture. Animals were euthanized by $CO_2$ inhalation followed by cervical dislocation. Evaluation is primarily based on the mean values for arthritis scoring and paw thickness measurements. Statistical analysis was also be carried out on body weight. Where appropriate, analysis of the data by ANOVA with Tukey post hoc analysis was applied to determine significance of treatment effects.

Figure 4:
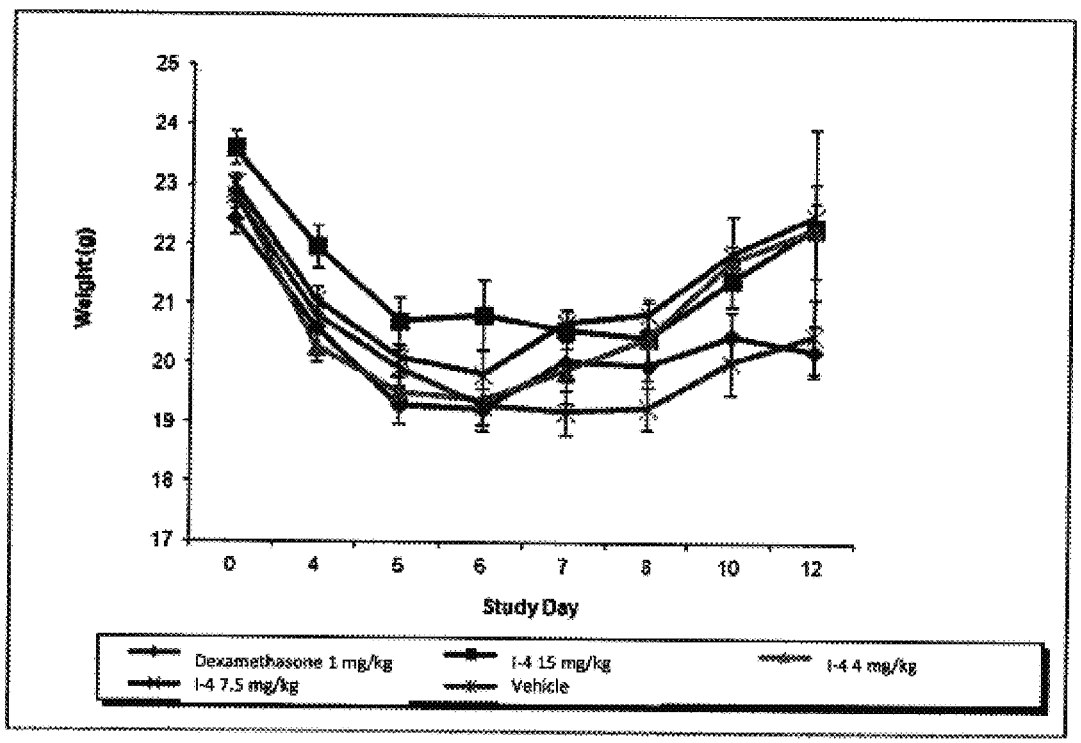
FIG. 4 is a graph of mean body weight versus time for days 0 to 12 in antibody-induced male BALB/c arthritic mice subjected to the indicated treatment.

As part of this model, animals lose weight quickly for the first 5-8 days and slowly start gaining/losing weight depending on the disease progression. 1-4 increased the rate of weight gain compared to vehicle or dexamethasone treatment groups. FIG. 4 is a graph of mean body weight versus time for days 0 to 12 in the antibody-induced male BALB/c arthritic mice subjected to the model.

Figure 5:
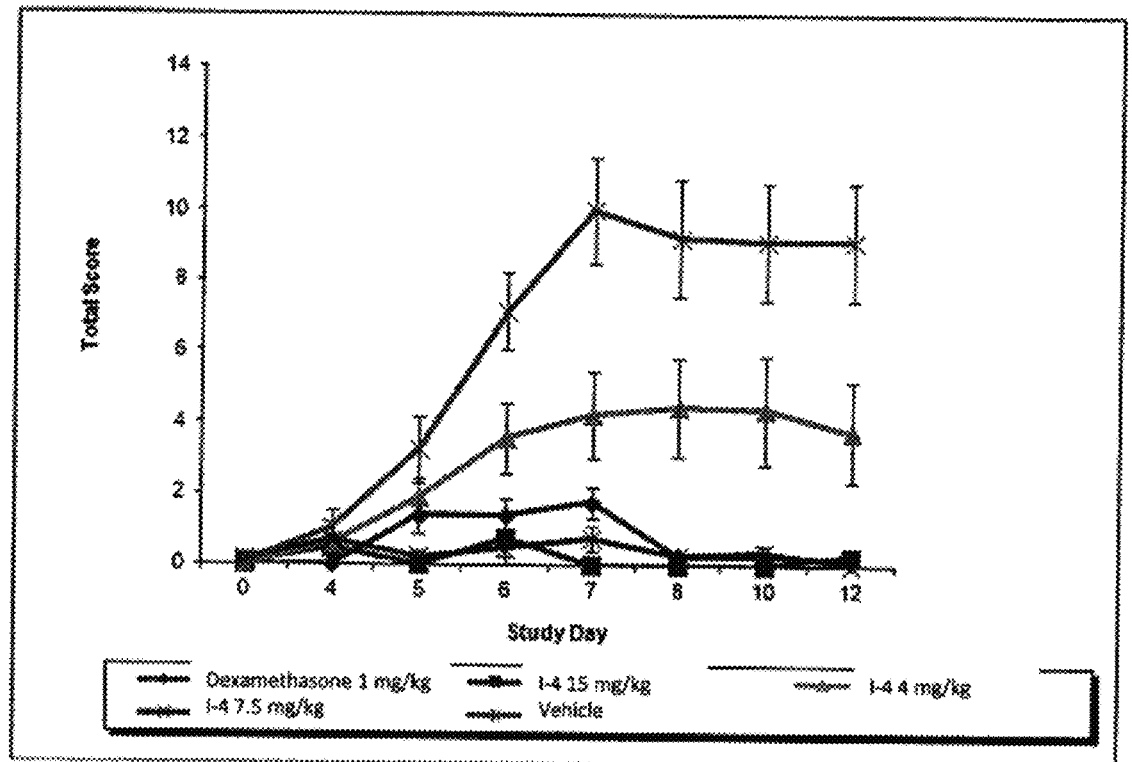
FIG. 5 is a graph of mean total paw clinical arthritic scores versus time for days 0 to 12 in antibody-induced male BALB/c arthritic mice subjected to the indicated treatment.

In addition, animals subjected to the CAIA model typically begin to display signs of arthritis around Day 4 and as the disease progresses total arthritis scores increase as a function of time. Treatment with Compound I-4 significantly decreased the total score when compared with vehicle and displayed a dose dependent effect. FIG. 5 is a graph of mean total paw clinical arthritic scores versus time for days 0-12 in antibody-induced male BALB/c arthritic mice subjected to the indicated treatment.

Example 34: PMA Induced Psoriasis Model

BALB/c mice were housed in individually ventilated cages in a controlled environment (temperature 22±1° C., humidity 70±5%, and 12 h light/12 h dark cycle) in the animal facility. The mice had access to commercially available feed pellets and UV-treated potable water ad libitum. 4 mice were housed per individually ventilated cage. Each animal in the cage was identified by a tail. 8 mice per group mice were randomized into different treatment groups according to body weight. Following randomization the mean body weight for all groups was equivalent. Study design was Group 1: Naïve, 1% DMSO vehicle (10-30 ul, topical once daily), Group 2: PMA, 1% DMSO vehicle (10-30 ul, topical once daily), Group 3: PMA, 1-4 10 mg/kg in PVP/Pluronics (oral, M-W-F; Day 1-Day 3-Day 5-Day 7), Group 4: PMA, 0.1% betamethasone—25 mg (reference standard) (topical once daily)

4 ug Phorbol 12-myristate 13-acetate (PMA) in 20 uL of acetone was applied every day to mouse ears. Starting from Day 2, PMA-induction of dermal inflammation/psoriasis manifested with increases in clinical disease activity index associated with increased thickness of ear, scaling of ear-skin, and folding of ear-skin. The following parameters were evaluated: (i) the thickness of the ear, (ii) scaling on the skin of ear. This will be based on a scoring index—0, no scaling; 1, mild scaling; 2, moderate scaling; 3, severe scaling. (iii) folding on the skin of the ear. This will be based on a scoring index—0, no folding; 1, mild folding; 2, moderate folding; 3, severe folding, (iv) the weight of the ear (on sacrifice day).

Figure 6:
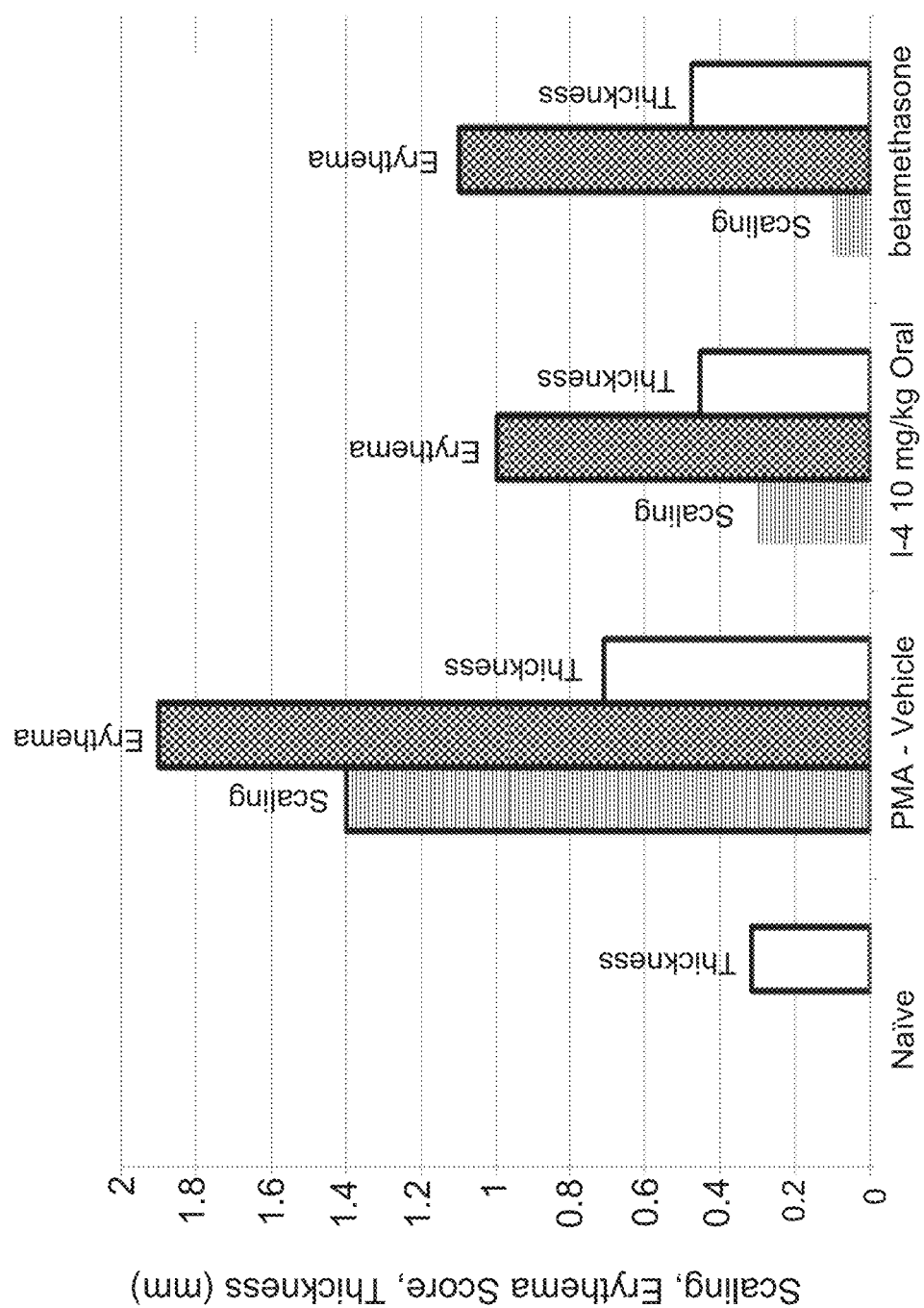
FIG. 6 is a bar graph of scoring for mean ear thickness, scaling and folding determined from day 0 to 7 in PMA-induced male BALB/c psoriatic mice subjected to the indicted treatment.

FIG. 6 is a bar graph providing scoring for thickness of the ear, scaling of the skin on the ear and folding of the skin of the ear. The results show that oral administration of Compound I-4 at 10 mg/kg reduced mean ear thickness in a statistically significant manner compared to vehicle. Efficacy obtained with I-4 was comparable to positive control betamethasone. In addition, Compound I-4 was well tolerated.

Example 35: Novel Object Recognition

For novel object recognition test, Zucker rats were placed into a test chamber (dimension 26"×18"×18"; L×W×H). Food and water was not be permitted during the test. The test had 3 phases: a) Familiarisation phase: Rats were singly placed in test chamber and allowed to freely explore for 60 min. The distance travelled by the animal during this phase was recorded using tracking software (AnyMaze system). The purpose of this phase was to familiarise the animals to the test apparatus. This test phase was conducted on day 1. b) Sample phase: On day 2, the rats were singly placed in the test chamber for 3 min and allowed to freely explore the test arena which contained 2 identical novel objects (e.g metal cube, plastic cylinder) positioned at 2 corners of the test chamber. The distance travelled by the animal during this sample phase was automatically recorded, as well as the time spent by the animal interacting with the novel objects, using a tracking software system and visual observation. Interaction with the object was defined as active interaction with the animals snout in contact or immediate proximity to the object. c) Test phase: 1 h after the sample phase, the rats were singly returned to the test chamber for 3 min and allowed to freely explore the test arena which contained 2 objects, one of which was the object presented during the sample phase, and the second a novel object which was unique to the test phase. The 2 objects were positioned at the same 2 corners of the test chamber as used for the sample phase. The distance travelled by the animal during the test phase was automatically recorded, as well as the time spent by the animal interacting with the novel and familiar objects, using a tracking software system and visual observation. Object interaction scores during both the sample and test phase were independently recorded by 2 observers. The final score represents the difference score between each reading. Object preference scores presented as D1 (i.e time spent exploring novel object—time spent exploring familiar object; therefore positive score represents novel object preference), and D2 (i.e D1/a+b; D1 score divided by overall object exploration time).

Figure 7:
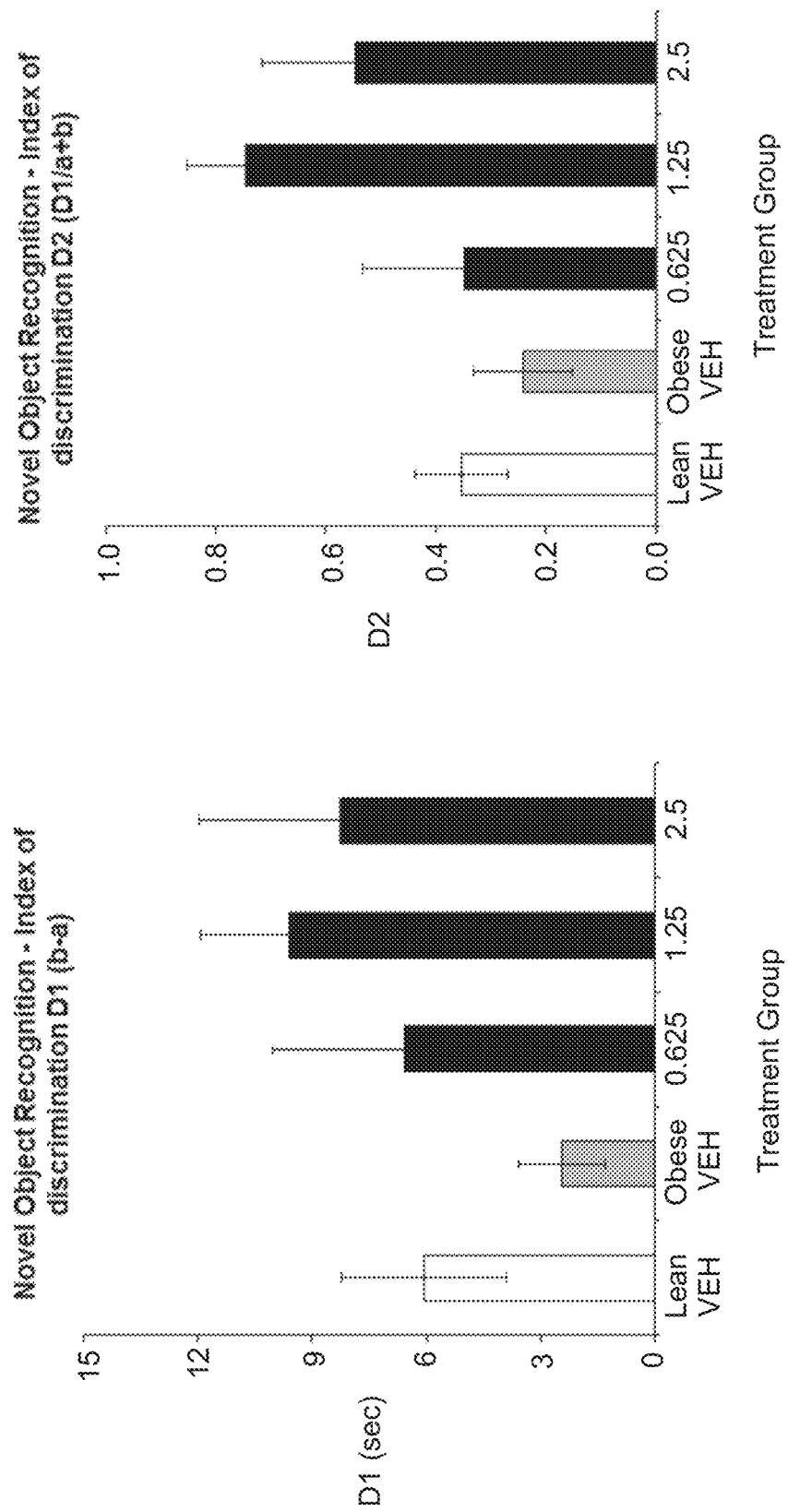
FIG. 7 is a set of graphs showing object preference of rats treated as indicted in the Novel Object Recognition Model.

FIG. 7 provides a set of graphs showing object preference of untreated and I-4 treated Zucker rats. From FIG. 7 it can be seen that Compound I-4 orally administered at 0.625, 1.25 and 2.5 mg/kg doses induced trends of improved novel object recognition in Zucker rats and I-4 was well tolerated.

Example 36: Obese Zucker Rats Feeding Study

Male Zucker (fa/fa) rats and male Zucker lean rats (both from Charles River) at 10 weeks of age—a timepoint at which the Zucker fa/fa rats should show elevated food intake, body mass and elevated plasma lipid profile relative to their "lean" counterparts were singly housed in plastic bottomed cages and were given 14 days of habituation. During this period, animal body weight, food and water intakes were recorded daily. All animals were given ad-lib access to standard lab chow and water throughout the study. Once the 14 day baseline intake data were collected, the Zucker obese rats were assigned into treatment groups based on equivalent baseline data, i.e. all Zucker obese rats had equivalent daily food/water intakes and body weights. During this phase the rats also received two vehicle administrations as familiarisation to the dosing procedure. Immediately after the baseline phase, the treatment phase commenced. Test article and vehicle were administered at approximately 1 h prior to onset of the dark cycle. Dose scheduling varied according to group: 5× weekly dosing was Monday-Friday The study design was the following: Group A=Zucker lean male rats, vehicle treatment 5× week, oral, n=6, Group B=Zucker obese male rats, vehicle treatment 5× week, oral, n=6, Group C=Zucker obese male rats, I-4 2.5 mg/kg 5× week, oral, n=6.

Daily body weight, food and water intake were measured at approximately the same time of the day. At day −1 and day 7 of treatment phase.

Figure 8A:
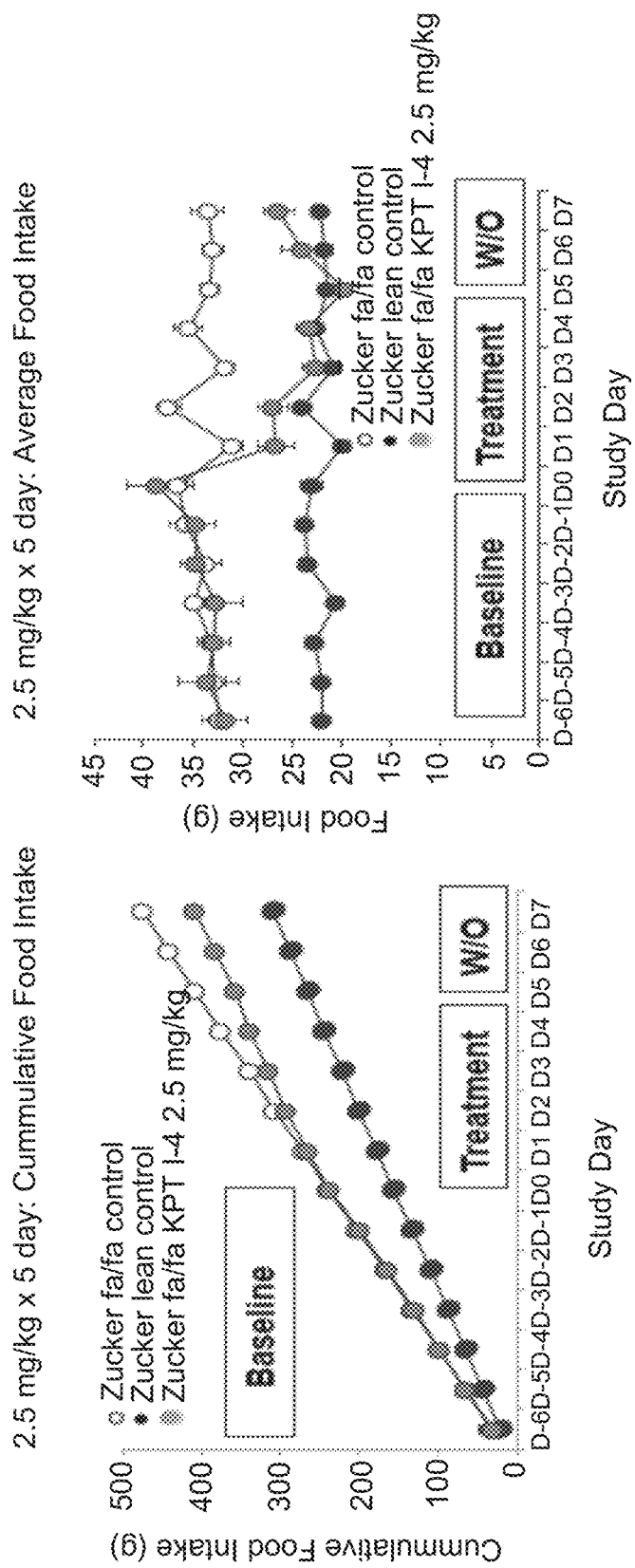
FIG. 8A is a set of graphs showing cumulative and average food intake versus time in obese and lean Zucker rats treated as indicated.

FIG. 8A provides cumulative and average food intake in obese and lean Zucker rats (W/O indicates washout period). Oral administration of Compound 1-4 at 2.5 mg/kg 5× weekly reduced mean and cumulative food intake in obese (fa/fa) Zucker rats. Compound I-4 was well tolerated.

Figure 8B:
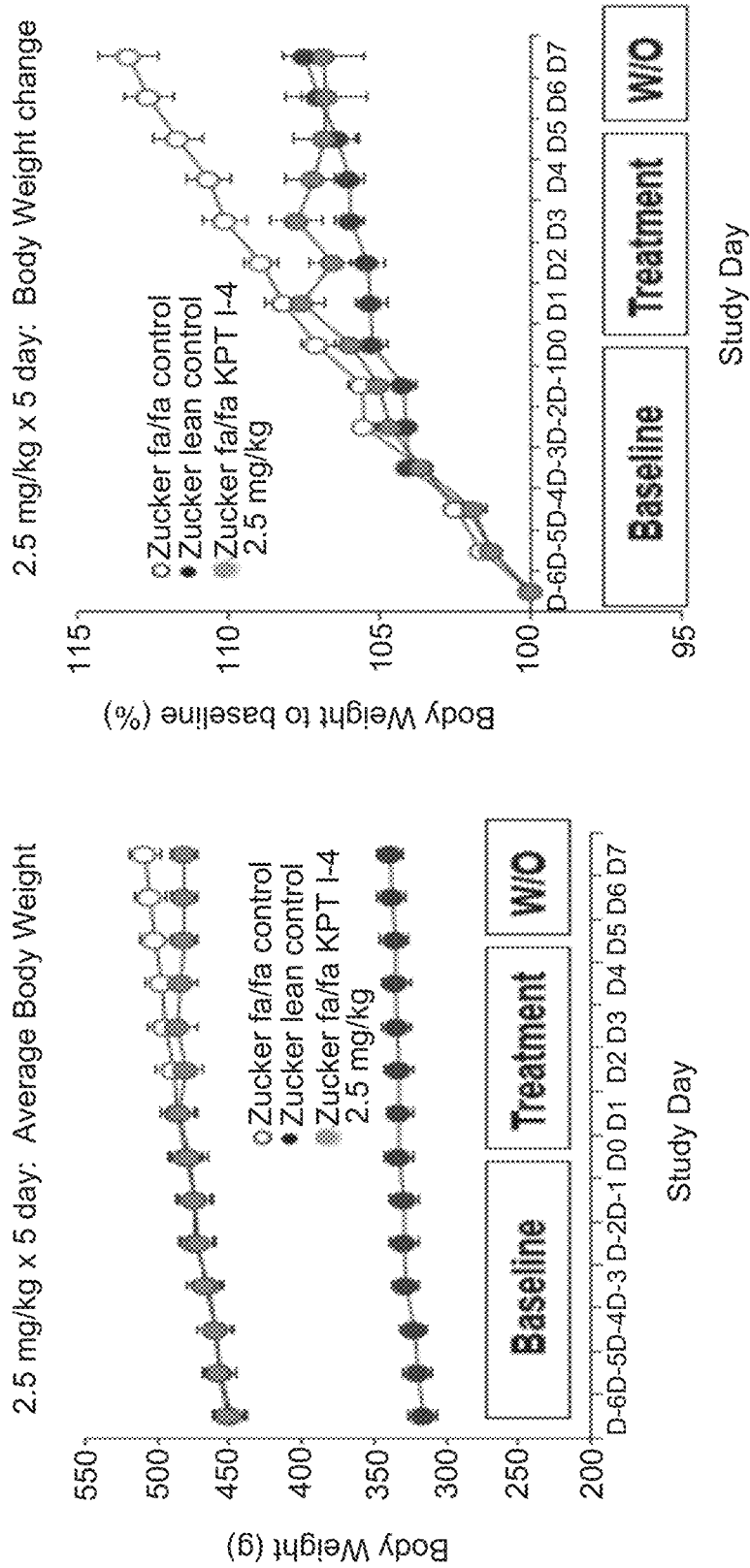
FIG. 8B is a set of graphs showing average and percent body weight versus time in obese and lean Zucker rats treated as indicated.

FIG. 8B provides average and percent body weight in obese and lean Zucker rats (W/O indicates washout period). Oral administration of I-4 at 2.5 mg/kg 5× weekly significantly reduced weight gain compared to Zucker fa/fa controls. 2 day washout phase, body weight gain still reduced compared to Zucker fa/fa controls. I-4 was well tolerated.

BIBLIOGRAPHY

Cronshaw J M and Matunis M J. 2004. The nuclear pore complex: disease associations and functional correlations TRENDS Endocrin Metab. 15:34-39

Falini B et al. 2006. Both carboxy-terminus NES motif and mutated tryptophan(s) are crucial for aberrant nuclear export of nucleophosmin leukemic mutants in NPMc+ AML Blood. 107:4514-4523.

Cai X and Liu X. 2008. Inhibition of Thr-55 phosphorylation restores p53 nuclear localization and sensitizes cancer cells to DNA damage.PNAS. 105:16958-16963.

Daelemans D, Afonina E, Nilsson J 2002 A synthetic HIV-1 Rev inhibitor interfering with the CRM1-mediated nuclear export. Proc Natl Acad Sci USA 99(22):14440-5.98052-2517.

Davis J R et al. 2007. Controlling protein compartmentalization to overcome disease Pharmaceut Res. 24:17-27.

Freundt E, Yu L, Park E, et al 2009 Molecular determinants for subcellular localization of the severe acute respiratory syndrome coronavirus open reading frame 3b protein. J Virol 83(13):6631-40.

Ghildyal R, Ho A, Dias M, et al 2009 The respiratory syncytial virus matrix protein possesses a Crm1-mediated nuclear export mechanism. J Virol 83(11):5353-62.

Ghosh C C et al 2008 Analysis of nucleocytoplasmic shuttling of N F kappa B proteins in human leukocytes. Methods Mol Biol. 457:279-92.

Gupta N et al 2008 Retinal tau pathology in human glaucomas. Can J Ophthalmol. 2008 February; 43(1):53-60.

HoshinoL et al. 2008. Combined effects of p53 gene therapy and leptomycin B in human esophageal squamous cell carcinoma. Oncology. 75:113-119.

Lain S et al. 1999a An inhibitor of nuclear export activates the p53 response and induces the localization of HDM2 and p53 to U1A-positive nuclear bodies associated with the PODs Exp Cell Res. 248:457-472.

Lain S et al. 1999b. Accumulating active p53 in the nucleus by inhibition of nuclear export: a novel strategy to promote the p53 tumor suppressor function Exp Cell Res. 253:315.

Muller P A et al. 2009 Nuclear-cytosolic transport of COMMD1 regulates NF-kappaB and HIF-1 activity. Traffic 10(5):514-27.

Mutka S 2007 Nuclear Export Inhibitors (NEIs) as novel cancer therapies AACR Annual Meeting. Poster 5609.

Mutka S, Yang W, Dong S, et al. 2009. Identification of nuclear export inhibitors with potent anticancer activity in vivo. Cancer Res. 69: 510-7.

Nakahara J et al. 2009. Abnormal expression of TIP30 and arrested nucleocytoplasmic transport within oligodendrocyte precursor cells in multiple sclerosis J Clin Invest. 119:169-181.

Noske A et al. 2008. Expression of the nuclear export protein chromosomal region maintenance/exportin 1/Xpo1 is a prognostic factor in human ovarian cancer. Cancer. 112:1733-1743.

Pollard V & Malim M. 1998 The HIV-1 Rev protein Annu Rev Microbiol 52:491-532.

Rawlinson S, Pryor M, Wright P, Jans D 2009 CRM1-mediated nuclear export of dengue virus RNA polymerase NS5 modulates interleukin-8 induction and virus production. J Biol Chem 284(23):15589-97.

Sanchez V, Mahr J, Orazio N, et al 2007 Nuclear export of the human cytomegalovirus tegument protein pp65 requires cyclin-dependent kinase activity and the Crm1 exporter. J Virol 81(21):11730-6.

Sorokin A V et al. 2007. Nucleocytoplasmic transport of proteins. Biochemistry 72:1439-1457.

Terry L J et al. 2007. Crossing the nuclear envelope: hierarchical regulation of nucleocytoplasmic transport. Science 318:1412-1416.

Van der Watt P J et al. 2008. The Karyopherin proteins, Crm1 and Karyopherin beta1, are overexpressed in cervical cancer and are critical for cancer cell survival and proliferation. Int J Canc. 124:1829-1840.

Walsh M D et al. 2008 Exportin 1 inhibition attenuates nuclear factor-kappaB-dependent gene expression. Shock 29:160-166.

Williams P, Verhagen J, Elliott G 2008 Characterization of a CRM1-dependent nuclear export signal in the C terminus of herpes simplex virus type 1 tegument protein UL47. J Virol 82(21):10946-52.

Yang W 2007 Anti-tumor activity of novel nuclear export inhibitors (NEIs) in multiple murine leukemia models. AACR Annual Meeting. Poster 5597.

Yao Y et al. 2009. The expression of CRM1 is associated with prognosis in human osteosarcoma. Oncol Rep. 21:229-35.

Zimmerman T L et al 2006 Nuclear export of retinoid X receptor alpha in response to interleukin-Ibeta-mediated cell signaling: roles for JNK and SER260. J Biol Chem281:15434-15440.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for treating multiple myeloma in a subject in need thereof comprising administering to the subject a therapeutically effective amount of a compound represented by the following structural formula I-3:

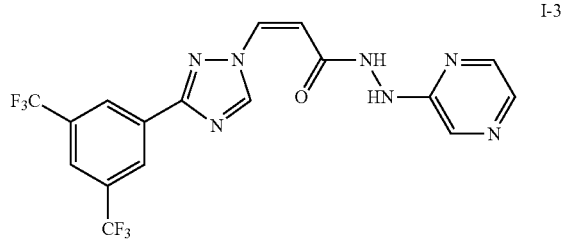 [SMILES: O=C(/C=C\n1cnc(-c2cc(C(F)(F)F)cc(C(F)(F)F)c2)n1)NNc1cnccn1]

or a pharmaceutically acceptable salt thereof and an additional therapeutic agent selected from bortezomib, dexamethasone or a combination thereof.

2. The method of claim 1, wherein the additional therapeutic agent is bortezomib.

3. The method of claim 1, wherein the additional therapeutic agent is dexamethasone.

4. The method of claim 1, wherein the additional therapeutic agent is a combination of bortezomib and dexamethasone.

5. The method of claim 1, wherein the compound of structural formula I-3 and the additional therapeutic agent are administered in separate dosage forms.

6. The method of claim 2, wherein the compound of structural formula I-3 and the additional therapeutic agent are administered in separate dosage forms.

7. The method of claim 3, wherein the compound of structural formula I-3 and the additional therapeutic agent are administered in separate dosage forms.

8. The method of claim 4, wherein the compound of structural formula I-3 and the additional therapeutic agent are administered in separate dosage forms.

9. The method of claim 1, wherein the compound of structural formula I-3 and the additional therapeutic agent are administered at the same time.

10. The method of claim 2, wherein the compound of structural formula I-3 and the additional therapeutic agent are administered in at the same time.

11. The method of claim 3, wherein the compound of structural formula I-3 and the additional therapeutic agent are administered at the same time.

12. The method of claim 4, wherein the compound of structural formula I-3 and the additional therapeutic agent are administered at the same time.

13. The method of any one of claims 1-12, wherein the compound of structural formula I-3 is orally administered.

* * * * *